US012606600B2

(12) United States Patent
Shah et al.

(10) Patent No.: US 12,606,600 B2
(45) Date of Patent: Apr. 21, 2026

(54) ANTIMICROBIAL NCR2 PEPTIDES

(71) Applicant: Donald Danforth Plant Science Center, St. Louis, MO (US)

(72) Inventors: Dilip M. Shah, St. Louis, MO (US); Siva L. S. Velivelli, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 807 days.

(21) Appl. No.: 17/310,582

(22) PCT Filed: Feb. 7, 2020

(86) PCT No.: PCT/US2020/017265
§ 371 (c)(1),
(2) Date: Aug. 12, 2021

(87) PCT Pub. No.: WO2020/176224
PCT Pub. Date: Sep. 3, 2020

(65) Prior Publication Data
US 2022/0098249 A1      Mar. 31, 2022

Related U.S. Application Data

(60) Provisional application No. 62/811,297, filed on Feb. 27, 2019.

(51) Int. Cl.
| | |
|---|---|
| *A61K 38/16* | (2006.01) |
| *A01N 63/60* | (2020.01) |
| *C07K 14/415* | (2006.01) |
| *C12N 15/82* | (2006.01) |

(52) U.S. Cl.
CPC ............ *C07K 14/415* (2013.01); *A01N 63/60* (2020.01); *C12N 15/8282* (2013.01)

(58) Field of Classification Search
None
See application file for complete search history.

(56) References Cited

U.S. PATENT DOCUMENTS

| | | | |
|---|---|---|---|
| 7,825,297 | B2 | 11/2010 | Shah et al. |
| 8,592,367 | B2 | 11/2013 | Kondorosi-Kuzsel et al. |
| 10,253,328 | B2 | 4/2019 | Shah |
| 2012/0157374 | A1 | 6/2012 | Kondorosi-Kuzsel et al. |
| 2015/0283204 | A1 | 10/2015 | Van Der Weerden et al. |
| 2015/0322452 | A1 | 11/2015 | Wang et al. |
| 2016/0208278 | A1 | 7/2016 | Shah |
| 2019/0185877 | A1 | 6/2019 | Boyle et al. |
| 2019/0194268 | A1 | 6/2019 | Shah et al. |
| 2020/0060286 | A1 | 2/2020 | Martinez et al. |
| 2020/0181639 | A1 | 6/2020 | Venkata |
| 2022/0061333 | A1 | 3/2022 | Shah et al. |

OTHER PUBLICATIONS

Genbank entry RHN44149, entered 2018.*
Guo, Haiwei H. et al, "Protein tolerance to random amino acid change." PNAS (2004) 101(25) p. 9205-9210.*
Yampolsky, Lev Y. et al, "The exchangeability of amino acids in proteins." Genetics (2005) 170 p. 1459-1472.*
Lowe, Derek, "Not alphafold's fault." Blog "In the Pipeline" entry of Sep. 7, 2022.*
Malamud, Danial et al,"Isoelectric points of proteins: a table." Anal. Biochem. (1978) 86 p. 620-647.*
Uniprot, "Nodule cysteine-rich protein 13," Uni Prot Accession No. A0AOU8SNQ0, Mar. 16, 2016, 1 page.
United States Patent and Trademark Office in connection with U.S. Appl. No. 17/309,920, filed Jun. 30, 2021, "Requirement for Restriction" 6 pages, mailed Jun. 15, 2023.
Campopiano et al., "Structure-Activity Relationships in Defensin Dimers," The Journal of Biological Chemistry, Nov. 19, 2004, vol. 279, No. 47, pp. 48671-48679.
Haag et al., "Role of Cysteine Residues and Disulfide Bonds in the Activity of a Legume Root Nodule-specific, Cysteine-rich Peptide," Journal of Biological Chemistry, Mar. 30, 2012, vol. 287, No. 14, pp. 10791-10798.
International Search Report and Written Opinion in PCT/US2020/017265, mailed Jul. 2, 2020, 13 pages.
Islam et al., "A novel bi-domain plant defensin MtDef5 with potent broad-spectrum antifungal activity binds to multiple phospholipids and forms oligomers," Scientific Reports, Nov. 23, 2017, vol. 7, Article No. 16157, pp. 1-13.
Montiel et al., "Terminal bacteroid differentiation is associated with variable morphological changes in legume species belonging to the inverted repeat-lacking clade," Molecular Plant-Microbe Interactions, Mar. 2016, vol. 29, No. 3, pp. 210-219.
Ordogh et al., "Symbiotic Plant Peptides Eliminate Candida albicans Both In Vitro and in an Epithelial Infection Model and Inhibit the Proliferation of Immortalized Human Cells," BioMed Research International, Aug. 28, 2004, vol. 2014, Article ID. 320796, 9 pages.
Shabab et al., "Disulfide cross-linking influences symbiotic activities of nodule peptide NCR247," PNAS, Sept. 6, 2016, vol. 113, No. 36, pp. 10157-10162.
Velivelli et al., "Antifungal symbiotic peptide NCR044.1 exhibits unique structure and multi-faceted mechanisms of action that confer plant protection," Feb. 20, 2020, 51 pages.

* cited by examiner

*Primary Examiner* — Fred H Reynolds
(74) *Attorney, Agent, or Firm* — McKee, Voorhees & Sease, PLC

(57)      ABSTRACT

Antimicrobial nodule specific cysteine rich (NCR2) peptides and proteins are disclosed along with compositions comprising the NCR2 peptides or NCR2 proteins and transgenic or genetically edited plants or microorganisms that express the NCR2 peptides or proteins to inhibit growth of pathogenic microbes. Such NCR2 peptides, proteins, compositions, plants, and microorganisms can provide for inhibition of fungal and oomycete growth.

8 Claims, 8 Drawing Sheets
Specification includes a Sequence Listing.

Relative lesion size
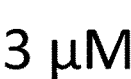
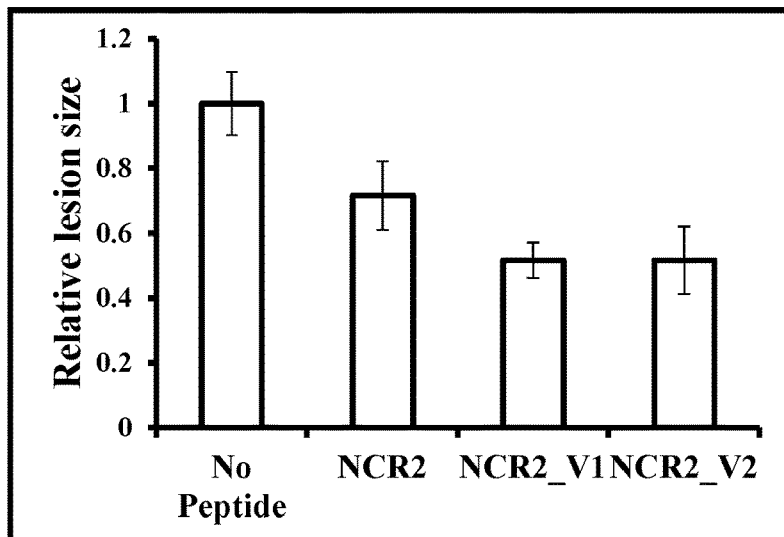
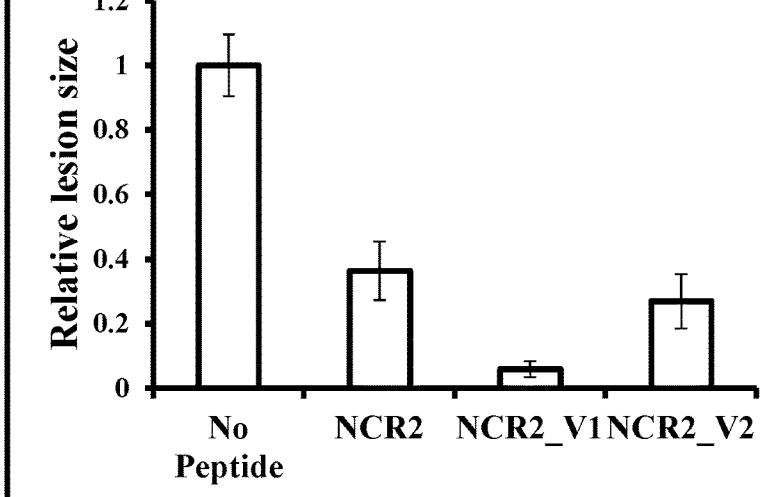
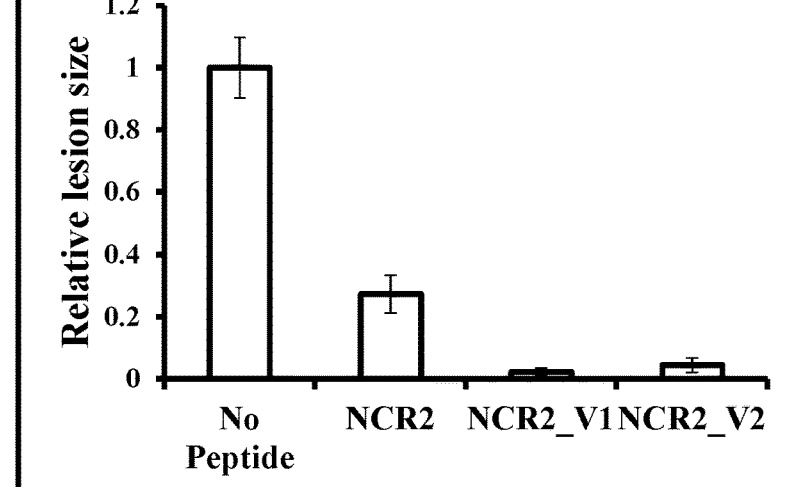
Figure 1B

Figure 3:
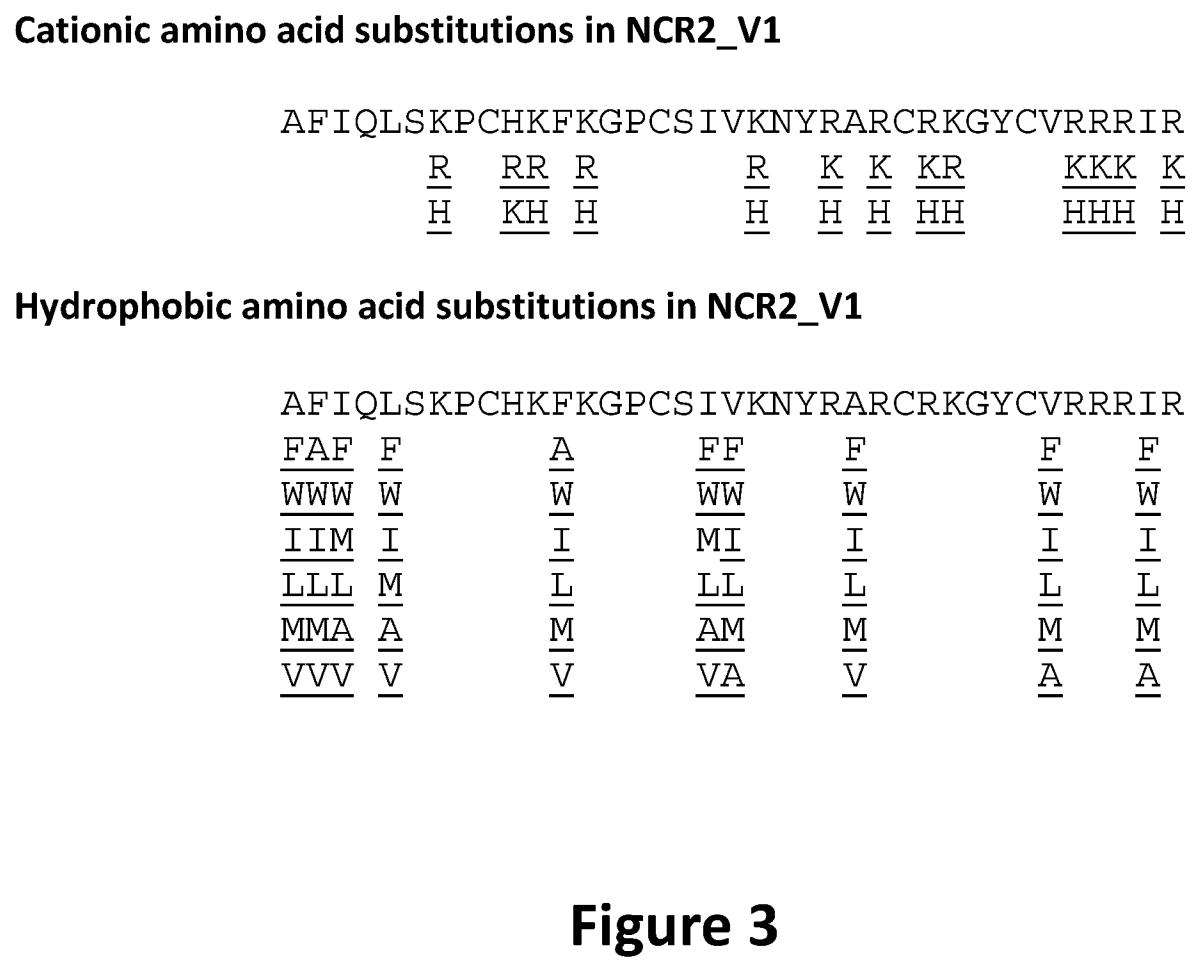

Cationic amino acid substitutions in NCR2_V1

```
AFIQLSKPCHKFKGPCSIVKNYRARCRKGYCVRRRIR
           R  RR R          R  K  K  KR KKK K
           H  KH H          H  H  H  HH HHH H
```

Hydrophobic amino acid substitutions in NCR2_V1

```
AFIQLSKPCHKFKGPCSIVKNYRARCRKGYCVRRRIR
FAF F  A  FF F  F  F  F
WWW W  W  WW W  W  W  W
IIM I  I  MI I  I  I  I
LLL M  L  LL L  L  L  L
MMA A  M  AM M  M  M  A
VVV V  V  VA V  V  A  A
```

ANTIMICROBIAL NCR2 PEPTIDES

CROSS-REFERENCE TO RELATED APPLICATIONS

This U.S. patent application is the U.S. national phase of International Patent Application PCT/US2020/017265, which claims the benefit of U.S. provisional patent application No. 62/811,297 filed Feb. 27, 2019, and incorporated herein by reference in its entirety.

SEQUENCE LISTING STATEMENT

A replacement sequence listing containing the file named 47004_193611_RPLC_ST25.txt which is 18,209 bytes (measured in MS-Windows®) and created on May 17, 2025, comprises 53 sequences, and is incorporated herein by reference in its entirety.

FIELD

The present disclosure relates to antimicrobial nodule specific cysteine rich (NCR) peptides and proteins and recombinant or edited polynucleotides encoding the NCR peptides and proteins. The antimicrobial NCR peptides or proteins can be applied directly to a plant, human, or animal, applied to a plant in the form of microorganisms that produce the peptides, or the plants can be genetically transformed or edited to produce the peptides or proteins. The present disclosure also relates to recombinant polynucleotides, edited polynucleotides, edited genomes, microorganisms and plants comprising those polynucleotides or genomes, and compositions useful in controlling pathogenic microbes.

BACKGROUND

Protection of agriculturally important crops from pathogenic microbes (e.g., fungi, including mold, yeast and dimorphic fungi, or oomycetes) is crucial in improving crop yields. Fungal infections are a particular problem in damp climates and can become a major concern during crop storage, where such infections can result in spoilage and contamination of food or feed products with fungal toxins. Unfortunately, modern growing methods, harvesting and storage systems can promote plant pathogen infections.

Certain microbes (e.g., fungi, including yeast, or oomycetes) can also be pathogenic to various vertebrates including humans, fish, and the like.

Control of plant pathogens is further complicated by the need to simultaneously control multiple microbes of distinct genera. For example, microbes such as *Alternaria, Ascochyta, Botrytis, Cercospora, Colletotrichum, Diplodia, Erysiphe, Fusarium, Gaeumanomyces, Helminthosporium, Macrophomina, Magnaporthe, Nectria, Peronospora, Phoma, Phakopsora, Phymatotrichum, Phytophthora, Plasmopara, Podosphaera, Puccinia, Pythium, Pyrenophora, Pyricularia, Rhizoctonia, Sclerotium, Sclerotinia, Septoria, Thielaviopsis, Uncinula, Venturia*, and *Verticillium* species are all recognized plant pathogens. Consequently, resistant crop plant varieties or antimicrobial agents that control only a limited subset of microbial pathogens can fail to deliver adequate protection under conditions where multiple pathogens are present. It is further anticipated that plant pathogenic microbes can become resistant to existing antimicrobial agents and crop varieties, which can favor the introduction of new microbial control agents with distinct modes of action to combat the resistant microbes.

A group of peptides and proteins known as defensins have been shown to inhibit plant pathogens. Defensins have been previously identified as small cysteine-rich peptides of about 45-54 amino acids that constitute an important component of the innate immunity of plants (Thomma et al., 2002; Lay and Anderson, 2005; Vriens et al., 2014). Widely distributed in plants, defensins vary greatly in their amino acid composition. However, they all have a compact shape which is stabilized by either four or five intramolecular disulfide bonds. Plant defensins have been characterized as comprising a conserved γ-core motif comprising a conserved GXCX3-9C (where X is any amino acid; SEQ ID NO: 8) sequence (Lacerda et al., 2014). The three dimensional structure of the previously characterized γ-core motif consists of two antiparallel β-sheets, with an interpolated turn region (Lacerda et al., 2014). Antimicrobial activity of certain defensins has been correlated with the presence of positively charged amino acid residues in the γ-core motif (Spelbrink et al., Plant Physiol., 2004; Sagaram et al., 2013).

Several publications have disclosed expression vectors that encode proteins having at least two defensin peptides that are liked by a peptide sequence that can be cleaved by plant endoproteinases (WO2014078900; Vasivarama and Kirti, 2013a; François et al.; Vasivarama and Kirti, 2013b). A MtDef5 proprotein comprising two defensin peptides separated by a small peptide linker has also been disclosed in US Patent Appl. Pub. No. 20160208278. Other multimeric defensin proteins have been disclosed in WO2017156457 and WO2017127558.

Certain nodule specific cysteine rich (NCR) peptides and proteins with antimicrobial activity expressed in nodules of *Medicago truncatula* (Barrel Medic) have been described (WO2010146067). Other NCR peptides from *Cicer arietinum* (Chickpea) have been described and implicated in the terminal differentiation of endosymbiotic bacteria (Montiel et al., 2016, Molec. Plant Microb. Inter. 29: 210-219).

SUMMARY

Recombinant polynucleotides comprising a first polynucleotide encoding a first antimicrobial peptide, wherein the first antimicrobial peptide comprises: (i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7 are provided. In certain embodiments, the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or the first antimicrobial peptide comprises a C-terminal amino acid sequence of SEQ ID NO: 8 or SEQ ID NO: 39.

Recombinant polynucleotides comprising a first polynucleotide encoding a first antimicrobial peptide linked by a spacer peptide to a second antimicrobial peptide, wherein the first and second antimicrobial peptides each comprise one of: (i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40; are provided. In certain embodiments, the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or the first or second antimicrobial peptide comprises a C-terminal amino acid sequence of SEQ ID NO: 8 or SEQ ID NO: 39.

Edited polynucleotides comprising a variant polynucleotide encoding a first antimicrobial peptide, wherein the first antimicrobial peptide comprises: (i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7, wherein said variant polynucleotide is operably linked to a polynucleotide comprising a promoter, wherein the variant polynucleotide comprises at least one nucleotide insertion, deletion, and/or substitution in comparison to the corresponding unedited wild type polynucleotide sequence are provided. In certain embodiments, the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1, the first antimicrobial peptide comprises a C-terminal amino acid sequence of SEQ ID NO: 8 or SEQ ID NO: 39, and/or the corresponding unedited wild type polynucleotide sequence encodes the antimicrobial peptide comprising the amino acid sequence of SEQ ID NO: 7.

Plant nuclear or plastid genomes comprising a first polynucleotide encoding a first antimicrobial peptide, wherein the first antimicrobial peptide comprises: (i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7, wherein the polynucleotide is heterologous to the nuclear or plastid genome and operably linked to an endogenous promoter of the nuclear or plastid genome are provided. In certain embodiments, the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or the first antimicrobial peptide comprises a C-terminal amino acid sequence of SEQ ID NO: 8 or SEQ ID NO: 39.

Edited polynucleotides comprising a variant polynucleotide encoding a first antimicrobial peptide linked by a spacer peptide to a second antimicrobial peptide, wherein the first and second antimicrobial peptides each comprises one of: (i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40; wherein said variant polynucleotide is operably linked to a polynucleotide comprising a promoter, wherein the variant polynucleotide comprises at least one nucleotide insertion, deletion, and/or substitution in comparison to the corresponding unedited wild type polynucleotide sequence are provided. In certain embodiments, the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1, the first or second antimicrobial peptide comprises a C-terminal amino acid sequence of SEQ ID NO: 8 or SEQ ID NO: 39, and/or the corresponding unedited wild type polynucleotide sequence encodes the antimicrobial peptide comprising the amino acid sequence of SEQ ID NO: 7.

Plant nuclear or plastid genomes comprising a first polynucleotide encoding a first antimicrobial peptide linked by a spacer peptide to a second antimicrobial peptide, wherein the first and second antimicrobial peptide each comprise one of: (i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the polynucleotide is heterologous to the nuclear or plastid genome and operably linked to an endogenous promoter of the nuclear or plastid genome are provided. In certain embodiments, the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or the first or second antimicrobial peptide comprises a C-terminal amino acid sequence of SEQ ID NO: 8 or SEQ ID NO: 39.

Cells comprising any of the aforementioned or otherwise disclosed recombinant polynucleotides, edited polynucleotides, or genomes are also provided. In certain embodiments, the cell is a plant, yeast, mammalian, or bacterial cell.

Plants comprising any of the aforementioned or otherwise disclosed recombinant polynucleotides, edited polynucleotides, or genomes are also provided. In certain embodiments, the plant is a monocot crop plant or a dicot crop plant. In certain embodiments, the dicot crop plant is not a chickpea plant. Processed products of the plants are also provided.

Methods for obtaining plants comprising any of the aforementioned or otherwise disclosed recombinant polynucleotides, edited polynucleotides, or genomes that are resistant to infection by a plant pathogenic microbes comprising the steps of (i) introducing the recombinant polynucleotide, the polynucleotide encoding the antimicrobial peptide, the polynucleotide comprising the promoter, a fragment of said polynucleotides, or a combination of said polynucleotides into a plant cell, tissue, plant part, or whole plant; (ii) obtaining a plant cell, tissue, part, or whole plant wherein the recombinant polynucleotide, the polynucleotide encoding the antimicrobial peptide, the polynucleotide comprising the promoter, a fragment of said polynucleotides, or a combination of said polynucleotides has integrated into the plant nuclear or plastid genome; and (iii) selecting a plant obtained from the plant cell, tissue, part or whole plant of step (ii) for expression of a plant pathogenic microbe inhibitory amount of the first antimicrobial peptide, thereby obtaining a plant that is resistant to infection by a plant pathogenic microbe are provided.

Methods for obtaining plants comprising any of the aforementioned or otherwise disclosed edited polynucleotides or genomes that are resistant to infection by a plant pathogenic microbe comprising the steps of: (i) providing: (a) a template polynucleotide comprising the polynucleotide encoding the antimicrobial peptide or a fragment thereof; and (b) an endonuclease or an endonuclease and a guide RNA to a plant cell, tissue, part, or whole plant, wherein the endonuclease or guide RNA and endonuclease can form a complex that can introduce a double strand break at a target site in a nuclear or plastid genome of the plant cell, tissue, part, or whole plant; (ii) obtaining a plant cell, tissue, part, or whole plant wherein at least one nucleotide insertion, deletion, and/or substitution has been introduced into the corresponding wild type polynucleotide sequence; and (iii) selecting a plant obtained from the plant cell, tissue, part or whole plant of step (ii) comprising the edited polynucleotide for expression of a plant pathogenic microbe inhibitory amount of the first antimicrobial peptide, thereby obtaining a plant that is resistant to infection by a plant pathogenic microbe are provided.

Methods for producing plant seed that provide plants resistant to infection by a plant pathogenic microbe that comprises the steps of: (i) selfing or crossing any of the aforementioned or otherwise disclosed plants; and (ii) harvesting seed that comprises the recombinant polynucleotides, edited polynucleotides, or genomes of the plant from the self or cross are provided.

Methods for preventing or reducing crop damage by a plant pathogenic microbe comprising the steps of: (i) placing seeds or cuttings of any of the aforementioned or otherwise disclosed plants in a field where control plants are susceptible to infection by at least one plant pathogenic microbe; and (ii) cultivating a crop of plants from the seeds or cuttings, thereby reducing crop damage by the plant pathogenic microbe are provided.

Compositions comprising a first antimicrobial peptide comprising: (i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7; and an agriculturally, pharmaceutically, or veterinarily acceptable carrier, diluent, or excipient are provided. In certain embodiments, the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or the first antimicrobial peptide comprises a C-terminal amino acid sequence of SEQ ID NO: 8 or SEQ ID NO: 39.

Compositions comprising a first antimicrobial peptide linked by a spacer peptide to a second antimicrobial peptide, wherein the first and second antimicrobial peptides each comprise one of: (i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40; and an agriculturally, pharmaceutically, or veterinarily acceptable carrier, diluent, or excipient are provided. In certain embodiments, the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or the first or second antimicrobial peptide comprises a C-terminal amino acid sequence of SEQ ID NO: 8 or SEQ ID NO: 39.

Methods for preventing or reducing crop damage by a plant pathogenic microbe comprising the step of contacting a plant, a plant seed, or other part of said plant with an effective amount of any of the aforementioned compositions or otherwise disclosed are provided.

Medical devices comprising the device and any of the aforementioned or otherwise disclosed compositions, wherein the device comprises at least one surface that is topically coated and/or impregnated with the composition, are provided.

Methods for treating, preventing, or inhibiting a microbial or yeast infection in a subject in need thereof comprising administering to said subject an effective amount of any of the aforementioned or otherwise disclosed compositions or comprising deploying the aforementioned or otherwise disclosed medical devices are provided.

Any of the aforementioned or otherwise disclosed compositions or medical devices for use in a method of treating, preventing, or inhibiting microbial or yeast infection in a subject in need thereof.

BRIEF DESCRIPTION OF THE FIGURES

FIG. 1B graphically illustrates that NCR2_V1 (SEQ ID NO: 1) and NCR2_V2 (SEQ ID NO: 2) are effective in reducing the sizes of disease lesions caused by *Botrytis cinerea* infection of detached lettuce leaves.

FIG. 2 also shows that NCR2_V1 binds to PI3P, PI4P and PI5P with greater affinity than NCR2.

FIG. 3 shows representative cationic and hydrophobic amino acid substitutions in NCR2_V1 (SEQ ID NO: 1).

DETAILED DESCRIPTION

Definitions

Figure 1A:
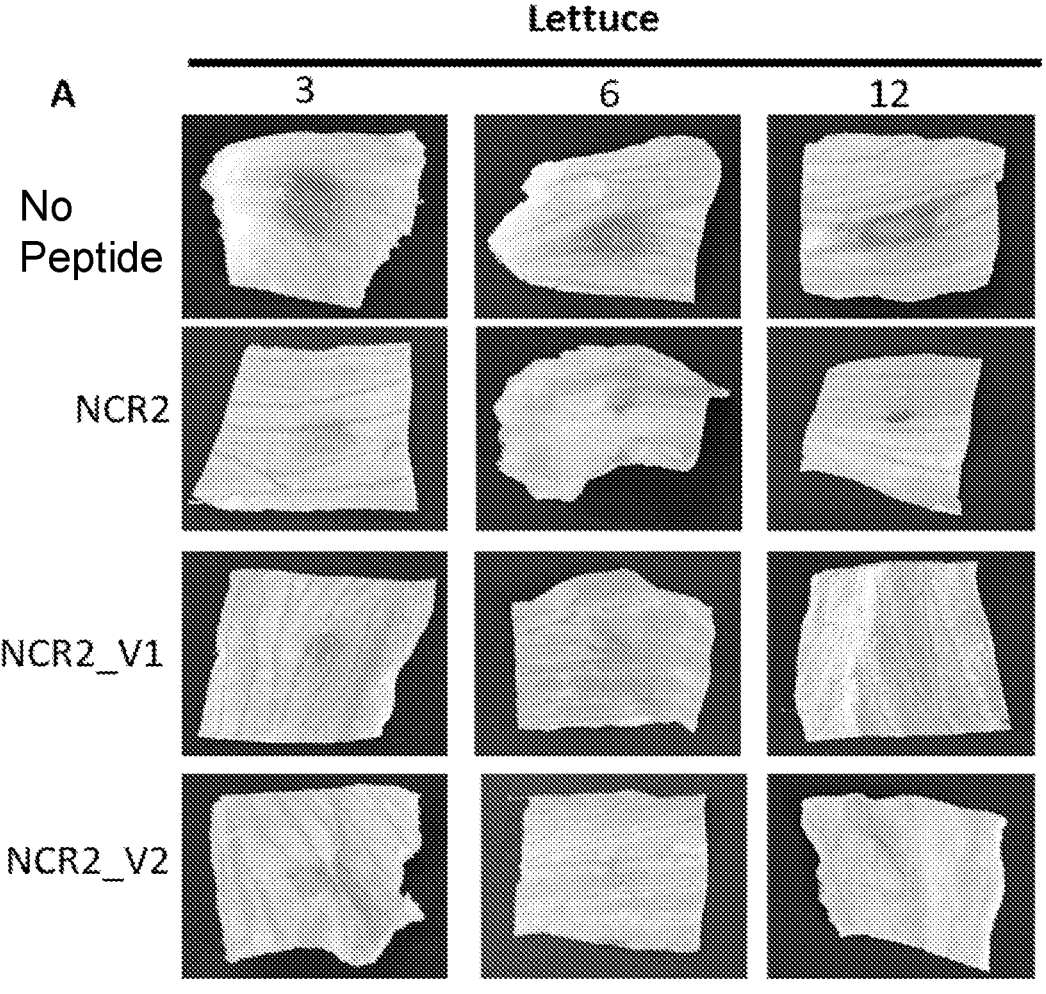
FIG. 1A shows images of lettuce leaves demonstrating that NCR2_V1 (SEQ ID NO: 1) and NCR2_V2 (SEQ ID NO: 2) are effective in reducing the size of disease lesions caused by *Botrytis cinerea* infection of detached lettuce leaves.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and B; B and C; A (alone); B (alone); and C (alone).

The term "comprising" as used herein is to be construed as at least having the features to which it refers while not excluding any additional unspecified features. However, in embodiments provided herein where the term "comprising" is used, other embodiments where the phrases "consisting of" and/or "consisting essentially of" are substituted for the term "comprising" are also provided.

As used herein, the terms "include," "includes," and "including" are to be construed as at least having the features to which they refer while not excluding any additional unspecified features.

Where a term is provided in the singular, other embodiments described by the plural of that term are also provided. For example, the term "a" or "an" entity refers to one or more of that entity; "a peptide," is understood to represent "one or more peptides." As such, the terms "a" (or "an"), "one or more," and "at least one" can be used interchangeably herein.

As used herein, a polynucleotide is said to be "endogenous" to a given cell when it is found in a naturally occurring form and genomic location in the cell.

The phrases "antimicrobial peptide" or "antimicrobial protein" as used herein refer to peptides or proteins which exhibit any one or more of the following characteristics of inhibiting the growth of microbial cells, killing microbial cells, disrupting or retarding stages of the microbial life cycle such as spore germination, sporulation, or mating, and/or disrupting microbial cell infection, penetration or spread within a plant or other susceptible subject, including a human, livestock, poultry, fish, or a companion animal (e.g., dog or cat).

As used herein, the terms "acidic" or "anionic" are used interchangeably to refer to amino acids such as aspartic acid and glutamic acid.

As used herein, the terms "basic" and "cationic" are used interchangeably to refer to amino acids such as arginine, histidine, and lysine.

As used herein, the phrase "consensus sequence" refers to an amino acid, DNA or RNA sequence created by aligning two or more homologous sequences and deriving a new sequence having either the conserved or set of alternative amino acid, deoxyribonucleic acid, or ribonucleic acid residues of the homologous sequences at each position in the created sequence.

The phrases "combating microbial damage", "combating or controlling microbial damage" or "controlling microbial damage" as used herein refer to reduction in damage to a crop plant or crop plant product due to infection by a microbial pathogen. More generally, these phrases refer to reduction in the adverse effects caused by the presence of a pathogenic microbe in the crop plant. Adverse effects of fungal growth are understood to include any type of plant tissue damage or necrosis, any type of plant yield reduction, any reduction in the value of the crop plant product, and/or production of undesirable microbial metabolites or microbial growth by-products including but not limited to mycotoxins.

The phrase "defensin peptide" is used herein to refer to a peptide comprising a conserved γ-core motif comprising a conserved GXCX3-9C sequence (SEQ ID NO: 8), where X is any amino acid residue. Defensin peptides include proteins that are antimicrobial, that can bind phospholipids, that can permeabilize plasma membranes, that can bind sphingolipids, or that exhibit any combination of those properties. A defensin peptide can be naturally occurring or non-naturally occurring (e.g., synthetic and/or chimeric).

As used herein, the terms "edit", "editing," "edited" and the like refer to processes or products where insertions, deletions, and/or nucleotide substitutions are introduced into a genome. Such processes include methods of inducing homology directed repair and/or non-homologous end joining of one or more sites in the genome.

The term "endoproteinase" is used herein to refer to a peptidase capable of cleaving a peptide bond between two internal amino acid residues in a peptide sequence. Endoproteinases can also be referred to as "endoproteases" or "endopeptidases." The proteolytic activity of an endoproteinase, endoprotease, or endopeptidase is thus different that the proteolytic activity of an "exopeptidase" which cleaves peptide bonds of terminal amino acid residues in a peptide.

The phrases "genetically edited plant" or "edited plant" are used herein to refer to a plant comprising one or more nucleotide insertions, deletions, substitutions, or any combination thereof in the genomic DNA of the plant. Such genetically edited plants can be constructed by techniques including CRISPR/Cas endonuclease-mediated editing, meganuclease-mediated editing, engineered zinc finger endonuclease-mediated editing, and the like.

The term "heterologous", as used herein in the context of a second polynucleotide that is operably linked to a first polynucleotide, refers to: (i) a second polynucleotide that is derived from a source distinct from the source of the first polynucleotide; (ii) a second polynucleotide derived the same source as the first polynucleotide, where the first, second, or both polynucleotide sequence(s) is/are modified from its/their original form; (iii) a second polynucleotide arranged in an order and/or orientation or in a genomic position or environment with respect to the first polynucleotide that is different than the order and/or orientation in or genomic position or environment of the first and second polynucleotides in a naturally occurring cell; or (iv) the second polynucleotide does not occur in a naturally occurring cell that contains the first polynucleotide. Heterologous polynucleotides include polynucleotides that promote transcription (e.g., promoters and enhancer elements), transcript abundance (e.g., introns, 5'UTR, and 3'UTR), translation, or a combination thereof as well as polynucleotides encoding NCR peptides or proteins, spacer peptides, or localization peptides. In certain embodiments, a nuclear or plastid genome can comprise the first polynucleotide, where the second polynucleotide is heterologous to the nuclear or plastid genome. A "heterologous" polynucleotide that promotes transcription, transcript abundance, translation, or a combination thereof as well as polynucleotides encoding NCR peptides, spacer peptides, or localization peptides can be autologous to the cell but, however, arranged in an order and/or orientation or in a genomic position or environment that is different than the order and/or orientation in or genomic position or environment in a naturally occurring cell. A polynucleotide that promotes transcription, transcript abundance, translation, or a combination thereof as well as polynucleotides encoding NCR peptides, spacer peptides, or localization can be heterologous to another polynucleotide when the polynucleotides are not operably linked to one another in a naturally occurring cell. Heterologous peptides or proteins include peptides or proteins that are not found in a cell or organism as the cell or organism occurs in nature. As such, heterologous peptides or proteins include peptides or proteins that are localized in a subcellular location, extracellular location, or expressed in a tissue that is distinct from the subcellular location, extracellular location, or tissue where the peptide or protein is found in a cell or organism as it occurs in nature. Heterologous polynucleotides include polynucleotides that are not found in a cell or organism as the cell or organism occurs in nature.

The term "homolog" as used herein refers to a gene related to a second gene by identity of either the DNA sequences or the encoded protein sequences. Genes that are homologs can be genes separated by the event of speciation (see "ortholog"). Genes that are homologs can also be genes separated by the event of genetic duplication (see "paralog"). Homologs can be from the same or a different organism and can in certain embodiments perform the same biological function in either the same or a different organism.

The phrases "inhibiting growth of a plant pathogenic microbe", "inhibit microbial growth", and the like as used herein refers to methods that result in any measurable decrease in microbial growth, where microbial growth includes but is not limited to any measurable decrease in the numbers and/or extent of microbial cells, spores, conidia, or mycelia. As used herein, "inhibiting growth of a plant pathogenic microbe" is also understood to include any measurable decrease in the adverse effects cause by microbial growth in a plant. Adverse effects of microbial growth in a plant include any type of plant tissue damage or necrosis, any type of plant yield reduction, any reduction in the value of the crop plant product, and/or production of undesirable microbial metabolites or microbial growth by-products including but not limited to mycotoxins. As used herein, the phrase "inhibition of microbial growth" and the like, unless otherwise specified, can include inhibition in a plant, human or animal.

As used herein, the phrase "junction sequence", when used in the context of a NCR protein, refers to an amino acid sequence of about six residues where at least three (3) residues are contributed by a spacer peptide and at least three (3) residues are contributed by an NCR peptide. In certain embodiments, 3 amino acids at the N-terminus of the junction sequence are contributed by the final 3 C-terminal residues of the NCR sequence and 3 amino acids at the C-terminus of the junction sequence are contributed by the first 3 N-terminal residues of the spacer peptide sequence. In certain embodiments, 3 amino acids at the N-terminus of the junction sequence are contributed by the final 3 C-terminal residues of the spacer peptide sequence and 3 amino acids at the C-terminus of the junction sequence are contributed by the first 3 N-terminal residues of the NCR peptide sequence.

As used herein, the phrase "linker peptide" refers to any peptide that joins an NCR peptide to another peptide, including an NCR or defensin peptide, in a protein. In certain embodiments, a linker peptide can be susceptible to cleavage by an endoproteinase. In certain alternative embodiments, a linker peptide can be a spacer peptide that is resistant to endoproteinase cleavage. One embodiment where a linker peptide can be (e.g., function as) a spacer peptide is when the linker peptide that joins an NCR peptide to another peptide is localized in an extracellular or sub-cellular location that is deficient in endogenous endoproteinases that can cleave that linker peptide. One embodiment where a linker peptide can be (e.g., function as) a spacer peptide is when the linker peptide is joined to one or more heterologous NCR peptides that render the linker peptide resistant to endoproteinase cleavage. Another embodiment where a linker peptide can be (e.g., function as) a spacer peptide is when the linker peptide is joined to NCR peptide(s) via a heterologous junction sequence or sequences that render the linker peptide resistant to endo-proteinase cleavage. A linker peptide can be naturally occurring or non-naturally occurring (e.g., synthetic).

As used herein, the phrase "linker peptide that is susceptible to cleavage by a endoproteinase," when used in the context of a linker peptide sequence that joins two NCR peptides in a single encoded protein, refers to a linker peptide sequence that permits less than 50% of NCR containing protein in a transgenic or genetically edited organism or cell, an extracellular space of the organism or cell, a sub-cellular location of the organism or cell, or any combination thereof to accumulate as a protein comprising the linker peptide and both peptides that are covalently linked thereto. The phrase "linker peptide that is susceptible to cleavage by a plant endoproteinase," when used in the context of a linker peptide sequence that joins an NCR peptide to another peptide in a single encoded protein, refers to a linker peptide sequence that permits less than 50% of NCR peptide-containing protein in a transgenic or genetically edited plant or cell, an extracellular space of the plant or cell, a sub-cellular location of the plant or cell, or any combination thereof to accumulate as a protein comprising the linker peptide and both peptides that are covalently linked thereto. In certain embodiments, the endoproteinase is an endogenous plant, yeast, or mammalian endoproteinase.

As used herein, the terms "microbe," "microbes," and "microbial" are used to refer to fungi (including yeast) and oomycetes.

As used herein, reference to the terms "NCR2 peptide" or "NCR2 protein" refers to any peptide or protein with anti-microbial activity related by any amino acid sequence conservation to a peptide or protein comprising the amino acid sequence of SEQ ID NO: 1, 2, 3, 4, 5, 6, 7, 31, 32, or 40; to peptides or proteins comprising a variant of the amino acid sequence of SEQ ID NO: 1, 2, 3, 4, 5, 6, 7, 31, 32, or 40; to homologs of peptides or proteins comprising the amino acid sequence of SEQ ID NO: 1, 2, 3, 4, 5, 6, 7, 31, 32, or 40; to a fragment of a peptide or protein comprising the amino acid sequence of SEQ ID NO: 1, 2, 3, 4, 5, 6, 7, 31, 32, or 40, a variant thereof, or a homolog thereof; or to any NCR2 peptide, protein, or fragment thereof set forth in the claims, embodiments, figures, or other disclosure provided herein.

The phrase "operably linked" as used herein refers to the joining of nucleic acid or amino acid sequences such that one sequence can provide a function to a linked sequence. In the context of a promoter, "operably linked" means that the promoter is connected to a sequence of interest such that the transcription of that sequence of interest is controlled and regulated by that promoter. When the sequence of interest encodes a protein that is to be expressed, "operably linked" means that the promoter is linked to the sequence in such a way that the resulting transcript will be efficiently translated. If the linkage of the promoter to the coding sequence is a transcriptional fusion that is to be expressed, the linkage is made so that the first translational initiation codon in the resulting transcript is the initiation codon of the coding sequence. Alternatively, if the linkage of the promoter to the coding sequence is a translational fusion and the encoded protein is to be expressed, the linkage is made so that the first translational initiation codon contained in the 5' untranslated sequence associated with the promoter and the coding sequence is linked such that the resulting translation product is in frame with the translational open reading frame that encodes the protein. Nucleic acid sequences that can be operably linked include sequences that provide gene expression functions (e.g., gene expression elements such as promoters, 5' untranslated regions, introns, protein coding regions, 3' untranslated regions, polyadenylation sites, and/or transcriptional terminators), sequences that provide DNA transfer and/or integration functions (e.g., T-DNA border sequences, site specific recombinase recognition sites, integrase recognition sites), sequences that provide for selective functions (e.g., antibiotic resistance markers, biosynthetic genes), sequences that provide scoreable marker functions (e.g., reporter genes), sequences that facilitate in vitro or in vivo manipulations of the sequences (e.g., polylinker sequences, site specific recombination sequences) and sequences that provide replication functions (e.g., bacterial origins of replication, autonomous replication sequences, centromeric sequences). In the context of an amino acid sequence encoding a localization, spacer, linker, or other peptide, "operably linked" means that the peptide is connected to the polyprotein sequence(s) of interest such that it provides a function. Functions of a localization peptide include localization of a protein or peptide of interest (e.g., an NCR protein or peptide) to an extracellular space or subcellular compartment. Functions of a spacer peptide include linkage of two peptides of interest (e.g., two NCR peptides) such that the peptides will be expressed as a single protein (e.g., an NCR protein dimer).

As used herein, the term "peptide" refers to a molecule of 2 to 55 amino acid residues joined by peptide bonds.

As used herein, the term "protein" refers to a molecule of 56 or more amino acid residues joined by peptide bonds. An "NCR protein" or "NCR2 protein" can refer to any protein comprising an NCR peptide and additional amino acid residues. In certain embodiments, such additional amino acid residues can include a spacer peptide, a linker peptide, an additional NCR peptide, a defensin peptide, or any combination thereof.

The phrases "percent identity" or "sequence identity" as used herein refer to the number of elements (i.e., amino acids or nucleotides) in a sequence that are identical within a defined length of two DNA, RNA or protein segments (e.g., across the entire length of a reference sequence) in an alignment resulting in the maximal number of identical elements, and is calculated by dividing the number of identical elements by the total number of elements in the defined length of the aligned segments and multiplying by 100.

As used herein, the phrase "resistant to cleavage by an endoproteinase," when used in the context of a spacer peptide sequence that joins at least one NCR peptide and another peptide (including an NCR peptide) in a single encoded NCR protein, refers to a spacer peptide sequence that permits more than 50%, 60%, 70%, 80%, 90%, or 95% of the NCR protein in a transgenic or genetically edited organism, cell, extracellular space of the organism or cell, sub-cellular location of the organism or cell, or any combination thereof to accumulate as a NCR protein that comprises the spacer peptide, the NCR and other peptide that is covalently linked thereto. The phrase "resistant to cleavage by a plant endoproteinase", when used in the context of a spacer peptide sequence that joins at least one NCR peptide to another peptide (including an NCR peptide) in a single encoded protein, refers to a spacer peptide sequence that permits more than 50%, 60%, 70%, 80%, 90%, or 95% of the NCR peptide containing NCR protein in a transgenic or genetically edited plant or plant cell, an extracellular space of the plant or cell, a sub-cellular location of the plant or cell, or any combination thereof to accumulate as a NCR protein that comprises the spacer peptide and the NCR and other peptide (including an NCR peptide) that are covalently linked thereto.

As used herein, the phrase "spacer peptide" refers to any peptide that joins NCR peptide to another peptide in a protein that is resistant to cleavage by an endoproteinase. In certain embodiments, the endoproteinase is an endogenous plant, yeast, or mammalian endoproteinase. A spacer peptide can be naturally occurring or non-naturally occurring (e.g., synthetic).

The terms "susceptible microbe (or microbes)", "susceptible microbial infection", and the like refer to microbes that infect plants, or human or animal patients or subjects, or microbial infections thereof, that are subjection to inhibition of microbial growth by the NCR peptides or proteins disclosed herein.

The phrase "transgenic" refers to an organism or progeny thereof wherein the organism's or progeny organism's DNA of the nuclear or organellar genome contains an inserted exogenous DNA molecule of 10 or more nucleotides in length. The phrase "transgenic plant" refers to a plant or progeny thereof wherein the plant's or progeny plant's DNA of the nuclear or plastid genome contains an introduced exogenous DNA molecule of 10 or more nucleotides in length. Such introduced exogenous DNA molecules can be naturally occurring, non-naturally occurring (e.g., synthetic and/or chimeric), from a heterologous source, or from an autologous source.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

DESCRIPTION

Antimicrobial nodule specific cysteine rich peptides and proteins referred to as NCR2 peptides and NCR2 proteins, for example variants of the NCR2 peptide of SEQ ID NO: 7, are provided herein. In certain embodiments, the NCR2 peptides are linked by a spacer peptide that is resistant to plant or other endoproteinase cleavage to provide an NCR2 protein. The antimicrobial peptides and proteins can be applied directly to a plant, applied to a plant in the form of microorganisms that produce the NCR2 peptide or protein, or the plants can be genetically edited to produce the NCR2 peptide or protein. The present disclosure also relates to recombinant or edited polynucleotides, microorganisms and plants transformed with the recombinant nucleic acids, plants comprising genetically edited nuclear or plastid genomes encoding the NCR2 peptides and NCR2 proteins and compositions comprising the NCR2 peptides and NCR2 proteins useful in controlling pathogenic microbes including, but not limited to, plant pathogenic microbes. In certain embodiments, the NCR2 protein can provide for improved inhibition of microbial growth when compared to a peptide or protein containing only one of the antimicrobial peptides found in the NCR2 protein.

NCR2 peptides or proteins provided and used in various embodiments disclosed herein can comprise one or more of the following structural features.

In certain embodiments, a first structural feature of the NCR2 peptides is a net positive charge at neutral pH (Table 1). In certain embodiments, the NCR2 peptides will have a net positive charge at neutral pH of at least +9, +10, +11, +12, +13, +14, or +15. In certain embodiments, the NCR2 peptides will have a net positive charge at neutral pH of at least +5, +6, +7, +8, +9, +10, +11, +12, +13, or +14. In certain embodiments, the NCR peptides will have a net positive charge at neutral pH of +9 or +10 to +13, +14, or +15 or +12 to +13, +14, or +15.

by preferentially substituting a cationic amino acid residue at positions in the NCR2 peptide that correspond to an anionic or neutral polar amino acid residue in SEQ ID NO: 1, 2, 3, 4, 5, 6, 7, or 40. Substitutions of cationic amino acid residues set forth in FIG. 3 for the NCR2 peptide of SEQ ID NO: 1 can also be made in the corresponding amino acid residues of other NCR2 peptides (e.g., SEQ ID NOs: 2, 3, 4, 5, 6, 7, or 40) or NCR proteins comprising such NCR2 peptides (e.g., SEQ ID NO: 31 and 32).

In certain embodiments, a second structural feature of the NCR2 peptides is a significant percentage of hydrophobic amino acid residues (Table 1). In certain embodiments, the NCR2 peptides will comprise at least about 25%, 26%, 28% 30%, 32%, 34%, 36%, 37%, 38%, or 39% hydrophobic amino acid residues. In certain embodiments, the NCR2 peptides will comprise at least about 36%, 37%, 38%, or 39% hydrophobic amino acid residues, or between about 35% to 40% hydrophobic amino acid residues, or between about 36% to 39% hydrophobic amino acid residues. In certain embodiments, the NCR2 peptides will comprise at least about 25%, 26%, 28% 30%, 32%, 34%, or 36% to 37%, 38%, 39%, 40%, 42%, or 45% hydrophobic amino acid residues. In certain embodiments, such percentages of hydrophobic amino acids in NCR2 peptides can be achieved by methods that include: (i) maintaining hydrophobic amino acid residues found in NCR2 peptides including SEQ ID NO: 1, 2, 3, 4, 5, 6, 7, or 40 or substituting such residues with another hydrophobic amino acid residue or neutral polar amino acid residue (e.g.,; (ii) substituting polar amino acid

TABLE 1

The amino acid sequences, net positive charge and hydrophobicity of NCR2 and NCR2 variant peptides

| SEQ ID NO | Peptide | Amino acid sequence | Net charge | % Hydrophobic amino acids |
|---|---|---|---|---|
| 7 | NCR2 | AFIQLSKPCISDKECSIVKNYRARCRKGYCVRRRIR | +9 | 38 |
| 1 | NCR2_V1 | AFIQLSKPCHKFKGPCSIVKNYRARCRKGYCVRRRIR | +12 | 37 |
| 2 | NCR2_V2 | AFCIQLSKPCISDKECSIVKNYRARCRKGYCVRRRIRC | +9 | 39 |
| 3 | NCR2_V3 | AFIQLSKPCKRRRDCSIVKNYRARCRKGYCVRRRIR | +13 | 36 |
| 4 | NCR2_V4 | AFCIQLSKPCKRRRDCSIVKNYRARCRKGYCVRRRIRC | +13 | 39 |
| 5 | NCR2_V5 | AFIQLSKPCKSRKHCSIVKNYRARCRKGYCVRRRIR | +13 | 36 |
| 6 | NCR2_V6 | AFCIQLSKPCKSRKHCSIVKNYRARCRKGYCVRRRIRC | +13 | 39 |
| 40 | NCR2_V7 | AFCQLSKPCHKFKGPCSIVKNYRARCRKGYCVRRRIRC | | |

KRRRD (SEQ ID NO: 36) sequence between the 1$^{st}$ and 2$^{nd}$ cysteine in NCR2_V3 is derived from CaNCR07 (Montiel et al., 2016).
KSRKH (SEQ ID NO: 37) sequence between the 1$^{st}$ and 2$^{nd}$ cysteine in NCR2_V4 is derived from CaNCR15 (Montiel et al., 2016).
ISDKE (SEQ ID NO: 35) sequence between the 1$^{st}$ and 2$^{nd}$ cysteine in NCR2 is very similar to the corresponding QSDKD (SEQ ID NO: 42) sequence in CaNCR13 (Montiel et al., 2016).

In certain embodiments, such net positive charges in NCR2 peptides can be achieved by methods that include: (i) maintaining cationic (basic) amino acid residues found in NCR2 peptides including SEQ ID NO: 1, 2, 3, 4, 5, 6, 7, or 40 or substituting such residues with another cationic amino acid residue; (ii) substituting anionic or polar amino acid residues found in NCR2 peptides including SEQ ID NO: 1, 2, 3, 4, 5, 6, 7, or 40 with a basic amino acid residue; or a combination of (i) and (ii). Examples of such substitutions of cationic amino acid residues in certain NCR2 peptides include those set forth in FIG. 3. In certain embodiments, such net positive charges in NCR2 peptides can be achieved residues found in NCR2 peptides including SEQ ID NO: 1, 2, 3, 4, 5, 6, 7, or 40 with a hydrophobic amino acid residue; (iii) substituting neutral polar amino acids for hydrophobic amino acids; or a combination of (i), (ii), and (iii). Examples of such substitutions of hydrophobic amino acid residues in certain NCR2 peptides include those set forth in FIG. 3. In certain embodiments, such percentages of hydrophobic amino acids in NCR2 peptides can be achieved by substituting a hydrophobic amino acid residue at variable positions in the NCR2 peptide that correspond to a neutral polar amino acid residue of SEQ ID NO: 12, 3, 4, 5, 6, 7, or 40. Substitutions of hydrophobic amino acids set forth in FIG.

3 of the NCR2 peptide of SEQ ID NO: 1 can also be made in the corresponding amino acid residues of other NCR2 peptides (e.g., SEQ ID NO: 2, 3, 4, 5, 6, 7, or 40) or NCR proteins comprising such NCR2 peptides (e.g., SEQ ID NO: 31 or 32).

In certain embodiments, a third structural feature of NCR2 peptides is the presence of one or more, two or more, three or more, or four of the cysteine residues set forth in SEQ ID NO: 1. In certain embodiments, the NCR2 peptide comprises additional cysteine residues such as can be introduced by substitution of a residue for a cysteine and/or by addition of one or more cysteine residues by insertion into, or addition to either N-terminus or C-terminus of, an NCR2 sequence. For example, Table 1 shows that SEQ ID NO: 2 (NCR2_V2) is a variant of SEQ ID NO: 7 (NCR2) except that SEQ ID NO: 2 has a cysteine residue inserted in between positions F2 and I3 of SEQ ID NO: 7 and SEQ ID NO: 2 has a cysteine added to the N-terminus end of SEQ ID NO: 7. SEQ ID NOs: 1 and 40 (NCR2_V1 and NCR2_V7), SEQ ID NOs: 3 and 4 (NCR2_V3 and NCR2_V4, respectively), and SEQ ID NOs: 5 and 6 (NCR2_V5 and NCR2_V6, respectively) are similarly related. In certain embodiments, at least two, at least four, or at least six cysteine residues are covalently linked in NCR2 peptides and proteins provided herein. In certain embodiments, at least two, at least four, or at least six cysteine residues form a disulfide linkage. Certain embodiments can also comprise substitutions of one or more of the cysteine residues (e.g., $C_1$, $C_2$, $C_3$, and $C_4$ in SEQ ID NO:1, where the cysteine residue closest to the amino terminus is $C_1$ and the cysteine residue closest to the carboxy terminus is $C_4$). In certain embodiments, one or more of the cysteine residues can be substituted with another amino acid residue including a glycine, serine, threonine, cysteine, cystine, tyrosine, asparagine, or glutamine residue. In certain embodiments, one or more of the cysteine residues can be substituted with a serine residue. While not being limited by theory, it is believed that NCR2 peptides with substitutions of cysteine residues and that lack one or more disulfide linkages may be desirable for use in transgenic or gene edited plants that are ultimately used as animal feed or as food for human consumption as such variants are predicted to be more readily digested by animals or humans that consume the plant products. Such NCR2 peptides and proteins that have shorter half-lives in the digestive tracts of animals or humans are in theory anticipated to have less potential to become food allergens.

In certain embodiments, a fourth structural feature in certain NCR2 peptides is the presence of a defensin gamma (γ) core consensus sequence GXCX3-9C (SEQ ID NO: 8); where X is any amino acid. In certain embodiments, a defensin gamma core sequence can be created at or near the C-terminus of an NCR2 peptide by the insertion of a C-terminal cysteine residue (e.g., at the C-terminus of SEQ ID NO: 1, 3, 5, or 7). In certain embodiments, an NCR2 peptide comprises or can be modified or substituted to comprise the gamma core sequence GYCVRRRIRC (SEQ ID NO: 33) or GHCRGFRRRC (SEQ ID NO: 38), or a variant thereof comprising an insertion, deletion, and/or substitution of one or more amino acid residues. Examples of NCR2 peptides comprising a C-terminal gamma core motif include NCR2 peptides set forth in SEQ ID NO:2, 4, 6, and 40.

In any of the aforementioned embodiments, the NCR2 peptide(s) can comprise variants of wild-type NCR2 (SEQ IN NO: 7), including but not limited to an amino acid sequence selected from SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7. In any of the aforementioned embodiments, the NCR2 peptide(s) can comprise an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7. In any of the aforementioned embodiments, the NCR2 peptide(s) can comprise an amino acid sequence having at least 60%, 70%, 80%, 85%, 90%, 92%, 95%, 97%, 98%, 99%, or 100% sequence identity across the entire length of SEQ ID NO: 1, wherein the amino acid sequence is selected from SEQ ID NO: 1, 2, 3, 4, 5, 6, 40, or a variant thereof wherein one or more of the hydrophobic, basic, and/or acidic amino acid residues are conservatively substituted with hydrophobic, basic, and/or acidic amino acid residues, respectively, and wherein the amino acid sequence does not comprise SEQ ID NO: 7.

In certain embodiments, spacer peptide domains that can be used to join NCR2 peptides or to join an NCR2 peptide to another peptide (e.g., a defensin peptide) to obtain an NCR2 protein can be obtained from a variety of sources. Examples of spacer peptides that can be used as is or in a mutagenized form include the MtDef5 spacer peptide APKKVEP (SEQ ID NO: 9; L1) and GGKAGKKAPK (SEQ ID NO: 21; L2), as well as SEQ ID NO: 20, 22, 23, 24, 25, and 26. Mutagenesis of any of the aforementioned spacer peptides can entail the insertion, deletion, or substitution of at least one, two, three, four, five, six, or seven amino acid residues in the linker peptide sequence that render the mutagenized linker peptide resistant to cleavage by a plant endoproteinase. Spacer peptides for use in NCR2 proteins that comprise mutagenized linker peptide sequences having at least 60%, 70%, 80%, 85%, 90%, 95%, 96%, 97%, 98%, or 99% sequence identity to any one of SEQ ID NO: 9, 20, 21, 22, 23, 24, 25, or 26 are provided herein. Spacer peptides for use in the NCR2 proteins can also be obtained from multimeric- or multi-domain proteins that do not contain NCR2, defensin or other antimicrobial peptides. Such peptide linker sequences that join peptides in multimeric or multi-domain proteins have been disclosed (Argos, 1990; George R A, Heringa (2002). Examples of suitable peptide sequences from multimeric or multi-domain proteins that can be used as spacer domains include, but are not limited, immunoglobulin hinge regions from immunoglobulins, a linker between the lipoyl and E3 binding domain in pyruvate dehydrogenase (Turner et al., 1993), a linker between the central and C-terminal domains in cysteine proteinase (P9; Mottram et al., 1989), and functional variants thereof. Spacer peptides for use in the NCR proteins can also be wholly or partially synthetic peptide sequences. Such synthetic spacer peptides are designed to provide for a flexible linkage between an NCR and other peptides and to be resistant to cleavage by endogenous plant endoproteinases. In certain embodiments, the length of the synthetic spacer peptide can be between about 3, 4, 8, 10, 12, or 16 and about 20, 24, 28, 30, 40, or 50 amino acid residues in length. In certain embodiments, the synthetic spacer peptide can comprise a glycine-rich or glycine/serine containing peptide sequence. Such sequences can include a (Gly4)n sequence of SEQ ID NO: 46, a $(Gly_4Ser)_n$ sequence of SEQ ID NO: 18, a $Ser(Gly_4Ser)_n$ sequence of SEQ ID NO: 19, combinations thereof, and variants thereof, wherein n is a positive integer equal to 1, 2, 3, 4, 5, 6, 7, 8, 9 or 10. In certain embodiments, such glycine-rich or glycine/serine containing synthetic peptide sequences can also contain threonyl and/or alanyl residues for flexibility as well as polar lysyl and/or glutamyl residues. Additional synthetic linker sequences that can be used as spacer peptides include combinations thereof, and variants thereof. Such variants of synthetic linker sequences include insertions, deletions, and substitutions of amino acid residues. Variants of any of the aforementioned synthetic peptide spacers also include, but are not limited, to insertions and/or substitutions of one or more residues that frequently occur in peptides that join domains in proteins such as prolyl, arginyl, phenylalanyl, threonyl, glutamyl, glutaminyl, and combinations thereof. In certain embodiments, such glycine-rich, glycine/serine containing peptide sequence, or other synthetic peptide spacer sequence can be used to mutagenize a linker peptide sequence. In certain embodiments, mutagenesis of a linker peptide sequence by insertion and/or substitution of a glycine-rich or glycine/serine containing peptide sequence can be used to disrupt a peptide sequence recognized by a plant endoproteinase such as a set of diacidic and/or dibasic residues or a site that is cleaved by a cysteine, serine, threonine, metallo-, or aspartic plant endoproteinase. The composition and design of peptides suitable for flexible linkage of protein domains described in the literature (Chen et al., 2013) can be adapted for use as spacer peptides in the NCR2 proteins provided herein. Spacer peptides useful for joining defensin monomers described in WO/2017/156457 and WO2017127558, which are each incorporated herein by reference in their entireties, can also be used to join NCR2 peptides disclosed herein to other NCR peptides, defensins, antimicrobial peptides, or other peptides.

Since the NCR2 peptides are joined to one another in the NCR2 protein, the spacer peptide sequences and the junction sequences formed by joining either the amino- or carboxy-terminus of an NCR2 peptide to a spacer peptide are in certain embodiments also designed or engineered to be free of amino acid sequences that are susceptible to cleavage by plant or other endoproteinases. In designing NCR2 proteins for expression in plant or other hosts including bacteria, yeast, mammalian cells, and the like, the spacer peptide and junction sequences will typically lack diacidic (aspartyl residues, glutamyl residues, and any combination thereof), dibasic (arginyl residues, lysyl residues, and any combination thereof), or combinations of diacidic and dibasic residues in certain embodiments provided herein. Spacer peptide and junction sequences will typically be resistant to cleavage by at least one of a cysteine, serine, threonine, metallo-, or aspartic plant endoproteinase in certain embodiments provided herein. Amino acid sequences identified as plant endoproteinase substrates (Tsiatsiani et al., 2012) will also typically be absent from spacer peptide and junction sequences in certain embodiments provided herein.

In certain embodiments, the NCR2 proteins provided herein can comprise a spacer peptide or junction sequence that is susceptible to cleavage by a plant endoproteinase when the NCR2 protein is expressed in a plant, plant cell, yeast cell, or mammalian cell in a manner that that will prevent such cleavage. In one such embodiment, the NCR2 protein that comprises a spacer peptide or junction sequence that is susceptible to cleavage by a plant endoproteinase is targeted to an extracellular or sub-cellular compartment where activity of that plant endoproteinase reduced or absent. In certain embodiments where the spacer peptide is resistant to cleavage by endoproteinases in the plant cell cytoplasm, the NCR2 protein can be expressed in the cytoplasm by expressing an NCR2 protein that lacks any targeting signals. In certain embodiments, an NCR2 protein that comprises a spacer peptide or junction sequence that is susceptible to cleavage by a vacuolar plant endoproteinase is targeted to either the apoplast, plastids, mitochondria, or endoplasmic reticulum by operable linkage of suitable localization peptides to that NCR2 protein and/or by removal of any vacuolar localization signal that could have been associated with a given NCR2 peptide or protein. In certain embodiments, an NCR2 protein that comprises a spacer peptide or junction sequence that is susceptible to cleavage by a plastidic plant endoproteinase is targeted to either the apoplast, mitochondria, endoplasmic reticulum, or vacuole by operable linkage of suitable localization peptides to that NCR2 protein and/or by removal of any plastid localization signal that could have been associated with a given NCR2. In certain embodiments, an NCR2 protein that comprises a spacer peptide or junction sequence that is susceptible to cleavage by an apoplastic plant endoproteinase is targeted to either mitochondria, plastids, endoplasmic reticulum, or vacuole by operable linkage of suitable localization peptides to that NCR2. In certain embodiments, an NCR2 that comprises a spacer peptide or junction sequence that is susceptible to cleavage by a mitochondrial plant endoproteinase is targeted to an apoplastic space, plastids, endoplasmic reticulum, or vacuole by operable linkage of suitable localization peptides to that NCR2. Also provided herein are embodiments where an NCR2 protein that comprises one or more spacer peptides that are resistant to cleavage by a plant endoproteinase is targeted to the apoplast, plastids, mitochondria, vacuole, or endoplasmic reticulum.

An NCR2 peptide provided herein can be operably linked to another NCR or NCR2 peptide, defensin, or antimicrobial peptide via a linker peptide sequence that is susceptible to cleavage by a endoproteinase, including a plant endoproteinase. In certain embodiments, the resultant NCR2 protein can be expressed in a cell such that the endoproteinase cleaves the NCR2 protein to provide the NCR2 peptide(s) and, in certain instances, a defensin or other antimicrobial peptide. Such NCR2 proteins can be provided in a cellular compartment (e.g., cytoplasm, mitochondria, plastid, vacuole, or endoplasmic reticulum) or extracellular space (i.e., to the apoplast) having an endoproteinase that cleaves the linker peptide. Cleavable linker peptides are disclosed in WO2014078900, Vasivarama and Kirti, 2013a, François et al., Vasivarama and Kirti, 2013b, and WO2017127558 can be used in the NCR2 proteins provided herein. Other cleavable linker peptide sequences that can be used include SEQ ID NO: 27 and SEQ ID NO: 28.

A variety of different NCR peptides can be used in the NCR2 proteins provided herein. In certain embodiments, the NCR peptides in the NCR2 protein will be identical or related to one another such that the two peptides have at least 60%, 70%, 80%, 85%, 90%, 95%, 98%, 99%, or 100% sequence identity to one another. In certain embodiments, peptides including at least one NCR2 peptide will be distinct and have less than 60% identity to one another. In any of the aforementioned embodiments, the NCR2 peptide(s) can comprise amino acid sequence of SEQ ID NO: 1, 2, 3, 4, 5, 6, 7, 40, or a variant thereof wherein one or more of the hydrophobic, basic, and/or acidic amino acid residues are conservatively substituted with hydrophobic, basic, and/or acidic amino acid residues, respectively. Such conservative substitutions of hydrophobic and/or basic amino acid residues of the amino acid sequence of SEQ ID NO: 1, 2, 3, 4, 5, 6, 7, or 40 include those set forth in the corresponding residues of SEQ ID NO: 1 as shown in FIG. 3. In any of the aforementioned embodiments, the NCR2 peptide(s) can comprise an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40. In certain embodiments, the NCR2 protein can comprise a protein having at least 60%, 70%, 80%, 85%, 90%, 92%, 95%, 97%, 98%, 99%, or 100% sequence identity across the entire length of SEQ ID NO: 31 or 32. In certain embodiments, a defensin peptide used in the NCR2 protein can comprise an amino acid sequence that is at least 70%, 75%, 80%, 85%, 90%, 95%, 98%, or 99% identical to SEQ ID NO: 10, 11, 12, 13, 14, 15, 16, or 17. In any of the aforementioned embodiments, the variant NCR2 peptide(s) can also comprise an amino acid sequence that has at least one, two, three, four, five, six, or seven amino acid insertions, deletions, substitutions, or any combination thereof in a SEQ ID NO: 1, 2, 3, 4, 5, 6, 7, or 40 NCR2 peptide sequence. In certain embodiments, the NCR2 protein can comprise at least two of any of the aforementioned NCR2 peptides, wherein the NCR2 peptides are heterologous to one another. In certain embodiments, the NCR2 proteins can comprise an NCR2 peptide and an MtDef4, MtDef4 H33R, MsDef1, NaD1, TPP3, MtDef5, RsAFP2, DmAMP1, Psd1, HXL005, HXL008, HXL035, HXL036 defensin peptides and/or any defensin, spacer peptide, or linker peptide disclosed in WO2017156457 or WO2017127558, which are each incorporated herein by reference in their entireties. In certain embodiments, the NCR2 proteins can comprise an NCR2 peptide joined by a linker or spacer peptide to a distinct antimicrobial NCR protein disclosed in U.S. Pat. No. 8,592,367, which is incorporated herein by reference in its entirety.

Nucleic acid molecules encoding any of the aforementioned NCR2 peptides or proteins are also provided herein. Such nucleic acids that encode NCR2 peptides or proteins can comprise a synthetic DNA of SEQ ID NO:49, 50, 51, 52, or 53, and variants thereof having at least 60%, 70%, 80%, 85%, 90%, 92%, 95%, 97%, 98%, or 99% sequence identity across the entire length of SEQ ID NO: 49, 50, 51, 52, or 53. Recombinant DNA molecules comprising the aforementioned nucleic acid molecules are also provided herein. Recombinant DNA molecules comprising a heterologous promoter that is operably linked to the aforementioned nucleic acid molecules are also provided herein. Processed plant products including meal and feed comprising a synthetic DNA of SEQ ID NO:49, 50, 51, 52, or 53, and variants thereof having at least 60%, 70%, 80%, 85%, 90%, 92%, 95%, 97%, 98%, or 99% sequence identity across the entire length of SEQ ID NO: 49, 50, 51, 52, or 53 are also provided herein. Processed plant products including meal and feed comprising a fragment of at least about 25, 40, or 50 to about 80 or 100 nucleotides in length comprising synthetic DNA of SEQ ID NO:49, 50, 51, 52, or 53, and variants thereof having at least 60%, 70%, 80%, 85%, 90%, 92%, 95%, 97%, 98%, or 99% sequence identity across the entire length of the aforementioned SEQ ID NO: 49, 50, 51, 52, or 53 fragment are also provided herein.

In certain embodiments, one or more amino acids in any of the aforementioned or other variant NCR2 peptide sequences are substituted with another amino acid(s), the charge and polarity of which is similar to that of the original amino acid, i.e., a conservative amino acid substitution. Substitutes for an amino acid within the NCR2 peptide sequence can be selected from other members of the class to which the originally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (anionic; negatively charged) amino acids such as aspartic acid and glutamic acid; (2) basic (cationic; positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes within NCR2 peptide sequences can be made by substituting one amino acid within one of these groups with another amino acid within the same group. Biologically functional equivalents of NCR2 peptides can have 10 or fewer conservative amino acid changes, seven or fewer conservative amino acid changes, or five, four, three, two, or one conservative amino acid changes. The encoding nucleotide sequence (e.g., gene, plasmid DNA, cDNA, or synthetic DNA) will thus have corresponding base substitutions, permitting it to encode biologically functional equivalent forms of the NCR2 peptides. Certain semi-conservative substitutions in NCR2 peptides including: (i) the substitution of a neutral polar amino acid residue with a neutral nonpolar (hydrophobic) amino acid residue; or (ii) the substitution of a neutral nonpolar (hydrophobic) amino acid residue with a neutral polar amino acid residue are also provided. In particular, semi-conservative substitutions of a neutral polar tyrosine residue with a hydrophobic amino acid residue are provided. Semi-conservative substitutions of a hydrophobic amino acid residue with tyrosine residue are also provided. Biologically functional equivalents of NCR2 peptides can have 10 or fewer semi-conservative amino acid changes, seven or fewer semi-conservative amino acid changes, or five, four, three, two, or one semi-conservative amino acid changes. Non-limiting examples of such conservative substitutions in certain NCR2 peptides are illustrated in FIG. 3.

Functional fragments of any of the aforementioned NCR2 peptides or proteins can comprise NCR2 peptides or proteins having amino terminal deletions, carboxy terminal deletions, internal deletions, or any combination thereof. In certain embodiments, the functional fragment can contain at least one, two, three, four, five, six, or seven or more amino acid residue deletions from the amino terminus, the carboxy terminus, an internal region, or any combination thereof. In certain embodiments, antimicrobial fragments of the NCR2 peptide can comprise at least about 10, 14, 15, 18, or 20 to about 22, 24, 25, 26, 27, or 28 amino acid residues of the C-terminus of the NCR2 peptide.

Chimeric NCR peptides comprising portions of any of the aforementioned or other NCR peptides, NCR peptide variants, NCR fragments, defensin peptides, defensin peptide gamma core sequences, or other defensin peptide fragments can also be used either alone (e.g., as peptides) or in the NCR2 proteins provided herein. In one embodiment, the chimeric NCR peptide can comprise an NCR2 peptide of SEQ ID NO: 2, 4, 6, or 40 wherein the corresponding gamma core sequence found at the C-terminus of those NCR2 peptides is substituted with a distinct gamma core sequence of a defensin peptide (e.g., an MtDef4, MtDef4 H33R, MsDef1, NaD1, TPP3, MtDef5, RsAFP2, DmAMP1, Psd1, HXL005, HXL008, HXL035, or HXL036 defensin peptide). In another embodiment, a C-terminal fragment of an NCR peptide is substituted with a distinct C-terminal fragment of another NCR peptide or with a defensin gamma core peptide (e.g., an MtDef4 gamma core peptide of SEQ ID NO:38 or an MtDef4 H33R gamma core peptide of SEQ ID NO: 48). Chimeric NCR peptides include the NCR2 peptides containing a peptide of a distinct NCR protein, including but not limited to, peptides set forth in SEQ ID NO: 34, 36, or 37, or in U.S. Pat. No. 8,592,367, which is incorporated herein by reference in its entirety. In any of the aforementioned embodiments, the chimeric NCR2 peptide can comprises the amino acid sequence of HKFKGP (SEQ ID NO: 34); KRRRD (SEQ ID NO: 36), or KSRKH (SEQ ID NO: 37) at a position corresponding to between the first and second cysteine residues of SEQ ID NO: 1 (Table 1).

In certain embodiments, the permeability of a microbial plasma membrane treated with the NCR2 protein comprising two NCR2 peptides is increased in comparison to permeability of a microbial plasma membrane treated with single NCR2 peptide of the NCR2 protein. Membrane permeability can be measured by a variety of techniques that include dye uptake. Convenient dye uptake assays that can be used to assess changes in membrane permeability include assays for uptake of Hoechst 33342 (H0342), rhodamine 123, SYTOX™ Green, and the like. These dyes enter into microbial cells only if their plasma membrane has been permeabilized by a defensin or other membrane-permeabilizing agent. Without seeking to be limited by theory, in certain embodiments it is believed that the NCR2 protein comprising an NCR2 peptide and another antifungal peptide joined by a spacer peptide can provide improved microbial inhibition by increasing the permeability of treated microbial membranes in comparison to microbial membranes treated with a NCR2 peptide.

Figure 2:
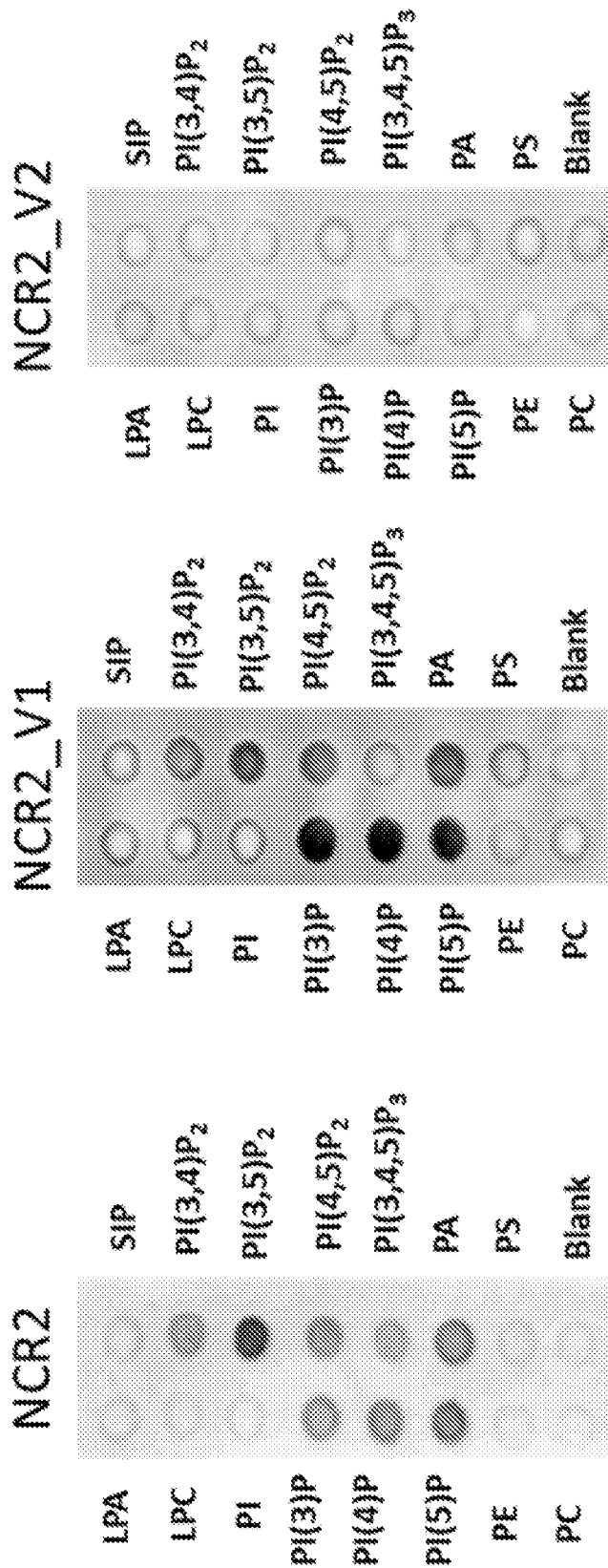
FIG. 2 shows that NCR2 and NCR2_V1 bind to multiple phospholipids, but NCR2_V2 does not bind to any Phospholipids.

In certain embodiments, the NCR2 peptide or peptides used alone or in an NCR2 protein are NCR2 peptides that exhibit binding to a phospholipid. In certain embodiments, NCR2 proteins provided herein comprised of an NCR2 peptide and one or more of the same NCR2 peptide, a distinct NCR2 peptide, an MtDef4, MtDef4 H33R, MsDef1, NaD1, TPP3, MtDef5, RsAFP2, DmAMP1, Psd1, HXL005, HXL008, HXL035, or HXL036 defensin peptides, or variants thereof, can exhibit lower $IC_{50}$ values against one or more microbial pathogens, improved binding to phospholipids, or any combination thereof in comparison to a reference peptide containing just one of the NCR2 or defensin peptides that is contained in the NCR2 protein. In certain embodiments, NCR2 proteins comprised of any combination of an NCR2 peptide and the same NCR2 peptide, a distinct NCR2 peptide, an NCR1, MtDef4, MtDef4 H33R, MsDef1, NaD1, TPP3, MtDef5, RsAFP2, DmAMP1, Psd1, HXL005, HXL008, HXL035, or HXL036 defensin peptide, or variants thereof, and various spacer peptides can be optimized for lower $IC_{50}$ values against one or more microbial pathogens by selecting for NCR proteins having combinations of the NCR2 peptides, NCR2 and defensin peptides, and spacer peptides that provide for improved phospholipid binding in comparison to a reference protein containing just one of the defensin peptides that is contained in the NCR2 protein. In certain embodiments, NCR2 proteins can be optimized for lower $IC_{50}$ values against one or more microbial pathogens by selecting for NCR2 proteins having combinations of the NCR2 peptides, NCR2 and defensin peptides, and spacer peptides that provide for improved phospholipid binding in comparison to a reference protein containing just one of the NCR2 peptides. For example, as shown in FIG. 2, wild-type NCR2 (SEQ ID NO: 7) and NCR2_V1 (SEQ ID NO: 1) bind to multiple phospholipids, but NCR2_V2 (SEQ ID NO: 2) does not bind to any phospholipids. NCR2_V1 binds to PI3P, PI4P and PI5P with greater affinity than the wild-type NCR2 peptide. Suitable assays for determining improved phospholipid include protein-lipid overlay assays (e.g., Dowler et al., 2002), surface plasmon resonance assays (e.g., Baron and Pauron, 2014), biotin capture lipid affinity assays (e.g., Davidson et al., 2006), titration calorimetry assays (e.g., Miller and Cistola, 1993), and the like.

Expression cassettes that provide for expression of the NCR2 peptide or protein in monocotyledonous plants, dicotyledonous plants, or both can be constructed. Such NCR2 peptide or protein expression cassette construction can be effected either in a plant expression vector or in the genome of a plant. Expression cassettes are DNA constructs wherein various promoter, coding, and polyadenylation sequences are operably linked. In general, expression cassettes typically comprise a promoter that is operably linked to a sequence of interest, which is operably linked to a polyadenylation or terminator region. In certain instances including, but not limited to, the expression of recombinant or edited polynucleotides in monocot plants, it can also be useful to include an intron sequence. When an intron sequence is included it is typically placed in the 5' untranslated leader region of the recombinant or edited polynucleotide. In certain instances, it can also be useful to incorporate specific 5' untranslated sequences in a recombinant or edited polynucleotide to enhance transcript stability or to promote efficient translation of the transcript.

A variety of promoters can be used to express the NCR2 peptides or proteins. One broad class of useful promoters are referred to as "constitutive" promoters in that they are active in most plant organs throughout plant development. For example, the promoter can be a viral promoter such as a CaMV35S or FMV35S promoter. The CaMV35S and FMV35S promoters are active in a variety of transformed plant tissues and most plant organs (e.g., callus, leaf, seed and root). Enhanced or duplicate versions of the CaMV35S and FMV35S promoters are particularly useful (U.S. Pat. No. 5,378,619, incorporated herein by reference in its entirety). Other useful promoters include the nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter, and the Figwort Mosaic Virus (FMV) 35S promoter (see, e.g., U.S. Pat. No. 5,463,175, incorporated herein by reference in its entirety). It is understood that this group of exemplary promoters is non-limiting and that one skilled in the art could employ other promoters that are not explicitly cited here to express NCR proteins.

Promoters that are active in certain plant tissues (i.e., tissue specific promoters) can also be used to drive expression of NCR2 peptides or proteins. Expression of NCR2 peptides and proteins in the tissue that is typically infected by a microbial pathogen is anticipated to be particularly useful. Thus, expression in reproductive tissues, seeds, roots, stems, or leaves can be particularly useful in combating infection of those tissues by certain microbial pathogens in certain crops. Examples of useful tissue-specific, developmentally regulated promoters include but are not limited to the 0-conglycinin 7S promoter (Doyle et al., 1986), seed-specific promoters (Lam and Chua, 1991), and promoters associated with napin, phaseolin, zein, soybean trypsin inhibitor, ACP, stearoyl-ACP desaturase, or oleosin genes. Examples of root specific promoters include but are not limited to the RB7 and RD2 promoters described in U.S. Pat. Nos. 5,459,252 and 5,837,876, respectively.

Another class of useful promoters are promoters that are induced by various environmental stimuli. Promoters that are induced by environmental stimuli include promoters induced by heat (e.g., heat shock promoters such as Hsp70), promoters induced by light (e.g., the light-inducible promoter from the small subunit of ribulose 1,5-bisphosphate carboxylase, ssRUBISCO, a very abundant plant protein), promoters induced by cold (e.g., COR promoters), promoters induced by oxidative stress (e.g., catalase promoters), promoters induced by drought (e.g., the wheat Em and rice rab16A promoters), and promoters induced by multiple environmental signals (e.g., rd29A promoters, Glutathione-S-transferase (GST) promoters).

Promoters that are induced by microbial infections in plants can also be used to drive expression of NCR2 peptides and proteins. Useful promoters induced by microbial infections include those promoters associated with genes involved in phenylpropanoid metabolism (e.g., phenylalanine ammonia lyase, chalcone synthase promoters), genes that modify plant cell walls (e.g., hydroxyproline-rich glycoprotein, glycine-rich protein, and peroxidase promoters), genes encoding enzymes that degrade microbial cell walls (e.g., chitinase or glucanase promoters), genes encoding thaumatin-like protein promoters, or genes encoding proteins of unknown function that display significant induction upon microbial infection. Maize and flax promoters, designated as MisI and FisI, respectively, are also induced by microbial infections in plants and can be used (US Patent Appl. Pub. No. 20020115849).

Depending on the microbe to which protection is sought, the present NCR2 peptides and proteins can be expressed in any tissue or organ in the plant where the microbe attacks. In the case of *Fusarium* for example, a useful site for expression is in the roots. In the case of those microbes that infect by entering external plant surfaces, accumulation of the NCR2 peptides and proteins in the apoplast can be used. In certain embodiments, the apoplast-localized NCR2 can be expressed in roots, stems, leaves, etc., by the use of tissue-specific promoters.

Promoters active at particular developmental stages in the plant life cycle can also be used to optimize resistance to microbial infection and/or damage when it is most needed.

An intron can also be included in the DNA expression construct, especially in instances when the sequence of interest is to be expressed in monocot plants. For monocot plant use, introns such as the maize hsp70 intron (U.S. Pat. No. 5,424,412; incorporated by reference herein in its entirety), the maize ubiquitin intron, the Adh intron 1 (Callis et al., 1987), the sucrose synthase intron (Vasil et al., 1989) or the rice Act1 intron (McElroy et al., 1990) can be used. Dicot plant introns that are useful include introns such as the CAT-1 intron (Cazzonnelli and Velten, 2003), the pKAN-NIBAL intron (Wesley et al., 2001; Collier et al., 2005), the PIV2 intron (Mankin et al., 1997) and the "Super Ubiquitin" intron (U.S. Pat. No. 6,596,925, incorporated herein by reference in its entirety; Collier et al., 2005) that have been operably integrated into recombinant or edited polynucleotides. It is understood that this group of exemplary introns is non-limiting and that one skilled in the art could employ other introns that are not explicitly cited here to express NCR2 proteins.

Certain embodiments comprise a sequence encoding an apoplast localization peptides that facilitates secretion of the mature NCR2 peptides or proteins from plant cells. Apoplast localization peptides include peptides referred to as signal peptides. In certain embodiments, apoplast localization peptides can be operably linked to the n-termini of NCR2 peptides or proteins to provide for apoplast localization. Portions of NCR, defensin, or other proproteins that encode apoplast localization peptides (e.g., signal peptides) that can be used for secreting NCR peptides or proteins from plant or other cells. Examples of NCR proproteins that contain apoplast localization peptides that can be used in NCR peptides and proteins include the NCR proproteins disclosed in Montiel et al. 2016. Examples of defensin proproteins that contain apoplast localization peptides that can be used in NCR peptides and proteins include the defensin proproteins of disclosed in U.S. Pat. No. 7,825,297 and US Patent Appl. Pub. No. 20160208278 (each incorporated herein by reference in their entireties), proteins that have at least about 70%, 80%, 90%, 95%, or 99% sequence identity to these sequences, and the biological functional equivalents of these sequences. Alternatively, signal peptide sequences derived from other *Medicago* defensin proteins (Hanks et al., 2005) can be used. Examples of such other *Medicago* defensin protein signal peptides include signal peptides of MtDef1.1 and MtDef2.1. Another example of a useful signal peptide encoding sequence that can be used in monocot plants is the signal peptide derived from a barley cysteine endoproteinase gene (Koehler and Ho, 1990) or an alpha-amylase gene. Another example of a useful signal peptide encoding sequence that can be used in dicot plants is the tobacco PR1b signal peptide. In other embodiments, wholly synthetic signal peptides can be used. This group of signal peptides is meant to be exemplary and non-limiting, and one skilled in the art could employ other signal peptides that are not explicitly cited here.

In other embodiments, sequences encoding peptides that provide for the localization of an NCR2 peptides or proteins in subcellular organelles can be operably linked to the sequences that encode the NCR2 peptides or proteins. NCR2 peptides or proteins that are operably linked to a signal peptide are expected to enter the secretion pathway and can be retained by organelles such as the endoplasmic reticulum (ER) or targeted to the vacuole by operably linking the appropriate retention or targeting peptides to the C-terminus of the NCR2 peptide or protein. Examples of vacuolar targeting peptides include a CTPP vacuolar targeting signal from the barley lectin gene. Examples of ER targeting peptides include a peptide comprising a KDEL amino acid sequence (SEQ ID NO: 41).

In certain embodiments, a plastid localization peptide can be operably linked to the NCR2 peptides or proteins to provide for localization of the NCR2 peptides or proteins in a plant plastid. Plastid transit peptides can be obtained from nuclear-encoded and plastid localized proteins that include Rubisco small subunit (RbcS), chlorophyll a/b-binding protein, ADP-glucose pyrophosphorylase (ADPGPP), and the like. Plastid targeting peptides that been disclosed in non-patent (Li and Teng, 2013) and patent literature (US Patent Appl. Pub. No. 20160017351 and U.S. Pat. No. 5,510,471, each incorporated herein by reference in their entireties). Chimeric plastid targeting peptides have also been disclosed (Lee et al., Plant Physiol., 2015). Any of the aforementioned plastic targeting peptides can be adapted for use in localizing NCR2 peptides or proteins in plastids. In certain embodiments, the plastid localization peptide can be operably linked to the N-terminus of the NCR2 peptides or proteins.

In certain embodiments, a mitochondrial localization peptide can be operably linked to the NCR2 peptides or proteins to provide for localization of the NCR2 peptides or proteins in the mitochondria. Mitochondrial localization peptides can be obtained from nuclear-encoded and mitochondrial localized proteins that include beta-subunit of the F(1)-ATP synthase, alternative oxidases, and the gamma-subunit of the F(1)-ATP synthase. Mitochondrial targeting peptides have been disclosed (Sjoling and Glaser; 1998; Huang et al., Plant Physiology, 2009). In certain embodiments, the mitochondrial localization peptide will be operably linked to the N-terminus of the NCR2 peptides or proteins. Any of the aforementioned mitochondrial targeting peptides can be adapted for use in localizing NCR2 proteins in mitochondria. In certain embodiments, the mitochondrial localization peptide can be operably linked to the N-terminus of the NCR2 peptides or proteins.

In still other embodiments, dual localization peptide(s) can be used to provide for localization of the NCR2 peptides or proteins in both plastids and mitochondria (Carrie and Small, 2013).

Localization of NCR2 peptides or proteins in the apoplast, endoplasmic reticulum, the vacuole, plastids, or mitochondria can provide for useful properties such as increased expression in transgenic or edited plants and/or increased efficacy in inhibiting microbial growth in transgenic or edited plants. In certain embodiments, the localization peptide is a heterologous localization peptide that can direct an operably associated protein or peptide to an extracellular or sub-cellular location that is different than the extracellular or sub-cellular location of a naturally occurring protein or antimicrobial peptides. In certain embodiments, the localization peptide can target an NCR2 protein that comprises a spacer peptide, linker peptide, or junction sequence that is susceptible to cleavage by a plant endoproteinase to an extracellular or sub-cellular compartment where activity of that plant endoproteinase is reduced or absent and thus provide for accumulation of the NCR2 protein in the transgenic or edited plant.

In other embodiments, the NCR2-, defensin-, localization-, spacer-, or other peptide or protein encoding nucleotide sequence can be synthesized de novo from an NCR2 peptide sequence disclosed herein. The sequence of the peptide or protein-encoding nucleotide sequence can be deduced from the NCR2-, defensin-, localization-, spacer-, or other protein sequence through use of the genetic code. Computer programs such as "BackTranslate" (GCG™ Package, Acclerys, Inc. San Diego, CA) can be used to convert a peptide sequence to the corresponding nucleotide sequence that encodes the peptide.

Furthermore, the synthetic NCR2-, defensin-, localization-, spacer-, or other peptide or protein nucleotide sequence can be designed so that it will be optimally expressed in plants. U.S. Pat. No. 5,500,365 describes a method for synthesizing plant genes to optimize the expression level of the protein encoded by the synthesized gene. This method relates to the modification of the structural gene sequences of the exogenous recombinant or edited polynucleotide, to make them more "plant-like" and therefore more efficiently transcribed, processed, translated, and expressed by the plant. Features of genes that are expressed well in plants include use of codons that are commonly used by the plant host and elimination of sequences that can cause undesired intron splicing or polyadenylation in the coding region of a gene transcript. A similar method for obtaining enhanced expression of transgenes in monocotyledonous plants is disclosed in U.S. Pat. No. 5,689,052.

In certain embodiments, an NCR2 encoding sequence can also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' un-translated regions contain polyadenylate signals and represent non-limiting examples of such 3' untranslated regions that can be used. It is understood that this group of polyadenylation regions is non-limiting and that one skilled in the art could employ other polyadenylation regions that are not explicitly cited here.

The DNA constructs that comprise the plant expression cassettes described above can either be constructed in the plant genome by using site specific insertion of heterologous DNA into the plant genome, by mutagenizing the plant genome, and/or by introducing the expression cassette into the plant genome with a vector or other DNA transfer method. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Such *Agrobacterium* vectors can be adapted for use in either *Agrobacterium tumefaciens* or *Agrobacterium rhizogenes*. Selectable markers encoding genes that confer resistance to antibiotics are also typically included in the vectors to provide for their maintenance in bacterial hosts.

Methods of obtaining a transgenic or edited plant capable of inhibiting growth of a plant pathogenic microbe are also provided. In one embodiment, expression vectors suitable for expression of the NCR2 peptide in various dicot and monocot plants are introduced into a plant, a plant cell, a protoplast, or a plant tissue using transformation techniques as described herein. In another embodiment, the NCR2 expression cassette is constructed in the plant nuclear or plastid genome by editing. Next, a transgenic or edited plant containing or comprising the NCR2 expression vector is obtained by regenerating that transgenic or edited plant from the plant, plant cell, protoplast, or plant tissue that received the expression vector or genome edits. The final step is to obtain a transgenic or edited plant that expresses a plant pathogenic microbe inhibitory amount of the mature NCR2 peptide, where a "plant pathogenic microbe inhibitory amount" is a level of NCR2 peptide sufficient to provide any measurable decrease in microbial growth in the transgenic or edited plant and/or any measurable decrease in the adverse effects caused by microbial growth in the transgenic or edited plant.

Any of the NCR2 expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. The aforementioned methods of introducing transgenes are described in US Patent Appl. Pub. No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety. Methods of using bacteria such as *Rhizobium* or *Sinorhizobium* to transform plants are described in Broothaerts, et al., 2005. It is further understood that the NCR2 expression vector can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the expression vector into the chromosome of a plant cell, a protoplast, a plant tissue, or a plant.

Methods of introducing plant mini-chromosomes comprising plant centromeres that provide for the maintenance of the recombinant mini-chromosome in a transgenic plant (U.S. Pat. Nos. 6,972,197 and 8,435,783) can also be used to introduce and maintain NCR2 in such plants. In these embodiments, the transgenic plants harbor the mini-chromosomes as extrachromosomal elements that are not integrated into the chromosomes of the host plant.

In certain embodiments, transgenic plants can be obtained by linking the gene of interest (in this case an NCR2-encoding polynucleotide sequence) to a selectable marker gene, introducing the linked polynucleotides into a plant cell, a protoplast, a plant tissue, or a plant by any one of the methods described above, and regenerating or otherwise recovering the transgenic plant under conditions requiring expression of the selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, or an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection).

In certain embodiments, a plant comprising a recombinant or edited polynucleotide encoding an NCR2 peptide or protein can be obtained by using techniques that provide for site specific insertion of heterologous DNA into the genome of a plant (e.g., by editing). In certain embodiments, a DNA fragment comprising at least one of a NCR2 peptide, a NCR2 protein, defensin peptide, a spacer peptide that is resistant to cleavage by a plant endoproteinase, a heterologous promoter, or a heterologous localization peptide, is site specifically integrated into the genome to a plant cell, tissue, part, or whole plant to create a sequence within that genome that encodes a NCR2 peptide or protein. In one embodiment of the method, the heterologous DNA encodes a spacer peptide sequence and a NCR2 or defensin peptide that is inserted in-frame at either the N-terminus of the endogenous NCR2 peptide coding region or at the C-terminus of the NCR2 peptide coding region to provide a transgenic or gene edited plant comprising genomic DNA encoding an endogenous NCR2 peptide that is operably linked to a heterologous spacer peptide encoding DNA sequence and an NCR2 or defensin peptide. In certain embodiments where a heterologous DNA that encodes a spacer peptide sequence and an NCR2 or defensin peptide is inserted in frame with an endogenous NCR2 encoding sequence, the inserted and defensin peptide can be identical to the endogenous NCR2 peptide or a variant of the endogenous NCR2 peptide. In certain embodiments, a heterologous promoter or promoter element can be inserted at or near the 5' end of a genomic region that comprises a sequence encoding an endogenous NCR2 peptide or protein to obtain a transgenic or gene edited plant where the genomic region is under the transcriptional control of the inserted or composite promoter. In practicing any of the aforementioned methods, such heterologous DNA can either be inserted in a parallel (e.g., at the same time) or sequentially (e.g., at the distinct times). In one non-limiting example, a heterologous DNA encoding a spacer peptide and an NCR2 or defensin peptide can be inserted into an endogenous genomic region encoding an endogenous NCR2 or defensin peptide at the same time that a heterologous promoter, promoter element, and/or localization peptide is inserted into the genomic region. Examples of methods for inserting foreign DNA at specific sites in the plant genome with site-specific nucleases such as meganucleases or zinc-finger nucleases are at least disclosed in Voytas, 2013. Examples of methods for inserting foreign DNA into the plant genome with clustered regularly interspaced short palindromic repeats (CRISPR)-associated (Cas)-guide RNA technology and a Cas endonuclease are at least disclosed by Svitashev et al., 2015; Murovec et al., 2017; Kumar and Jain, 2015; and in US Patent Appl. Pub. No. 20150082478, which is specifically incorporated herein by reference in its entirety.

In certain embodiments, a genetically edited plant comprising a recombinant or edited polynucleotide encoding an NCR2 peptide or protein can be obtained by using techniques that provide for genome editing in the plant. In one embodiment, the genome of a plant comprising an endogenous gene encoding a defensin or other peptide can be edited to provide a genome, a polynucleotide, or a recombinant polynucleotide comprising an NCR2 peptide or protein. Examples of methods for plant genome editing with clustered regularly interspaced short palindromic repeats (CRISPR)-associated (Cas)-polynucleotide modification template technology and a Cas endonuclease are at least disclosed by Svitashev et al., 2015; Kumar and Jain, 2015; Murovec et al., 2017; and in US Patent Appl. Pub. No. 20150082478, which is specifically incorporated herein by reference in its entirety. Examples of additional methods for editing plant genomes through use of Cpf1 or Csm1 nucleases are disclosed in US Patent Application Publication 20180148735, which is incorporated herein by reference in its entirety.

Transgenic plants can also be obtained by linking a gene of interest (in this case an NCR2-encoding polynucleotide sequence) to a scoreable marker gene, introducing the linked polynucleotides into a plant cell by any of the methods described above, and regenerating the transgenic plants from transformed plant cells that test positive for expression of the scoreable marker gene. The scoreable marker gene can be a gene encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein, or a chloramphenicol acetyl transferase protein.

When an expression vector encoding an NCR2 is introduced into a plant cell or plant tissue or when an NCR2 is introduced in the genome of a plant cell or tissue by site specific insertion of heterologous DNA into the plant genome, the transformed cells or tissues can be regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants has been described (Horsch, R. B. et al., 1985). This regeneration and growth process typically includes the steps of selection of transformed cells and culturing selected cells under conditions that will yield rooted plantlets. The resulting transgenic rooted shoots are thereafter planted in an appropriate plant growth medium such as soil. Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene. In the case of transgenic plant species that reproduce sexually, seeds can be collected from plants that have been "selfed" (self-pollinated) or out-crossed (i.e., used as a pollen donor or recipient) to establish and maintain the transgenic plant line. Transgenic plants that do not sexually reproduce can be vegetatively propagated to establish and maintain the transgenic plant line. In certain embodiments, transgenic plants are derived from a transformation event where the transgene has inserted into one or more locations in the plant genome. In certain embodiments, a seed produced by the transgenic plant, a progeny from such seed, and a seed produced by the progeny of the original transgenic plant are provided. Such progeny and seeds will have an NCR protein-encoding recombinant or edited polynucleotide stably incorporated into their genome, and such progeny plants will inherit the traits afforded by the introduction of a stable recombinant or edited polynucleotide in Mendelian fashion. It is further recognized that transgenic or edited plants containing the NCR2 encoding DNA constructs or edits described herein, and materials derived therefrom, can be identified through use of PCR or other methods that can specifically detect the sequences in the DNA constructs. Methods developed for regeneration and propagation of transgenic plants can be adapted for regeneration and propagation of edited plants.

Once a transgenic or edited plant is regenerated or recovered, a variety of methods can be used to identify or obtain a transgenic or edited plant that expresses a plant pathogenic microbe inhibitory amount of NCR2. One general set of methods is to perform assays that measure the amount of NCR2 that is produced. For example, various antibody-based detection methods employing antibodies that recognize NCR2 can be used to quantitate the amount of NCR2 produced. Examples of such antibody-based assays include ELISAs, RIAs, or other methods wherein an NCR2-recognizing antibody is detectably labelled with an enzyme, an isotope, a fluorophore, a lanthanide, and the like. By using purified or isolated NCR2 peptide as a reference standard in such assays (i.e., providing known amounts of NCR2 peptide), the amount of NCR2 present in the plant tissue in a mole per gram of plant material or mass per gram of plant material can be determined. The NCR2 peptide will typically be expressed in the transgenic or edited plant at the level of "parts per million" or "PPM", where microgram levels of NCR2 are present in gram amounts of fresh weight plant tissue. In this case, 1 microgram of NCR2 per 1 gram of fresh weight plant tissue would represent a NCR2 concentration of 1 PPM. A plant pathogenic microbe inhibitory amount of NCR2 peptide is at least about 0.05 PPM (i.e., 0.05 µg NCR2 peptide per gram fresh weight plant tissue) or at least about 0.1 PPM. In certain embodiments, a plant pathogenic microbe inhibitory amount of NCR2 is at least about 0.5 PPM. In certain embodiments, the amount of NCR2 is at least about 1.0 PPM. In certain embodiments, the amount of NCR2 peptide is at least about 2.0 PPM. In certain embodiments, the amount of the NCR2 protein is at least about 0.05 PPM, 0.1 PPM, 0.5 PPM, or 1.0 PPM to about 5, 10, 20, 50, 100, 200, 500, or 1000 PPM. In certain embodiments, including those where a plastid genome is transformed or edited to express an NCR2 peptide or protein, about 0.1%, 0.2% or 0.5% to about 1%, 3%, 5%, or more of the soluble protein in a plant part, including a leaf, can be the NCR2 peptide or protein.

Alternatively, the amount of NCR2-encoding mRNA produced by the transgenic or edited plant can be determined to identify plants that express plant pathogenic microbe inhibitory amounts of NCR2. Techniques for relating the amount of protein produced to the amount of RNA produced include methods such as constructing a standard curve that relates specific RNA levels (i.e., NCR2 mRNA) to levels of the NCR2 peptide (determined by immunologic or other methods). Methods of quantitating NCR2 mRNA typically involve specific hybridization of a polynucleotide to either the NCR2 mRNA or to a cDNA (complementary DNA) or PCR product derived from the NCR2 RNA. Such polynucleotide probes can be derived from either the sense and/or antisense strand nucleotide sequences of the NCR2-encoding recombinant or edited polynucleotide. Hybridization of a polynucleotide probe to the NCR2 mRNA or cDNA can be detected by methods including, but not limited to, use of probes labelled with an isotope, a fluorophore, a lanthanide, or a hapten such as biotin or digoxigenin. Hybridization of the labelled probe can be detected when the NCR2 RNA is in solution or immobilized on a solid support such as a membrane. When quantitating NCR2 RNA by use of a quantitative reverse-transcriptase Polymerase Chain Reaction (qRT-PCR), the PCR product can be detected by use of any of the aforementioned labelled polynucleotide probes, by use of an intercalating dye such as ethidium bromide or SYBR green, or use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, CA) or when the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, S. A.; 2002). Fluorescent probes that are activated by the action of enzymes that recognize mismatched nucleic acid complexes (i.e., Invader™, Third Wave Technologies, Madison, WI) can also be used to quantitate RNA. Those skilled in the art will also understand that RNA quantitation techniques such as Quantitative Nucleic Acid Sequence Based Amplification (Q-NASBA™) can be used to quantitate NCR-encoding mRNA and identify expressing plants.

Transgenic or edited plants that express plant pathogenic microbe inhibitory amounts of NCR2 peptides can also be identified by directly assaying such plants for inhibition of the growth of a plant pathogenic microbe. Such assays can be used either independently or in conjunction with MDD expression assays to identify the resistant transgenic or edited plants.

Infection of certain plants with certain plant pathogen microbes can result in distinctive effects on plant growth that are readily observed. Consequently, one can distinguish NCR2-expressing transgenic or edited plants by simply challenging such plants transformed with NCR2-encoding recombinant or edited polynucleotides with pathogenic plant microbes and observing reduction of the symptoms normally associated with such infections. Such observations are facilitated by co-infecting otherwise identical, non-transgenic control plants that do not contain an NCR2 encoding recombinant or edited polynucleotide with the same type and dose of plant pathogenic microbes used to infect the transgenic or edited plants that contain an NCR2-encoding recombinant or edited polynucleotide. Identification of transgenic or edited plants that control or combat microbial infection can be based on observation of decreased disease symptoms, measurement of the decreased microbial growth in the infected plant (e.g., by determining the numbers of colony forming units per gram of infected tissue) and/or by measurement of the amount of mycotoxins present in infected plant tissue. The use of microbial disease severity assays and colony formation assays in conjunction with expression assays to identify transgenic MsDef1-expressing potato plants that are resistant to *Verticillium dahliae* has been described (U.S. Pat. No. 6,916,970 and Gao et al., 2000). It is similarly anticipated that a variety of NCR-expressing transgenic or edited plants that combat or control microbial pathogens can be identified by scoring transgenic or edited plants for resistance to microbial pathogens that infect those plants. Examples of NCR recombinant or edited polynucleotide-conferred microbial resistance that can be assayed by observing reductions in disease symptoms or reductions in microbial growth include resistance of transgenic or edited corn to *Fusarium verticillioides, Fusarium moniliforme, Colletotrichum graminicola, Stenocarpella maydis*, and/or *Cercospora zeae-maydis*; resistance of transgenic or edited wheat to head blight (*Fusarium graminearum*), powdery mildew (*Erysiphe graminis* f. sp. *tritici*), stripe rust, stem rust or leaf rust (*Puccinia tritici*); resistance of transgenic or edited cotton to *Fusarium oxysporum* and *Verticillium dahlia*; resistance of transgenic or edited rice to *Magnaporthe oryzae* and *Rhizoctonia solani*, and resistance of transgenic or edited soybean to Asian Soybean rust (*Phakopsora pachyrhizi*), *Phytophthora* Root Rot (*Phytophthora* sp.), White Mold (*Sclerotinia* sp.), Sudden Death Syndrome (*Fusarium virguliforme*) and/or Brown Stem Rot (*Phialophora gregata*).

Transgenic or edited plants that express plant pathogenic microbe inhibitory amounts of NCR2 can also be identified by measuring decreases in the adverse effects cause by microbial growth in such plants. Such decreases can be ascertained by comparing the extent of the adverse effect in an NCR2-expressing transgenic or edited plant relative to an otherwise identical, non-transgenic or unedited control plant that does not express NCR2. Adverse effects of microbial growth in a plant that can be measured include any type of plant tissue damage or necrosis, any type of plant yield reduction, any reduction in the value of the crop plant product, and/or production of undesirable microbial metabolites or microbial growth by-products including, but not limited to, mycotoxins. Mycotoxins comprise a number of toxic molecules produced by microbial species, including but not limited to polyketides (including aflatoxins, demethylsterigmatocystin, O-methylsterigmatocystin, etc.), fumonisins, alperisins (e.g., A1s A2, B1s B2), sphingofungins (A, B, C and D), trichothecenes, fumifungins, and the like. Methods of quantitating mycotoxin levels are widely documented. Moreover, commercial kits for measurement of the mycotoxins such as aflatoxin, fumonisin, deoxynivalenol, and zearalenone are also available (VICAM, Watertown, MA, USA).

A wide variety of plants that express NCR2 can either be constructed by using site specific insertion of heterologous DNA into the plant genome, by mutagenizing the plant genome, and/or by introducing the expression cassette into the plant genome with a vector or other DNA transfer method to obtain transgenic or edited plants that combat or control microbial infections, or that resist such infections.

Plants of interest include both food crop plants and biofuels or energy crop plants, as listed above. Transgenic or edited monocot plants obtainable by the expression vectors and methods described herein include but are not limited to barley, corn, flax, oat, rice, rye, sorghum, turf grass, sugarcane, and wheat. Transgenic or edited dicot plants obtainable by the expression vectors and methods described herein include but are not limited to alfalfa, *Arabidopsis*, barrel medic, banana, broccoli, bean, cabbage, canola, carrot, cassava, cauliflower, celery, citrus, cotton, cucurbits, *eucalyptus*, garlic, grape, onion, lettuce, pea, peanut, pepper, potato, poplar, pine, sunflower, safflower, soybean, strawberry, sugar beet, sweet potato, tobacco, and tomato.

Expression of NCR2 peptides and proteins in yeast is also specifically contemplated herein. The construction of expression vectors for production of heterologous proteins in various yeast genera is well established. In general, such expression vectors typically comprise a promoter that is operably linked to a sequence of interest which is operably linked to a polyadenylation or terminator region. Examples of yeast genera that have been used to successfully express heterologous genes include *Candida, Kluveromyces, Hansuela, Pichia, Saccharomyces, Schizosaccharomyces*, and *Yarrowia*. A general description of expression vectors and transformation systems for *Saccharomyces* is found in Kingsman et al (1985). Expression vectors and transformation systems useful for yeasts other than *Saccharomyces* are described in Reiser et al (1990).

In general, the promoter and polyadenylation region are selected based on their operability in a given yeast host. For example, the AOX1 or AOX2 promoters of *Pichia* can be used in conjunction with the AOX1, AOX2, p40, or p76 polyadenylation sequences of *Pichia* to express a heterologous protein such as an NCR peptide. Both the AOX1 and AOX2 promoters are particularly useful in *Pichia* as both promoters provide for abundant expression of the linked heterologous gene when induced by addition of methanol to the growth medium. The use of these *Pichia* promoters and polyadenylation sequences is described in U.S. Pat. No. 4,855,231, which is expressly incorporated herein by reference in its entirety. Similarly, the Hansuela MOX, DHAS, or FMDH promoters can be used to express heterologous proteins such as NCR in Hansuela. The MOX, DHAS, or FMDH promoters are particularly useful in Hansuela as these promoters provide for abundant expression of the linked heterologous gene when induced by addition of methanol to the growth medium. The use of the MOX and DHAS promoters in Hansuela is described in U.S. Pat. No. 5,741,672, while the use of the FMDH promoter in Hansuela is described in U.S. Pat. No. 5,389,525, each of which is expressly incorporated herein by reference in its entirety. For

*Kluveromyces*, a Lactase promoter and polyadenylation sequence can be used to express heterologous genes such as NCR. Expression of heterologous genes that are operably linked to the Lactase promoter and polyadenylation sequence is achieved by growing *Kluveromyces* in the presence of galactose. The use of the Lactase promoter and polyadenylation sequences in *Kluveromyces* is described in U.S. Pat. No. 6,602,682, which is expressly incorporated herein by reference in its entirety.

Yeast expression vectors that provide for secretion of heterologous proteins such as NCR2 into the growth medium by transformed yeast are also contemplated. Secretion of the mature NCR2 peptide is typically achieved by operable linkage of a signal peptide sequence or a signal peptide and propeptide sequence to the mature NCR2 protein- or peptide-encoding sequence. Examples of useful signal peptides for secretion of heterologous proteins in yeast include but are not limited to an alpha-factor signal peptide, an invertase signal peptide, and a PHO1 signal peptide, all of which are derived from yeast. The alpha-factor signal peptide is typically derived from *Saccharomyces, Kluveromyces*, or *Candida*, while the PHO1 signal peptide is derived from *Pichia*.

A particularly useful signal peptide sequence or signal peptide and propeptide sequence for secretion of proteins in yeast is derived from the *S. cerevisiae* alpha-factor, and is described in U.S. Pat. Nos. 4,546,082, 4,588,684, 4,870,008, and 5,602,034, each of which is expressly incorporated herein by reference in its entirety. The *S. cerevisiae* alpha-factor signal peptide and propeptide sequence consist of amino acids 1-83 of the primary, unprocessed translation product of the *S. cerevisiae* alpha mating factor gene (GenBank Accession Number: P01149). In certain embodiments, the signal peptide sequence of the alpha-mating factor comprising amino acids 1 to about 19 to 23 of the alpha-mating factor proprotein can be directly linked to the N-terminus of the mature NCR2 protein to provide for secretion of mature NCR2 protein. In this case, the signal peptide is cleaved from the mature NCR2 protein in the course of the secretion process. Alternatively, the signal peptide and propeptide of the alpha mating factor can be operably linked to the mature NCR2 encoding sequence via a cleavage site sequence. This cleavage site sequence can comprise a variety of sequences that provide for proteolytic processing of the leader sequence and gene of interest. In the native *S. cerevisiae* alpha mating factor gene the s cleavage site sequence corresponds to amino acid residues 84-89 and is represented by the sequence Lys84-Arg85-Glu86-Ala87-Glu88-Ala 89 (SEQ ID NO:30). The sequence Lys-Arg corresponds to a KEX2 protease recognition site while the Glu-Ala-Glu-Ala sequence corresponds to a duplicated dipeptidylaminopeptidase or STE13 recognition site. In certain embodiments, a DNA fragment encoding the 89 amino acid *S. cerevisiae* alpha factor signal, propeptide coding region, and entire native spacer coding region (i.e., the N-terminal 89 amino acid residues of the alpha mating factor precursor protein containing both the Lys-Arg KEX2 protease cleavage site at residues 84 and 85 as well as the Glu-Ala-Glu-Ala dipeptidylaminopeptidase or STE13 recognition site at residues 86-89) is operably linked to the sequence encoding the mature NCR2 protein. When the N-terminal 89 amino acids of the alpha mating factor precursor protein are fused to the N-terminus of a heterologous protein such as NCR2, the propeptide sequence is typically dissociated from the heterologous protein via the cleavage by endogenous yeast proteases at either the KEX2 or STE13 recognition sites. In other embodiments, a DNA fragment encoding the smaller 85 amino acid *Saccharomyces cerevisiae* alpha factor signal peptide, propeptide, and KEX2 spacer element (i.e., the N- terminal 85 amino acid residues of the alpha mating factor precursor protein containing just the Lys-Arg KEX2 protease cleavage site at residues 84 and 85) is operably linked to the sequence encoding the mature NCR2 protein. When the N-terminal 85 amino acids of the alpha mating factor precursor protein are fused to the N-terminus of a heterologous protein such as NCR2, the propeptide sequence is typically dissociated from the heterologous protein via cleavage by endogenous yeast proteases at the KEX2 recognition site. The NCR2 protein can thus be expressed without the glu-ala repeats.

To obtain transformed yeast that express NCR2 peptides and proteins, the yeast NCR2 expression cassettes (e.g., yeast promoter, yeast signal peptide encoding sequence, mature NCR2 protein sequence, and polyadenylation sequence) are typically combined with other sequences that provide for selection of transformed yeast. Examples of useful selectable marker genes include genes encoding a ADE protein, a HIS5 protein, a HIS4 protein, a LEU2 protein, a URA3 protein, ARG4 protein, a TRP1 protein, a LYS2 protein, a protein conferring resistance to a bleomycin or phleomycin antibiotic, a protein conferring resistance to chloramphenicol, a protein conferring resistance to G418 or geneticin, a protein conferring resistance to hygromycin, a protein conferring resistance to methotrexate, an a AR04-OFP protein, and a FZF1-4 protein.

DNA molecules comprising the yeast NCR2 expression cassettes and selectable marker genes are introduced into yeast cells by techniques such as transfection into yeast spheroplasts or electroporation. In certain embodiments, the DNA molecules comprising the yeast NCR2 expression cassettes and selectable marker genes are introduced as linear DNA fragments that are integrated into the genome of the transformed yeast host cell. Integration can occur either at random sites in the yeast host cell genome or at specific sites in the yeast host cell genome. Integration at specific sites in the yeast host cell genome is typically accomplished by homologous recombination between sequences contained in the expression vector and sequences in the yeast host cell genome. Homologous recombination is typically accomplished by linearizing the expression vector within the homologous sequence (for example, within the AOX1 promoter sequence of a *Pichia* expression vector when integrating the expression vector into the endogenous AOX1 gene in the *Pichia* host cell). In other embodiments, the yeast expression cassettes can also comprise additional sequences such as autonomous replication sequences (ARS) that provide for the replication of DNA containing the expression cassette as an extrachromosomal (non-integrated) element. Such extra-chromosomal elements are typically maintained in yeast cells by continuous selection for the presence of the linked selectable marker gene. Yeast artificial chromosomes (YACs) containing sequences that provide for replication and mitotic transmission are another type of vector that can be used to maintain the DNA construct in a yeast host.

Yeast cells transformed with the yeast NCR2 expression cassettes can be used to produce NCR2 peptides and proteins. These NCR2 molecules can be used directly as antimicrobial agents, to produce antimicrobial compositions that can be applied to plants, as immunogens to raise antibodies that recognize the NCR2 peptides, or as reference standards in kits for measuring concentrations of NCR2 peptides and proteins in various samples. The transformed yeast cells expressing NCR2 antimicrobial molecules can also be applied to plants to combat/control pathogenic microbial infections. The methods of producing NCR2 peptides and proteins typically first comprise the step of culturing yeast cells transformed with NCR2 expression cassettes under conditions wherein the yeast cells express a mature NCR2 molecule. In general, the conditions where the yeast cells express the mature NCR2 molecules are conditions that allow for or specifically induce expression of the yeast promoter that is operably linked to the NCR2 coding sequence in the yeast expression cassette. When the yeast is *Pichia* and the signal-peptide/MD gene is under the control of an AOX1 or AOX2 promoter, addition of methanol to the growth medium will provide for expression of mature NCR2 protein. Similarly, when the yeast is Hansuela and the signal-peptide/MD gene is under the control of a MOX, DHAS, or FMDH promoter, addition of methanol to the growth medium will provide for expression of mature NCR2 protein. Alternatively, when the yeast is *Kluveromyces* and the signal-peptide/De/5 gene is under the control of a Lactase promoter, addition of galactose to the growth medium will provide for expression of mature NCR2 protein.

Once the transformed yeast culture has been incubated under culture conditions that provide for expression of mature NCR2 peptide for a sufficient period of time, the mature NCR2 molecule can be isolated from the culture. A sufficient period of time can be determined by periodically harvesting portions or aliquots of the culture and assaying for the presence of NCR2 peptide. Analytical assays such as SDS-PAGE with protein staining, Western blot analysis, or any immunodetection method (e.g., such as an ELISA) can be used to monitor NCR2 production. For example, incubation in the presence of methanol for between 1 to 8 days is sufficient to provide for expression of mature NCR2 protein from the AOX1 promoter in *Pichia*.

Isolation of the NCR2 peptide from the culture can be partial or complete. For NCR2 expression vectors where a yeast signal peptide is operably linked to the sequence encoding the mature NCR2 protein, the mature NCR2 protein can be recovered from the yeast cell culture medium. Yeast cell culture medium that contains the mature NCR2 protein can be separated from the yeast cells by centrifugation or filtration, thus effecting isolation of mature NCR2 protein. Yeast cell culture medium that contains the mature NCR2 protein can be further processed by any combination of dialysis and/or concentration techniques (e.g., precipitation, lyophilization, filtration) to produce a composition containing the NCR2 protein. Production of NCR2 protein can also comprise additional purification steps that result in either a partially or completely pure preparation of the NCR2 protein. To effect such purification, filtration size-exclusion membranes can be used. Alternatively, various types of chromatographic techniques such as size exclusion chromatography, ion-exchange chromatography, or affinity chromatography can be used to produce a partially or completely pure preparation of the NCR2 protein.

Combinations of various isolation techniques can also be employed to produce the mature NCR2 peptide or protein. For example, the cell culture medium can be separated from the cells by centrifugation and dialyzed or adjusted. In certain embodiments, a buffer for dialysis or adjustment is a 25 mM sodium acetate buffer at about pH4.5-pH6.0. This dialysate is then subjected to ion-exchange chromatography. For example, a cation-exchange resin such as CM-Sephadex C-25 equilibrated with a 25 mM sodium acetate buffer at about pH6.0 can be used. NCR2 protein bound to the cation exchange resin is washed and then eluted. For example, the aforementioned column is washed with 25 mM sodium acetate buffer at about pH6.0 and subsequently eluted in 1M NaCl, 50 mM Tris, pH7.6. Fractions containing the NCR2 protein are identified by an assay or by UV absorbance and then concentrated by a size-cutoff filtration membrane. The concentrated NCR2 protein is then dialyzed to obtain an essentially or substantially pure NCR2 protein in a buffer. Buffers include buffers such as 10 mM Tris, pH 7.6.

Also provided are antimicrobial compositions for agricultural, pharmaceutical, or veterinary use comprising either an antimicrobial plant, or antimicrobial human or veterinary, pathogenic microbe inhibitory amount ("antimicrobial effective amount") of one or more the present isolated, purified antimicrobial NCR2 peptides, or biologically functional equivalents thereof. Such compositions can comprise one, or any combination of, NCR2 peptides disclosed herein, and an agriculturally, pharmaceutically, or veterinary-practicably acceptable carrier, diluent, or excipient. As indicated below, other components relevant in agricultural and therapeutic contexts can be included in such compositions as well. The antimicrobial compositions can be used for inhibiting the growth of, or killing, NCR2 protein- or peptide-susceptible pathogenic microbes associated with plant, human or animal microbial infections. Such antimicrobial compositions can be formulated for topical administration, and applied topically to either plants, the plant environment (including soil), or humans or animals.

Agricultural compositions comprising any of the present NCR2 molecules alone, or in any combination, can be formulated as described in, for example, Winnacker-Kuchler (1986) Chemical Technology, Fourth Edition, Volume 7, Hanser Verlag, Munich; van Falkenberg (1972-1973) Pesticide Formulations, Second Edition, Marcel Dekker, N.Y.; and K. Martens (1979) Spray Drying Handbook, Third Edition, G. Goodwin, Ltd., London. Formulation aids, such as carriers, inert materials, surfactants, solvents, and other additives are also well known in the art, and are described, for example, in Watkins, Handbook of Insecticide Dust Diluents and Carriers, Second Edition, Darland Books, Caldwell, N.J., and Winnacker-Kuchler (1986) Chemical Technology, Fourth Edition, Volume 7, Hanser Verlag, Munich. Using these formulations, it is also possible to prepare mixtures of the present NCR2 peptides and proteins with other pesticidally active substances, fertilizers, and/or growth regulators, etc., in the form of finished formulations or tank mixes.

Whether alone or in combination with other active agents, the present antimicrobial NCR2 peptides and proteins can be applied at a concentration in the range of from about 0.1 µg ml to about 100 mg ml, or from about 5 µg ml to about 5 mg ml, at a pH in the range of from about 3.0 to about 9.0. Such compositions can be buffered using, for example, phosphate buffers between about 1 mM and 1 M, about 10 mM to about 100 mM, or about 15 mM to about 50 mM. In the case of low buffer concentrations, a salt can be added to increase the ionic strength. In certain embodiments, NaCl in the range of from about 1 mM to about 1 M, or about 10 mM to about 100 mM, can be added.

Numerous conventional microbial antibiotics and chemical fungicides with which the present NCR2 peptides and proteins can be combined are described in Worthington and Walker (1983) The Pesticide Manual, Seventh Edition, British Crop Protection Council. These include, for example, polyoxines, nikkomycines, carboxy amides, aromatic carbohydrates, carboxines, morpholines, inhibitors of sterol biosynthesis, and organophosphorous compounds. In addition, azole, triazole, and/or echinocandin fungicides can also be used. Other active ingredients which can be formulated in combination with the present antimicrobial peptides and proteins include, for example, insecticides, attractants, sterilizing agents, acaricides, nematicides, and herbicides. U.S. Pat. No. 5,421,839, which is incorporated herein by reference in its entirety, contains a comprehensive summary of the many active agents with which substances such as the present antimicrobial NCR2 peptides and proteins can be formulated.

Agriculturally useful antimicrobial compositions encompassed herein also include those in the form of host cells, such as bacterial and microbial cells, capable of producing the NCR2 peptides and proteins, and which can colonize plants, including roots, shoots, leaves, or other parts of plants. The term "plant-colonizing microorganism" is used herein to refer to a microorganism that is capable of colonizing any part of the plant itself and/or the plant environment, including, and which can express the present NCR2 antimicrobial peptides and proteins in the plant and/or the plant environment. A plant colonizing micro-organism is one that can exist in symbiotic or non-detrimental relationship with a plant in the plant environment. U.S. Pat. No. 5,229,112, which is incorporated herein by reference in its entirety, discloses a variety of plant-colonizing microorganisms that can be engineered to express antimicrobial proteins, and methods of use thereof, applicable to the NCR2 antimicrobial peptides and proteins disclosed herein. Plant-colonizing microorganisms expressing the presently disclosed NCR2 antimicrobial peptides and proteins useful in inhibiting microbial growth in plants include bacteria selected from the group consisting of *Bacillus* spp. including but not limited to *Bacillus thuringiensis, Bacillus israelensis*, and *Bacillus subtilis*, Candidatus Liberibacter *asiaticus; Pseudomonas* spp.; *Arthrobacter* spp., *Azospyrillum* spp., *Clavibacter* spp., *Escherichia* spp.; *Agrobacterium* spp., for example *A. radiobacter, Rhizobium* spp., *Erwinia* spp. *Azotobacter* spp., *Azospirillum* spp., *Klebsiella* spp., *Alcaligenes* spp., *Rhizobacterium* spp., *Xanthomonas* spp., *Ralstonia* spp. and *Flavobacterium* spp., In certain embodiments, the microorganism is a yeast selected from the group consisting of *Saccharomyces cerevisiae, Pichia pastoris*, and *Pichia methanolica*. In certain embodiments, the plant colonizing microorganism can be an endophytic bacteria or microbe.

When applying the present NCR2 molecules to the rhizosphere, rhizosphere-colonizing bacteria from the genus *Pseudomonas* are particularly useful, especially the fluorescent pseudomonads, e.g., *Pseudomonas fluorescens*, which is especially competitive in the plant rhizosphere and in colonizing the surface of the plant roots in large numbers. Examples of suitable phylloplane (leaf) colonizing bacteria are *P. putida, P. syringae*, and *Erwinia* species.

The antimicrobial plant-colonizing microorganisms that can express NCR2 can be applied directly to the plant, e.g., to the surface of leaves, buds, roots, shoots, floral parts, seeds, etc., or to the soil. When used as a seed coating, the plant-colonizing microorganisms that can express NCR2 are applied to the plant seed prior to planting. The determination of an antimicrobial effective amount of plant-colonizing microorganisms used for a particular plant can be empirically determined, and will depend on such factors as the plant species, the microbial pathogen, method of planting, and the soil type, (e.g., pH, organic matter content, moisture content). At least one, 10 or 100 plant-colonizing microorganism(s) containing DNA encoding the NCR2 antimicrobial peptides and proteins disclosed herein is sufficient to control microbial pathogens because it or they can grow into a colony of clones of sufficient number to express antimicrobial amounts of the NCR2. However, in practice, due to varying environmental factors which can affect the survival and propagation of the microorganism, a sufficient number of plant colonizing microorganisms should be provided in the seed, plant or plant environment (e.g., roots or foliage) to assure survival and/or proliferation. For example, application of $10^3$ to $10^{10}$ bacteria or yeasts per seed can be sufficient to insure colonization on the surface of the roots by the microorganism. In certain embodiments, it is sufficient to dose the plant or plant environment with enough bacteria or other plant-colonizing microorganism to maintain a population that expresses 100 to 250 nanograms of the NCR2 per plant. For example, $10^5$ to $10^8$ bacteria per square centimeter of plant surface can be adequate to control microbial infection. In certain embodiments, at least about 5 or 10 nanograms to about 100, 200, 500, or 1,000 nanograms, of a NCR2 protein can be sufficient to control microbial damage to plants.

Compositions containing the plant colonizing microorganisms that express the NCR2 can be prepared by formulating the biologically active microorganism with adjuvants, diluents, carriers, etc., to provide compositions in the form of finely-divided particulate solids, granules, pellets, wettable powders, dusts, aqueous suspensions, dispersions, or emulsions. Illustrative of suitable carrier vehicles are: solvents, e.g., water or organic solvents, and finely divided solids, e.g., kaolin, chalk, calcium carbonate, talc, silicates, and gypsum. In certain embodiments, plant colonizing microorganisms that express the NCR2 can also be in encapsulated form, e.g., the plant-colonizing microorganisms can be encapsulated within shell walls of polymer, gelatin, lipid, and the like. Other formulation aids such as, for example, emulsifiers, dispersants, surfactants, wetting agents, anti-foam agents, and anti-freeze agents, can be incorporated into the antimicrobial compositions, especially if such compositions will be stored for any period of time prior to use.

In addition to the plant-colonizing microorganisms that express NCR2, the compositions provided herein can additionally contain other known biologically active agents, such as, for example, a fungicide, herbicide, or insecticide. Also, two or more plant-colonizing microorganisms that express either a different or the same NCR2 can be combined.

The application of antimicrobial compositions containing the genetically engineered plant-colonizing microorganisms that can express NCR2 as the active agent can be carried out by conventional techniques utilizing, for example, spreaders, power dusters, boom and hand sprayers, spray dusters, and granular applicators.

The compositions provided herein can be applied in an antimicrobial effective amount, which will vary depending on such factors as, for example, the specific fungal pathogen to be controlled, the specific plant (and plant part or soil) to be treated, and the method of applying the compositions that comprise NCR2 peptides and proteins.

NCR2 peptides and proteins and biologically functional equivalents, as well as transgenic or genetically edited plants or microorganisms expressing those proteins, can be used to inhibit the growth of a wide variety of susceptible microbes in plants. In certain embodiments, growth of microbes in the following genera or species can be inhibited: *Alternaria* (e.g., *Alternaria brassicicola; Alternaria solani*); *Ascochyta* (e.g., *Ascochyta pisi*); *Aspergillus* (e.g., *Aspergillus flavus; Aspergillus fumigatus*); *Botrytis* (e.g., *Botrytis cinerea*); *Cercospora* (e.g., *Cercospora kikuchii; Cercospora zeaemaydis*); *Colletotrichum* (e.g., *Colletotrichum lindemuthianum*); *Diplodia* (e.g., *Diplodia maydis*); *Erysiphe* (e.g.,

*Erysiphe graminis* fsp. *graminis; Erysiphe graminis* fsp. *hordei); Fusarium* (e.g., *Fusarium nivale; Fusarium oxysporum; Fusarium graminearum; Fusarium culmorum; Fusarium solani; Fusarium moniliforme; Fusarium roseum); Gaeumanomyces* (e.g., *Gaeumanomyces graminis* fsp. *tritici); Helminthosporium* (e.g., *Helminthosporium turcicum; Helminthosporium carbonum; Helminthosporium maydis); Macrophomina* (e.g., *Macrophomina phaseolina; Magnaporthe grisea); Nectria* (e.g., *Nectria heamatococca); Peronospora* (e.g., *Peronospora manshurica; Peronospora tabacina); Phakopsora* (e.g., *Phakopsora pachyrhizi); Phoma* (e.g., *Phoma betae); Phymatotrichum* (e.g., *Phymatotrichum omnivorum); Phytophthora* (e.g., *Phytophthora cinnamomi; Phytophthora cactorum; Phytophthora phaseoli; Phytophthora parasitica; Phytophthora citrophthora; Phytophthora sojae; Phytophthora infestans); Plasmopara* (e.g., *Plasmopara viticola); Podosphaera* (e.g., *Podosphaera leucotricha); Puccinia* (e.g., *Puccinia sorghi; Puccinia striiformis; Puccinia graminis* fsp. *tritici; Puccinia asparagi; Puccinia recondita; Puccinia arachidis); Pythium* (e.g., *Pythium aphanidermatum; Pythium ultimum); Pyrenophora* (e.g., *Pyrenophora tritici-repentens); Pyricularia* (e.g., *Pyricularia oryzae); Rhizoctonia* (e.g., *Rhizoctonia solani; Rhizoctonia cerealis); Sclerotium* (e.g., *Sclerotium rolfsii); Sclerotinia* (e.g., *Sclerotinia sclerotiorum); Septoria* (e.g., *Septoria lycopersici; Septoria glycines; Septoria nodorum; Septoria tritici); Thielaviopsis* (e.g., *Thielaviopsis basicola); Uncinula* (e.g., *Uncinula necator); Venturia*(e.g., *Venturia inaequalis*); and *Verticillium* (e.g., *Verticillium dahliae; Verticillium albo-atrum*).

Pharmaceutical or veterinary compositions that comprise an antimicrobial effective amount of NCR2 proteins, peptides, or biologically functional equivalents thereof and a pharmaceutically acceptable carrier are also provided. Such pharmaceutical or veterinary compositions can be used for inhibiting the growth of, or killing, susceptible pathogenic microbes that infect humans or animals, i.e., treating such fungal infections by administering to a patient or other subject in need thereof. In certain embodiments, compositions comprising NCR2 peptides and proteins, and biologically functional equivalents thereof, can be formulated by methods such as those described in Remington: The Science and Practice of Pharmacy (2005), 21st Edition, University of the Sciences in Philadelphia, Lippincott Williams & Wilkins. In certain embodiments, the compositions can contain NCR2 peptides and proteins, and various combinations thereof, at concentrations in the range of from about 0.1 μg per ml to about 100 mg per ml, or about 5 μg per ml to about 5 mg per ml, at a pH in the range of from about 3.0 to about 9.0. Such compositions can be buffered using, for example, phosphate buffers at a concentration of about 1 mM to about 1 M, about 10 mM to about 100 mM, or about 15 mM to 50 mM. In the case of low buffer concentrations, a salt can be added to increase the ionic strength. In certain embodiments, NaCl in the range of about 1 mM to about 1 M, or about 10 mM to about 100 mM, can be added.

The NCR2 peptides and proteins can be formulated alone, in any combination with one another, and either of these can additionally be formulated in combination with other conventional antimicrobial therapeutic compounds such as, by way of non-limiting example, polyene antimicrobials; imidazole, triazole, and thiazole antimicrobials; allylamines; and echinocandins that are routinely used in human and veterinary medicine.

Administration of the compositions that comprise NCR2 to a human or animal subject in need thereof can be accomplished via a variety of routes that include topical application.

Certain embodiments provide for a recombinant polynucleotide comprising a first polynucleotide encoding a first antimicrobial peptide, wherein the first antimicrobial peptide comprises an amino acid sequence having at least 60%, 70%, 80%, 85%, 90%, 92%, 95%, 97%, 98%, 99%, or 100% sequence identity across the entire length of SEQ ID NO: 1, wherein the amino acid sequence does not comprise SEQ ID NO: 7. In certain of such embodiments, the first antimicrobial peptide comprises a C-terminal amino acid sequence of GXCX3-9C, where X is any amino acid (SEQ ID NO: 8) or GYCX1X2X3X4X5X6X7 (SEQ ID NO: 39); wherein X1 is F, W, I, L, M, or A; wherein X2 is R, K, or H; wherein X3 is R, K, or H; wherein X4 is R, K, or H; wherein X5 is F, W, I, L, M, or A; wherein X6 is R, K, or H; and X7 is C or no amino acid. In certain of any of the aforementioned embodiments, the first antimicrobial peptide comprises a C-terminal amino acid sequence of GYCVRRRIR (SEQ ID NO: 45), GYCVRRRIRC (SEQ ID NO: 33), or GHCRG-FRRRC (SEQ ID NO: 38). In certain of any of the aforementioned embodiments, the first antimicrobial peptide comprises the amino acid sequence of HKFKGP (SEQ ID NO: 34); ISDKE (SEQ ID NO: 35), KRRRD (SEQ ID NO: 36), or KSRKH (SEQ ID NO: 37) at a position corresponding to between the first and second cysteine residues of SEQ ID NO: 1. In any of the aforementioned embodiments, the first antimicrobial peptide comprises an amino acid sequence selected from the group consisting of SEQ ID NO: 2, SEQ ID NO: 3, SEQ ID NO: 4, SEQ ID NO: 5, and SEQ ID NO: 6, or a variant thereof wherein one or more of the hydrophobic, basic, and/or acidic amino acid residues are substituted with hydrophobic, basic, and/or acidic amino acid residues, respectively.

EXAMPLES

Example 1. Antimicrobial and Antioomycete Activity of the Plant Antimicrobial NCR2 Peptides and Proteins Protein Expression and Purification The codon-optimized synthetic genes encoding monomeric NCR peptide NCR2 and its variants, NCR2_V1 and NCR2_V2, and dimeric NCR2 were custom synthesized by GenScript (Piscataway, NJ) and cloned into the EcoRV site of pUC57. An XhoI restriction enzyme site, along with KEX2 protease site (CTCGAGAAAAGA; SEQ ID NO: 43) was introduced upstream of mature NCR peptide coding sequence. A sequence encoding two stop codons and the XbaI restriction endonuclease site (TAGTAATCTAGA; SEQ ID NO: 44) was introduced downstream of the mature NCR peptide coding sequence. For expression in *Pichia pastoris*, DNA sequences encoding the monomeric NCR peptides and variants were cloned between the XhoI and XbaI sites of pPICZαA vector (Invitrogen) in frame with the α-factor secretion signal sequence without the Glu-Ala repeats at the Kex2 signal cleavage site. The pPICZαA vector containing each NCR peptide sequence was linearized by digestion with Sac restriction enzyme and transformed into *P. pastoris* X33 by electroporation. Transformants were selected on yeast extract peptone dextrose medium (YPD) plates containing 150 μg/mL of zeocin, followed by inoculating into YPD broth containing 500 μg/mL of zeocin. Transformants that survived at higher zeocin concentration were used for production of NCR peptides. NCR peptides were generated by recombinant expression in *Pichia pastoris* and purified using the CM-Sephadex C-25 cation-exchange chromatography as described previously with minor modifications (Spelbrink et al. 2004). The *P. pastoris* transformants were grown overnight in buffered minimal glycerol (BMG, Invitrogen) media at 28° C. on a rotary shaker at 225 rpm. Cells were harvested by centrifugation at 8,000 rpm at room temperature (RT) for 15 minutes and re-suspended in buffered minimal methanol (BMM, Invitrogen) media to induce protein expression. The cultures were grown for 4 days at 25° C. at 225 rpm and 0.5% (v/v) methanol was added every 24 hours to maintain the induction. After induction, cells were harvested by centrifugation at 4,000 rpm at 4° C. for 10 minutes, and the pH of the supernatant was adjusted to 6.0. The cation-exchange resin (CM-Sephadex C-25, Cat no: C25120, Sigma) previously equilibrated with binding buffer (25 mM Sodium Acetate Anhydrous, pH 6.0) was added to the supernatant and incubated overnight at 4° C. at 110 rpm. After collecting and washing the resin with a binding buffer, the bound proteins were eluted with the elution buffer (1M NaCl, 50 mM Tris, pH 7.6) using Fast Protein Liquid Chromatography System (AKTA FPLC). The FPLC fractions containing each NCR peptide was concentrated using an Amicon Stirred Cell with a 3-kD cutoff membrane (Millipore, Cat no: PLBC04310). The concentrated fractions were dialyzed against 10 mM Tris, pH 7.6 using an Amicon Ultra-15 Centrifugal Filter Unit with Ultracel-3 membrane (Millipore, Cat no: UFC900324) and further purified by reverse-phase C18 high-performance liquid chromatography (HPLC) and subsequently lyophilized. Each peptide was re-suspended in nuclease-free water and the peptide concentration was determined by either NanoDrop spectrophotometry/the bicinchoninic acid assay (BCA assay). Purity and size of each NCR peptide was determined by electrophoresis on a 4-20% Mini-Protean TGX gels (Biorad, Cat no: 4561094). The correct mass of each peptide with the correct size was confirmed by mass spectrometry and used for experiments described below. The dimeric NCR2 peptide was expressed in *P. pastoris* and purified as described above for the monomeric peptides. Two copies of NCR2 were linked together in tandem using the linker peptide sequence APKKVEP (L1; SEQ ID NO: 9) from the *Medicago truncatula* defensin MtDef5 (Islam et al. 2017) or GGKAGK-KAPK (L2; SEQ ID NO: 21) from the *M truncatula* defensin Mt65L8 (WO 2017/127558 A1). NCR2_V1 loop swap chimeric peptide was produced by replacing the sequence between the first two neighboring cysteine residues of NCR2 with the corresponding sequence (HKFKGP) of *M. truncatula* defensin MtDef4 (Sagaram et al. 2011). NCR2_V2 was cyclized via the introduction of extra disulfide bond into NCR2 by adding one cysteine at N-terminus (in between phenylalanine and isoleucine) and a second cysteine at C-terminus.

Fungal Cultures and Growth Medium

The fungal strains, *Fusarium graminearum* PH-1, *F. virguliforme*, and *F. oxysporum* were routinely cultured on potato dextrose agar (PDA). *Botrytis cinerea* was cultured 10% V8 agar (100 ml/l V8 vegetable juice, 1 g/L CaCO3, 15 g/L agar) plates. The oomycete strain, *Phytophthora capsici* LT263 was stored in 1 ml of sterile distilled water containing 3-4 sterile whole hemp seeds and was routinely cultured on 10% V8 agar containing β-sitosterol (100 ml/L V8 vegetable juice, 1 g/L CaCO3, 0.05 g/L β-sitosterol (Cat no: 85451, Sigma), 15 g/L agar) for 3 days in dark and 3 days under light. For conidia production of *Fusarium graminearum*, the fungus was inoculated into 50 mL of carboxymethyl cellulose medium (CMC, 15 g/L carboxymethyl cellulose, 1 g/L yeast extract, 0.5 g/L MgSO$_4$·7H$_2$O, 1 g/L NH$_4$NO$_3$, and 1 g/L KH$_2$PO$_4$) and cultured for 2-4 days on a rotary shaker at 180 rpm at 28° C. *F. virguliforme*, *F. oxysporum* and *Botrytis cinerea* spores were harvested from culture media plates of 1-2 weeks, by washing the plates with sterile water. The conidial suspension filtered through 2 layers of Miracloth was centrifuged at 13,000 rpm for 1 minute, washed, and the pellet was resuspended in 2× Synthetic Fungal Medium (SFM). The spore suspension was adjusted to a required concentration using hemocytometer. *P. capsici* zoospores were obtained by flooding the culture plates with ice-cold sterile water using a sterile glass spreader. The sporangial suspension filtered through 2 layers of Miracloth was incubated at 4° C. for 30 minutes and then incubated at room temperature under bright light conditions to release zoospores. The zoospore suspension in sterile water was adjusted by diluting with equal volume of 2×SFM and adjusted to a required concentration using hemocytometer.

Antifungal and Anti-Oomycete Activity

The antifungal and anti-oomycete activity was conducted as described previously (Spelbrink et al. 2004; Sagaram et al. 2011; Velivelli et al. 2018) with minor modifications. The antifungal and anti-oomycete activity of NCR peptides were determined in an in vitro assay using 96-well microtiter plates. Fifty microliters of each protein dilution (0, 0.1, 0.3, 0.7, 1.5, 3 and 6 μM) was added to each well of the microtiter plate containing 50 μL of (zoo)spore suspension prepared in 2×SFM at a final concentration of 10$^5$ (zoo) spores/ml. The plates were incubated at room temperature and the quantitative fungal growth inhibition was estimated by measuring the absorbance at 595 nm using a Tecan Infinite M200 Pro (Tecan Systems Inc., San Jose, CA) microplate reader at 48 hours. The fungal/oomycete cell viability/cell killing was determined by the resazurin cell viability assay. After incubation at 48 hours, 10 μl of 0.10% resazurin solution was added to each well and re-incubated overnight. A change from blue to pink color indicates reduction of resazurin and cell viability.

Protein-Phospholipid Overlay Assay

The protein-phospholipid interactions were conducted as described previously (Sagaram et al. 2013) with minor modifications. To test the lipid binding characteristics of NCR peptides, a protein-lipid overlay experiment was performed using PIP Strips™ (2×6 cm nitrocellulose membranes) that are pre-spotted with different biologically active lipids, at 100 pmol per spot, found in cell membranes (Echelon Biosciences, Salt Lake City, UT). Briefly, lipid strips were blocked with 10 mL of blocking buffer, PBS-T/ 3% fat free BSA for 12-16 h at 4° C. with gentle agitation. The blocking buffer was discarded and the lipid strips were incubated with 5 mL of PBS-T/3% fat free BSA, containing 1 μg/ml of NCR peptides for 60 minutes at 4° C. After hybridization, protein solution was discarded and the strips were then washed with PBS-T three times with gentle agitation for 20 minutes each for 1 hour at room temperature. The protein-lipid interactions were detected by subsequently incubating lipid strips with rabbit polyclonal anti-NCR2 antibody (1 μg/ml) diluted in 5 mL of blocking buffer with gentle agitation for 60 minutes at 4° C. The lipid strips were washed with PBS-T two times with gentle agitation, for 15 minutes each wash, at room temperature. HRP-conjugated Mouse Anti-Rabbit IgG secondary antibody (GenScript Cat no A01827) diluted 1:4000 in blocking buffer was added to the lipid strips and incubated for 60 minutes at 4° C. After two washes with PBS-T, chemiluminescence was detected using SuperSignal® West Pico PLUS Sensitivity substrate kit (Thermo Scientific, Cat no: 34080 following the manufacturer's protocol.

In Planta Antifungal Activity of NCR2 and its Variants

Detached leaf infection assays were performed as described previously (Wang et al. 2016) with minor modifications. Briefly, store-bought iceberg lettuce was cut into small pieces of 2×2 cm and placed in Petri dishes. An aliquot of 10 µl of each NCR peptide was drop inoculated onto the leaf samples in different concentrations (3, 6, and 12 µM) and inoculation with *B. cinerea* was carried out at the same spot by applying 10 µl of spore suspension prepared in 2×SFM at a final concentration of $10^5$ spores/ml. Samples were kept in 17.43L×11.81W×6.69H Ziploc WeatherShield plastic boxes containing wet paper towels to maintain a high humidity at room temperature for 48 hours. Lesions were photographed at 48 hours and the relative lesion size was determined using ImageJ software.

Results

Protein Expression and Purification

NCR2 peptide, its variants and dimeric NCR2 were expressed in *P. pastoris* and successfully purified using the cation exchange column chromatography and $C_{18}$ reverse phase HPLC. Each peptide was re-suspended in nuclease-free water and the peptide concentration was determined by either NanoDrop spectrophotometry/the bicinchoninic acid assay (BCA assay). Purity and size of each NCR peptide was determined by electrophoresis on a 4-20% Mini-Protean TGX gels (Biorad, Cat no: 4561094). The mass spec analysis confirmed the correct mass of peptides. A partial degradation of dimeric NCR2 was observed. However, sufficiently pure dimeric peptide was present to allow in vitro antifungal or anti-oomycete tests to be performed.

In Vitro Antifungal Activity of NCR2 and its Variant Peptides

Antifungal activity of the purified NCR2 and its variant peptides against *Fusarium* spp. and *B. cinerea* was determined using the spectrophotometric assay. NCR2 and its variants inhibited the growth of *B. cinerea* with the $IC_{50}$ values of 1.5 to 2 µM and the MIC values of 2 to 3 µM (Table 2).

TABLE 2

In vitro antifungal activity of NCR2 and its variants against *Botrytis cinerea*

| Peptide | B. cinerea | |
| --- | --- | --- |
| | $IC_{50}$ (µM) | MIC (µM) |
| NCR2 | 1.5 | 2-3 |
| NCR2_V1 (SEQ ID NO: 1) | 1.5 | 2-3 |
| NCR2_V2 (SEQ ID NO: 2) | 2 | 3 |

Figure 4:
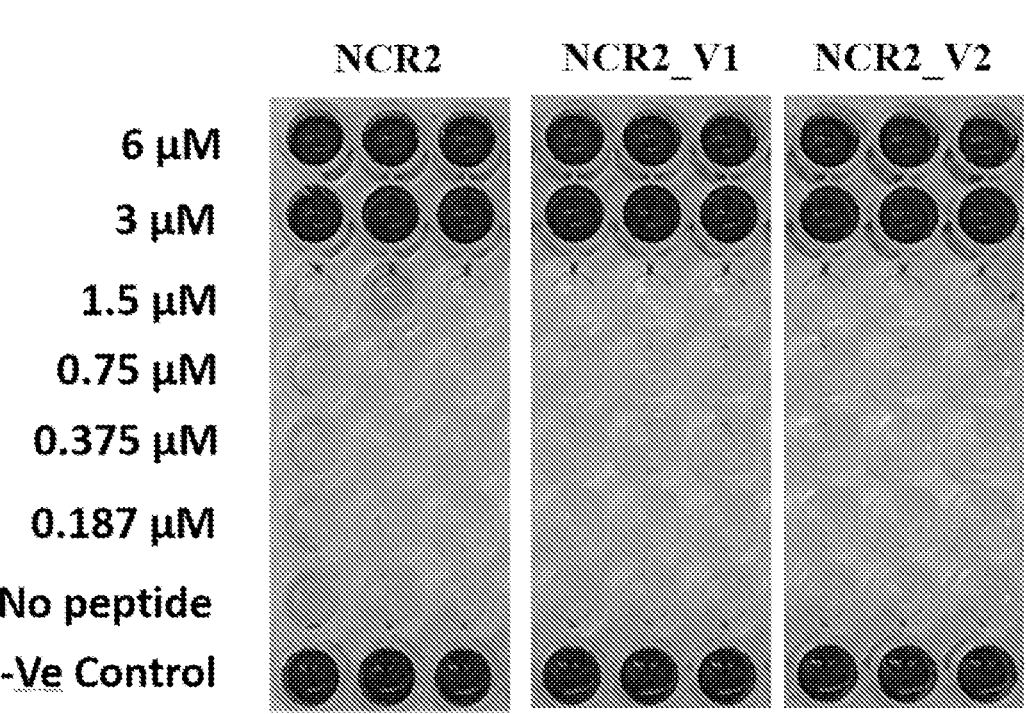
FIG. 4 shows *B. cinerea* growth inhibition by NCR2 and its variants visualized with a fungal cell viability assay using resazurin as a metabolic indicator of living cells.

NCR2 and its variant peptides also inhibited the growth of several other filamentous fungal plant pathogens of *Fusarium* species with the $IC_{50}$ values of 0.5 to 2 µM and the MIC values of 1 to 3 µM (Table 3 and FIG. 4).

TABLE 3

In vitro antifungal activity of NCR2 against *Fusarium* sp.

| Fungi | NCR2 | |
| --- | --- | --- |
| | $IC_{50}$ (µM) | MIC (µM) |
| F. graminearum | 1.5-2 | 3 |
| F. virguliforme | 1.5-2 | 3 |
| F. oxysporum | 0.5 | 0.75-1 |

Figure 5:
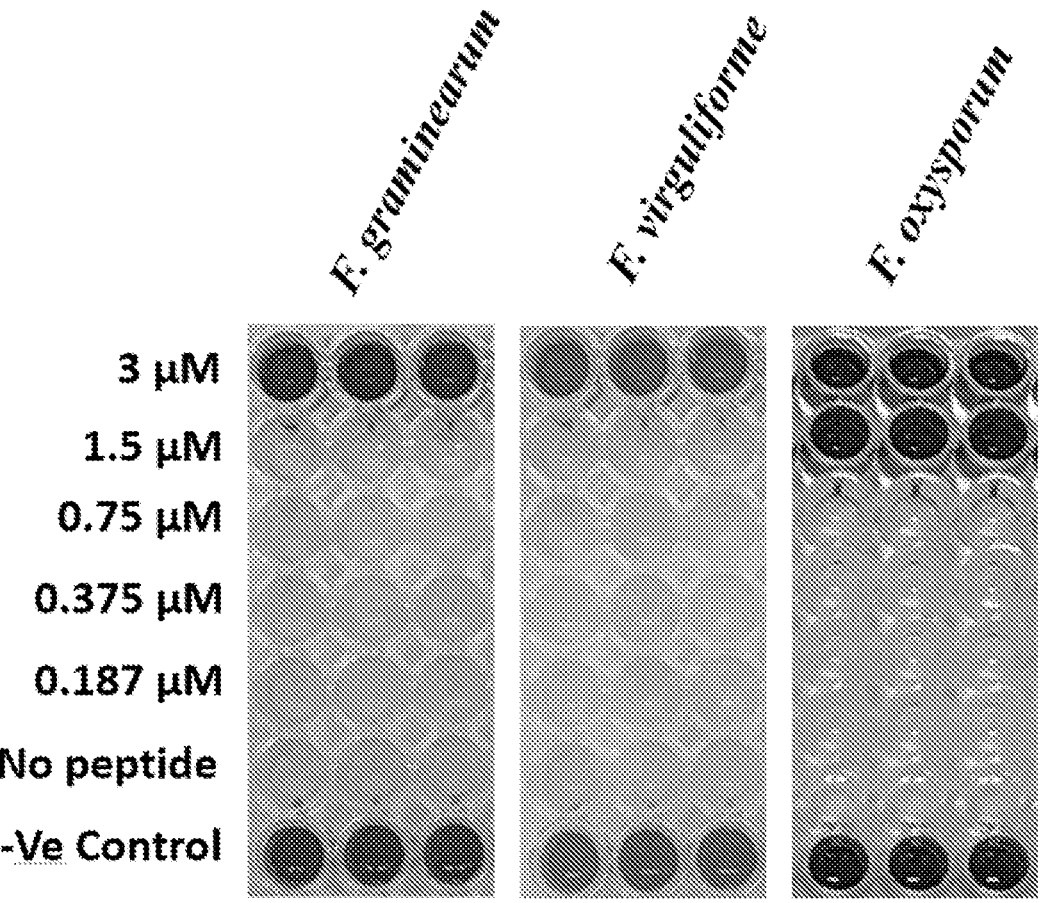
FIG. 5 shows *Fusarium* sp. growth inhibition by wild-type NCR2 (SEQ ID NO: 7) visualized with a fungal cell viability assay using resazurin as a metabolic indicator of living cells.

*F. oxysporum* was most sensitive to NCR2 with MIC value of only 1 µM. The resazurin assay revealed that *F. oxysporum* cells were killed at a concentration of 1.5 µM, whereas the other two fungi were killed at a concentration of 3 µM (FIG. 5).

In Vitro Antifungal Activity of the Dimeric NCR2 Peptides

NCR2-L1-NCR2 (SEQ ID NO: 31) and NCR2-L2-NCR2 (SEQ ID NO: 32) homodimers exhibited very similar antifungal activity against *Fusarium* spp. and *B. cinerea*. Both homodimers showed significant increase in the antifungal activity against *B. cinerea* compared with the antifungal activity of NCR2 monomer. Each dimer inhibited the growth of this fungus with an $IC_{50}$ value of 0.75 µM compared with the $IC_{50}$ value of 1.5 µM for the monomer. Two-fold increase in the antifungal activity against *F. oxysporum, F. graminearum* and *F. virguliforme* was also observed for each dimer compared with the monomer (Table 4).

TABLE 4

In vitro antifungal activity of NCR2 dimers against *Fusarium* sp. and *Botrytis cinerea*

| Fungi | NCR2 | | NCR2-L1-NCR2 APKKVEP (SEQ ID NO: 9) | | NCR2-L2-NCR2 GGKAGKKAPK (SEQ ID NO: 21) | |
| --- | --- | --- | --- | --- | --- | --- |
| | $IC_{50}$ (µM) | MIC (µM) | $IC_{50}$ (µM) | MIC (µM) | $IC_{50}$ (µM) | MIC (µM) |
| Fusarium graminearum | 1.5-2 | 3 | 1 | 1.5 | 1 | 1.5 |
| F. virguliforme | 1.5-2 | 3 | 1 | 1.5 | 1 | 1.5 |
| F. oxysporum | 0.5 | 0.75-1 | 0.3 | 0.75 | 0.3 | 0.75 |
| Botrytis cinerea | 1.5 | 2-3 | 0.75 | 1.5 | 0.75 | 1.5 |

Figure 6:
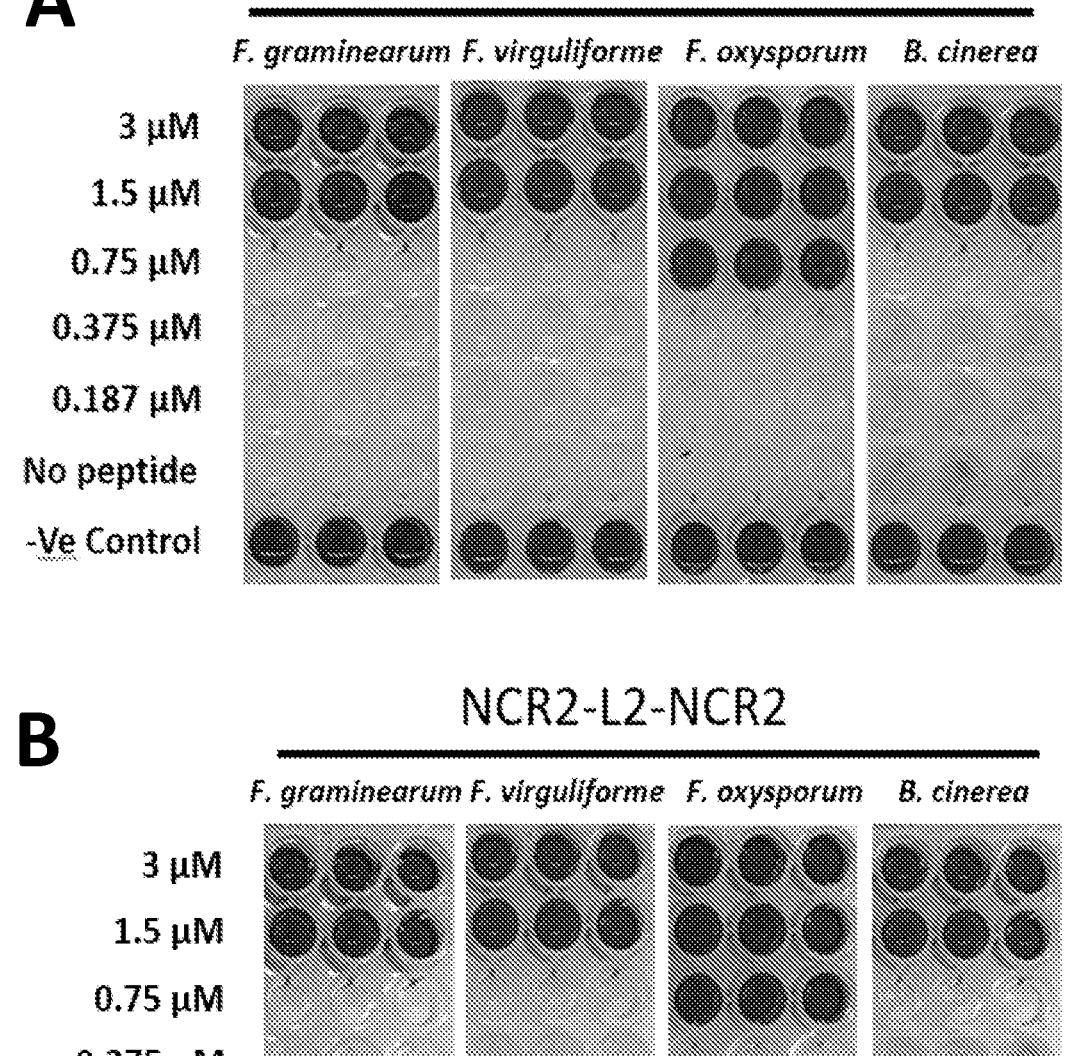
FIG. 6A,B shows *Fusarium* sp. and *B. cinerea* growth inhibition by (A) NCR2-L1-NCR2 (SEQ ID NO: 31) and (B) NCR2-L2-NCR2 (SEQ ID NO: 32) visualized with a fungal cell viability assay using resazurin as a metabolic indicator of living cells.

For each NCR2 homodimer, the resazurin assay revealed complete cell death of *F. graminearum, F. virguliforme* and *B. cinerea* at 1.5 µM and 0.75 µM for *F. oxysporum* (FIG. 6A,B).

In Vitro Anti-Oomycete Activity of NCR2, its Variants and NCR2-L1-NCR2 Homodimer Anti-oomycete activity of the purified NCR2 and its variant peptides against *P. capsici* was determined using the spectrophotometric assay. NCR2 and its variant peptides inhibited the growth of *P. capsici* with the $IC_{50}$ values of 2 to 3 µM and MIC values of 3 to 6 µM (Table 5).

TABLE 5

In vitro antifungal activity of NCR2 and its variants against *Phytophthora capsici*

| Peptide | P. capsici | |
| --- | --- | --- |
| | $IC_{50}$ (µM) | MIC (µM) |
| NCR2 (SEQ ID NO: 7) | 2 | 3 |
| NCR2_V1 (SEQ ID NO: 1) | 2 | 3 |

TABLE 5-continued

In vitro antifungal activity of NCR2 and its variants against *Phytophthora capsici*

| Peptide | P. capsici | |
|---|---|---|
| | IC$_{50}$ (µM) | MIC (µM) |
| NCR2_V2 (SEQ ID NO: 2) | 3 | 6 |
| NCR2-L1-NCR2 | | 3 |
| (SEQ ID 2 NO: 31) | | |

Figure 7:
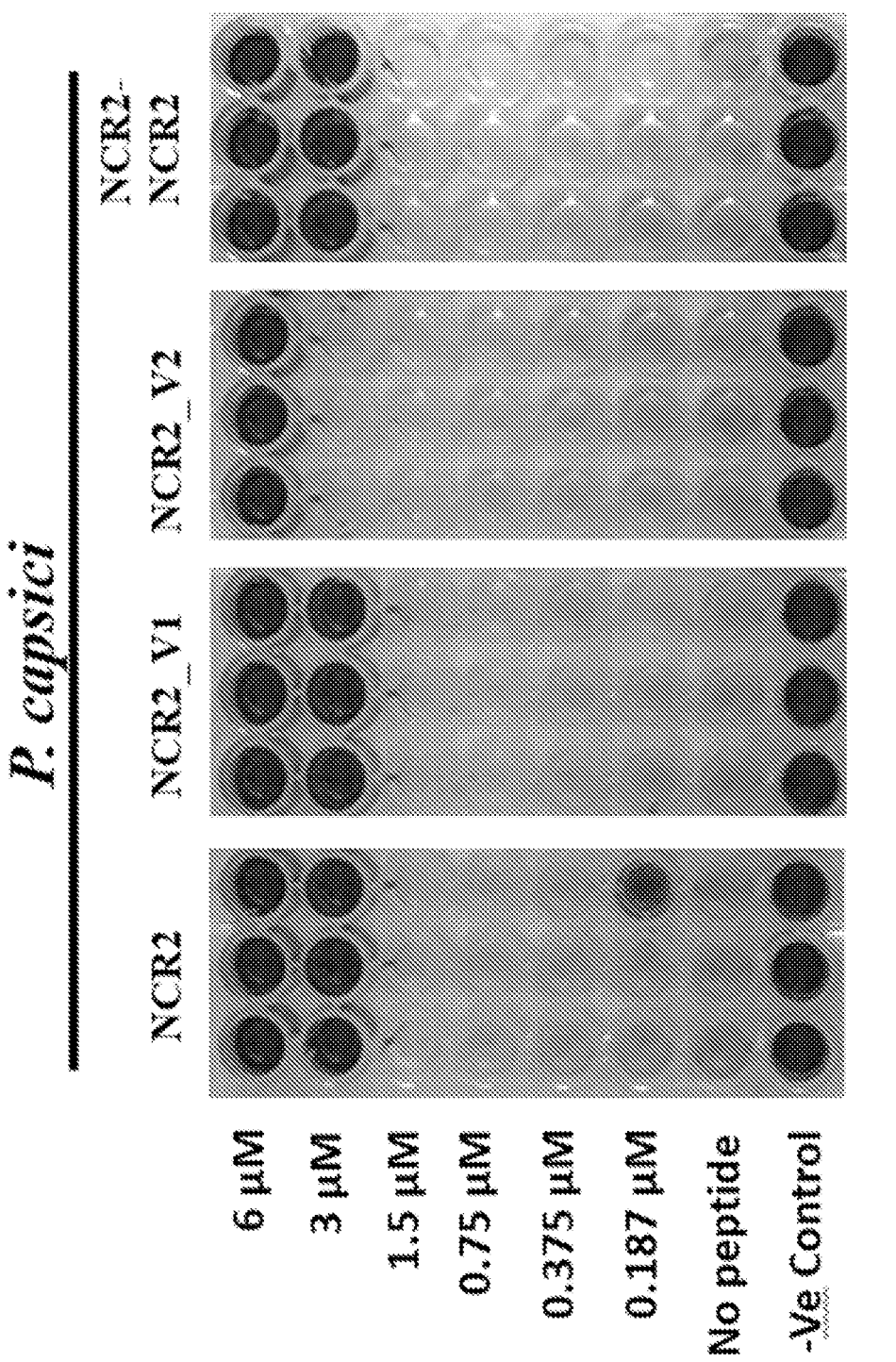
FIG. 7 shows *P. capsici* growth inhibition by NCR2 and its variants visualized with an oomycete cell viability assay using resazurin as a metabolic indicator of living cells.

When compared with the in vitro antioomycete activity of NCR2 monomer, synergistic increase in antioomycete activity of its dimer could not be demonstrated. The resazurin assay revealed cell death of *P. capsici* at 3 µM for NCR2, NCR_V1, NCR2-L1-NCR2, whereas for NCR2_V2 cell death was observed at 6 µM (FIG. 7).

Lettuce—*B. cinerea* Disease Resistance Bioassay of NCR2, NCR2_V1, NCR2_V2 Peptides To demonstrate that the NCR peptides inhibit pathogenic fungi on the surface of plant leaves, lettuce vegetable was drop inoculated with *B. cinerea* that causes grey mold disease. Leaves inoculated with NCR2 displayed smaller lesions compared to no peptide control. Compared with NCR2 treated leaves, NCR2_V1 and NCR2_V2 exhibited much smaller lesions. NCR peptides inhibited the growth of *B. cinerea* in a concentration dependent manner, and the size of lesions decreased with increasing concentrations of NCR peptides (FIG. 1A,B). These results demonstrate the feasibility of topical application of NCR peptides for protecting crops against fungal pathogens.

Phospholipid Binding of NCR2, NCR2V, NCR2V2 Peptides

The ability of NCR2 NCR2_V1, and NCR2_V2 peptides to bind different biologically active phospholipids was assessed using protein-lipid overlay assay. It was found that NCR2 strongly binds to phosphatidylinositol diphosphate (PI(3,5)P$_2$). It also bound weakly to multiple phospholipids, such as phosphatidylinositol monophosphates (PI(3)P, PI(4) P, and PI(5)P), phosphatidylinositol di/tri-phosphates (PI(3, 4)P$_2$, PI(4,5)P$_2$, PI(3,4,5)P$_3$), and phosphatidic acid (PA). NCR2_V1 bound tightly to PI(3)P, PI(4)P, and PI(5)P and weakly to PI(3,4)P$_2$, PI(3,5)P$_2$, PI(4,5)P$_2$ and PA. No binding was observed with NCR2_V1 to PI(3,4,5)P$_3$ when compared with the NCR2 to PI(3,4,5)P$_3$. NCR2_V2 was not found to bind to any phospholipids and the lipid binding was completely abolished (FIG. 2).

Example 2. Biological Sequences and Associated SEQ ID NO

TABLE 6

Biological sequences

| SEQ ID NO. | DESCRIPTION | SEQUENCE | REMARKS |
|---|---|---|---|
| 1 | NCR2_V1 | AFIQLSKPCHKFKGPCSIVKNYRARCRKGY CVRRRIR | |
| 2 | NCR2_V2 | AFCIQLSKPCISDKECSIVKNYRARCRKGYC VRRRIRC | |
| 3 | NCR2_V3 | AFIQLSKPCKRRRDCSIVKNYRARCRKGYC VRRRIR | |
| 4 | NCR2_V4 | AFCIQLSKPCKRRRDCSIVKNYRARCRKGY CVRRRIRC | |
| 5 | NCR2_V5 | AFIQLSKPCKSRKHCSIVKNYRARCRKGYC VRRRIR | |
| 6 | NCR2_V6 | AFCIQLSKPCKSRKHCSIVKNYRARCRKGY CVRRRIRC | |
| 7 | wt NCR2 | AFIQLSKPCISDKECSIVKNYRARCRKGYCV RRRIR | |
| 8 | Defensin Gamma Core consensus | GXCX3-9C | (where X is any amino acid) |
| 9 | MtDef5 spacer peptide | APKKVEP | |
| 10 | MtDef4 (wild-type, H33) | RTCESQSHKFKGPCASDHNCASVCQTERFS GGHCRGFRRRCFCTTHC | |
| 11 | MtDef5-1a | KLCQKRSTTWSGPCLNTGNCKRQCINVEH ATFGACHRQGFGFACFCYKKC | |
| 12 | MtDef5-1b | KLCERRSKTWSGPCLISGNCKRQCINVEHA TSGACHRQGIGFACFCKKKC | |
| 13 | MtDef5 dimer | KLCQKRSTTWSGPCLNTGNCKRQCINVEH ATFGACHRQGFGFACFCYKKCAPKKVEPK LCERRSKTWSGPCLISGNCKRQCINVEHAT SGACHRQGIGFACFCKKKC | |

TABLE 6 -continued

Biological sequences

| SEQ ID NO. | DESCRIPTION | SEQUENCE | REMARKS |
|---|---|---|---|
| 14 | HXL005 | KMCQTTSHAFSCVNDSGCSGSCEKQGFAS GKCDGVRRRCTCYKKC | |
| 15 | HXL008 | KVCTKPSKFFKGLCGTDGACTTACRKEGL HSGYCQLKGFLNSVCVCRKHC | |
| 16 | HXL035 | KVCTKPSKFFKGLCGFDRDCTVACKKEGL ASGFCQNKGFFNVVCVCRKPC | |
| 17 | HXL036 | KVCTKPSKFFKGLCGADRDCTVACKKEGL ATGFCQKKGFFNFVCVCRKPC | |
| 18 | (Gly4Ser)n | GGGGS | |
| 19 | Ser(Gly4Ser)n | SGGGGS | |
| 20 | Spacer Peptide | NNESASPASK | |
| 21 | Spacer Peptide | GGKAGKKAPK | |
| 22 | Spacer Peptide | ATPPTPTPPK | |
| 23 | Spacer Peptide | EPPSLTSTPLN | |
| 24 | Spacer Peptide | GGKPGKKAP | |
| 25 | Spacer Peptide | AGRGDKK | |
| 26 | Spacer Peptide | PPTPPSPPTRP | |
| 27 | Cleavable linker peptide | EEKKN | |
| 28 | Cleavable linker peptide | X.sub.1X.sub.2X.sub.3X.sub.4X.sub.5 where X.sub.1 is E (glu) or D (asp), X.sub.2 is E (glu) or D (asp), X.sub.3 is K (lys) or R (arg), X.sub.4 is K (lys) or R (arg) and X.sub.5 is N (asn) or Q (gln) | |
| 29 | MtDef4 gamma core loop | RGFRRR | |
| 30 | KEX2 cleavage site | KREAEA | Lys84-Arg85- Glu86-Ala87- Glu88-Ala89 |
| 31 | NCR2-L1-NCR2 dimer (with L1 linker peptide underlined) | AFIQLSKPCISDKECSIVKNYRARCRKGYCV RRRIRAPKKVEPAFIQLSKPCISDKECSIVKN YRARCRKGYCVRRRIR | |
| 32 | NCR2-L2-NCR2 dimer (with L2 linker peptide underlined) | AFIQLSKPCISDKECSIVKNYRARCRKGYCV RRRIRGGKAGKKAPKAFIQLSKPCISDKECS IVKNYRARCRKGYCVRRRIR | |
| 33 | NCR2_V2/V4/V6 gamma core peptide | GYCVRRRIRC | |
| 34 | NCR2_V1/V7 sequence between 1st and 2nd cysteine | HKFKGP | |
| 35 | NCR2_wt/V2 sequence between 1st and 2nd cysteine | ISDKE | |
| 36 | NCR2_V3/V4 sequence between 1st and 2nd cysteine | KRRRD | |
| 37 | NCR2_V5/V6 sequence between 1st and 2nd cysteine | KSRKH | |

TABLE 6 -continued

| Biological sequences | | | |
|---|---|---|---|
| SEQ ID NO. | DESCRIPTION | SEQUENCE | REMARKS |
| 38 | Wild type MtDef4 gamma core | GHCRGFRRRC | |
| 39 | C-terminal Core Consensus | GYCX1X2X3X4X5X6X7 | wherein X1 is F, W, I, L, M, or A; wherein X2 is R, K, or H; wherein X3 is R, K, or H; wherein X4 is R, K, or H; wherein X5 is F, W, I, L, M, or A; wherein X6 is R, K, or H; and X7 is C or no amino acid |
| 40 | NCR2_V7 | AFCQLSKPCHKFKGPCSIVKNYRARCRKGY CVRRRIRC | |
| 41 | ER targeting peptide | KDEL | |
| 42 | From NCR13 | QSDKD | |
| 43 | KEX2 protease site | CTCGAGAAAAGA | |
| 44 | XbaI restriction endonuclease site | TAGTAATCTAGA | |
| 45 | wt NCR2 C-terminus | GYCVRRRIRC | |
| 46 | (Gly4)n | GGGG | |
| 47 | MtDef4 H33R variant | RTCESQSHKFKGPCASDHNCASVCQTERFSGGRCRG FRRRCFCTTHC | |
| 48 | Variant MtDef4 gamma core (H33R) | GRCRGFRRRC | |
| 49 | NCR2 (wild-type) encoding DNA | GCTTTTATTCAATTGTCTAAGCCATGTATCTCTGAT AAGGAATGTTCTATCGTTAAGAACTACAGAGCTAG ATGTAGAAAAGGTTATTGTGTTAGAAGAAGAATTA GA | |
| 50 | NCR2-L1-NCR2 encoding DNA | GCCTTCATTCAGTTGTCCAAGCCATGTATTAGT GATAAAGAGTGTTCAATCGTCAAGAATTACAG AGCCAGATGCAGAAAAGGTTACTGTGTTAGAA GAAGAATTAGAGCTCCAAAGAAAGTTGAACCT GCTTTTATTCAATTGTCTAAGCCATGTATCTCT GATAAAGAGTGTTCTATCGTCAAGAACTACAG AGCAAGATGCAGAAAAGGTTATTGTGTCAGAA GAAGAATCAGA | |
| 51 | NCR2-L2-NCR2 encoding DNA | GCTTTTATTCAATTGTCTAAGCCATGTATCTCTGAT AAGGAATGTTCTATCGTTAAGAACTACAGAGCTAG ATGTAGAAAGGGTTATTGTGTTAGAAGAAGAATTA GAGGTGGTAAAGCTGGTAAAAAGGCTCCAAAAGC TTTCATTCAATTGTCTAAGCCTTGTATCTCTGATAA GGAGTGTTCTATCGTTAAAAATTATAGAGCTAGAT GCAGAAAAGGATACTGCGTCAGAAGAAGAATTAG A | |
| 52 | NCR2_V1 encoding DNA | GCTTTTATTCAATTGTCTAAGCCATGTCATAAGTTC AAAGGTCCTTGTTCTATTGTTAAGAACTACAGAGCT AGATGTAGAAAAGGTTATTGTGTTAGAAGAAGAAT TAGA | |

TABLE 6 -continued

Biological sequences

| SEQ ID NO. | DESCRIPTION | SEQUENCE | REMARKS |
|---|---|---|---|
| 53 | NCR2_V2 encoding DNA | GCTTTCTGTATCCAATTGTCTAAGCCATGTATCTCT GATAAGGAATGTTCTATCGTTAAGAACTACAGAGC TAGATGTAGAAAGGGTTACTGTGTTAGAAGAAGA ATTAGATGT | |

The breadth and scope of the present disclosure should not be limited by any of the above-described examples.

EMBODIMENTS

The following numbered embodiments form part of the disclosure:

1. A recombinant polynucleotide comprising a first polynucleotide encoding a first antimicrobial peptide, wherein the first antimicrobial peptide comprises:
(i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or
(ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7;
optionally wherein the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or optionally wherein the first antimicrobial peptide comprises a C-terminal amino acid sequence of SEQ ID NO: 8 or SEQ ID NO: 39.

2. The recombinant polynucleotide of embodiment 1, wherein the first antimicrobial peptide comprises the amino acid sequence of SEQ ID NO: 1.

3. The recombinant polynucleotide of embodiment 1, wherein the first antimicrobial peptide comprises an amino acid sequence selected from the group consisting of SEQ ID NO: 2, SEQ ID NO: 3, SEQ ID NO: 4, SEQ ID NO: 5, and SEQ ID NO: 6.

4. A recombinant polynucleotide comprising a first polynucleotide encoding a first antimicrobial peptide linked by a spacer peptide to a second antimicrobial peptide, wherein the first and second antimicrobial peptides each comprise one of:
(i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or
(ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40;

optionally wherein the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or
optionally wherein the first or second antimicrobial peptide comprises a C-terminal amino acid sequence of SEQ ID NO: 8 or SEQ ID NO: 39.

5. The recombinant polynucleotide of embodiment 4, wherein at least one of the first or second antimicrobial peptide comprises SEQ ID NO: 1 or SEQ ID NO: 7, or wherein the first polynucleotide encodes a sequence having at least 70%, 80%, 85%, 90%, 92%, 95%, 97%, 98%, 99%, or 100% sequence identity across the entire length of SEQ ID NO: 31 or SEQ ID NO: 32 or a variant thereof wherein one or more of the hydrophobic, basic, and/or acidic amino acid residues are substituted with hydrophobic, basic, and/or acidic amino acid residues, respectively.

6. The recombinant polynucleotide of embodiment 4 or 5, wherein the second antimicrobial peptide has an amino acid sequence that is not identical to the first antimicrobial peptide 7. The recombinant polynucleotide of embodiment 4 or 5, wherein the second antimicrobial peptide has an amino acid sequence that is identical to the first antimicrobial peptide.

8. The recombinant polynucleotide of embodiment 7, wherein the first and second antimicrobial peptide both comprise SEQ ID NO: 7.

9. The recombinant polynucleotide of embodiment 8, wherein the polynucleotide encodes SEQ ID NO: 31 or SEQ ID NO: 32.

10. The recombinant polynucleotide of any one of embodiments 1 to 9, wherein the first polynucleotide is operably linked to a second polynucleotide comprising a promoter which is heterologous to the first polynucleotide.

11. The recombinant polynucleotide of any one of embodiments 1 to 10, wherein the first or second antimicrobial peptide contains at least thirteen, twelve, eleven, ten, nine, eight, seven, or six of the basic amino acid residues set forth in SEQ ID NO: 1 or a basic amino acid substitution thereof.

12. The recombinant polynucleotide of embodiment 11, wherein the first or second antimicrobial peptide contains at least thirteen, twelve, eleven, ten, nine, eight, seven, or six of the basic amino acid residues set forth in SEQ ID NO: 1.

13. The recombinant polynucleotide of any one of embodiments 1 to 12, wherein the first or second antimicrobial peptide contains at least ten, nine, eight, seven, or six of the hydrophobic amino acid residues set forth in SEQ ID NO: 1 or a hydrophobic amino acid substitution thereof.

14. The recombinant polynucleotide of embodiment 13, wherein the first or second antimicrobial peptide contains at least ten, nine, eight, seven, or six of the hydrophobic amino acid residues set forth in SEQ ID NO: 1.

15. The recombinant polynucleotide of any one of embodiments 1 to 14, wherein:

the first or second antimicrobial peptide has a net positive charge of at least about +9; or the first or second antimicrobial peptide has a net positive charge of at least about +9 to about +13.

16. The recombinant polynucleotide of any one of embodiments 1 to 15, wherein:

the amino acid sequence of the first or second antimicrobial polypeptide comprises at least 30% or at least 35% of hydrophobic amino acids; or the amino acid sequence of the first or second antimicrobial polypeptide comprises between 30% and 40% or between 35% and 40% of hydrophobic amino acids.

17. The recombinant polynucleotide of any one of embodiments 1 to 16, wherein the first or second antimicrobial polypeptide comprises a C-terminus cysteine residue that forms a disulfide bond with another cysteine residue of the polypeptide.

18. The recombinant polynucleotide of any one of embodiments 1 to 17, wherein;

the first or second antimicrobial polypeptide comprises a defensin gamma core consensus sequence (SEQ ID NO: 8); the first or second antimicrobial polypeptide comprises the amino acid sequence of SEQ ID NO: 33; or the first or second antimicrobial polypeptide comprises the amino acid sequence of SEQ ID NO: 39.

19. The recombinant polynucleotide of any one of embodiments 1 to 18, wherein the recombinant polynucleotide further comprises a polynucleotide encoding (i) a transit peptide, a vacuolar targeting peptide, and/or an endoplasmic reticulum targeting peptide; (ii) a plastid targeting peptide; and/or (iii) a polyadenylation or transcriptional termination signal, wherein the polynucleotides of (i), (ii), and/or (iii) are operably linked to the first polynucleotide encoding the first or first and second antimicrobial peptide(s).

20. The recombinant polynucleotide of any one of embodiments 10 to 19, wherein the promoter provides for expression of the first or first and second antimicrobial peptide(s) in a plant, yeast, mammalian, or bacterial cell when the polynucleotide is located in the plant, yeast, mammalian, or bacterial cell.

21. The recombinant polynucleotide of any one of embodiments 1 to 20, wherein the first polynucleotide encoding the first or first and second antimicrobial peptide(s) is inserted into a heterologous nuclear or plastid genome of a cell and operably linked to an endogenous promoter located in the heterologous nuclear or plastid genome.

22. The recombinant polynucleotide of embodiment 21, wherein the heterologous nuclear or plastid genome is a monocot crop plant or a dicot crop plant nuclear or plastid genome.

23. The recombinant polynucleotide of embodiment 22, wherein said dicot crop plant nuclear or plastid genome is not a chickpea plant nuclear or plastid genome.

24. The recombinant polynucleotide of embodiment 22, wherein the monocot crop plant nuclear or plastid genome is selected from the group consisting of a corn, barley, oat, pearl millet, rice, sorghum, sugarcane, turf grass, and wheat plant nuclear or plastid genome.

25. The recombinant polynucleotide of embodiment 22, wherein the dicot crop plant nuclear or plastid genome is selected from the group consisting of alfalfa, a *Brassica* sp., cotton, potato, sugar beet, and soybean nuclear or plastid genome.

26. The recombinant polynucleotide of embodiment 22, wherein the dicot crop plant nuclear or plastid genome is selected from the group consisting of an apple, cucurbit, strawberry, and tomato nuclear or plastid genome.

27. The recombinant polynucleotide of any one of embodiments 1 to 3, wherein;

the polynucleotide encoding the first antimicrobial peptide further comprises a polynucleotide encoding a second antimicrobial peptide, wherein the second antimicrobial peptide is optionally a defensin or NCR peptide; optionally wherein the defensin comprises an antimicrobial peptide having at least 85%, 90%, 92%, 95%, 97%, 98%, 99%, or 100% sequence identity across the entire length of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 47; and/or optionally wherein the polynucleotides encoding the first and second antimicrobial peptide are operably linked by a polynucleotide encoding a spacer peptide.

28. The recombinant polynucleotide of any one of embodiments 4 to 27, wherein the spacer peptide comprises the amino acid sequence of SEQ ID NO: 9 or 18-28, or a variant of any one of the amino acids sequences of SEQ ID NO: 9 or 18-28, having 1, 2, or 3 conservative amino acid substitutions; optionally wherein the spacer peptide comprises or consists of APKKVEP (SEQ ID NO: 9) or GGK-AGKKAPK (SEQ ID NO: 21).

29. An edited polynucleotide comprising a variant polynucleotide encoding a first antimicrobial peptide, wherein the first antimicrobial peptide comprises:

(i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7, wherein said variant polynucleotide is operably linked to a polynucleotide comprising a promoter, wherein the variant polynucleotide comprises at least one nucleotide insertion, deletion, and/or substitution in comparison to the corresponding unedited wild type polynucleotide sequence;

optionally wherein the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or optionally wherein the first antimicrobial peptide comprises a C-terminal amino acid sequence of SEQ ID NO: 8 or SEQ ID NO: 39; and optionally wherein the corresponding unedited wild type polynucleotide sequence encodes the antimicrobial peptide comprising the amino acid sequence of SEQ ID NO: 7.

30. A plant nuclear or plastid genome comprising a first polynucleotide encoding a first antimicrobial peptide, wherein the first antimicrobial peptide comprises:

(i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7, wherein the polynucleotide is heterologous to the nuclear or plastid genome and operably linked to an endogenous promoter of the nuclear or plastid genome;

optionally wherein the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or optionally wherein the first antimicrobial peptide comprises a C-terminal amino acid sequence of SEQ ID NO: 8 or SEQ ID NO: 39.

31. The edited polynucleotide of embodiment 29, or the nuclear or plastid genome of embodiment 30, wherein the first antimicrobial peptide comprises the amino acid sequence of SEQ ID NO: 1.

32. The edited polynucleotide of embodiment 29, or the nuclear or plastid genome of embodiment 30, wherein the first antimicrobial peptide comprises an amino acid sequence selected from the group consisting of SEQ ID NO: 2, SEQ ID NO: 3, SEQ ID NO: 4, SEQ ID NO: 5, and SEQ ID NO: 6.

33. The edited polynucleotide or genome of any one of embodiments 29 to 32, wherein the polynucleotide encoding the first antimicrobial peptide further encodes a second antimicrobial peptide, wherein the second antimicrobial peptide is optionally a defensin or NCR peptide; or optionally wherein the defensin comprises an antimicrobial peptide having at least 85%, 90%, 92%, 95%, 97%, 98%, 99%, or 100% sequence identity across the entire length of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 47.

34. An edited polynucleotide comprising a variant polynucleotide encoding a first antimicrobial peptide linked by a spacer peptide to a second antimicrobial peptide, wherein the first and second antimicrobial peptides each comprises one of:

(i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40;

wherein said variant polynucleotide is operably linked to a polynucleotide comprising a promoter, wherein the variant polynucleotide comprises at least one nucleotide insertion, deletion, and/or substitution in comparison to the corresponding unedited wild type polynucleotide sequence;

optionally wherein the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or optionally wherein the first or second antimicrobial peptide comprises a C-terminal amino acid sequence of SEQ ID NO: 8 or SEQ ID NO: 39; and optionally wherein the corresponding unedited wild type polynucleotide sequence encodes the antimicrobial peptide comprising the amino acid sequence of SEQ ID NO: 7.

35. A plant nuclear or plastid genome comprising a first polynucleotide encoding a first antimicrobial peptide linked by a spacer peptide to a second antimicrobial peptide, wherein the first and second antimicrobial peptide each comprise one of:

(i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40; wherein the polynucleotide is heterologous to the nuclear or plastid genome and operably linked to an endogenous promoter of the nuclear or plastid genome;

optionally wherein the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1 and/or optionally wherein the first or second antimicrobial peptide comprises a C-terminal amino acid sequence of SEQ ID NO: 8 or SEQ ID NO: 39.

36. The edited polynucleotide of embodiment 34, or the nuclear or plastid genome of embodiment 35, wherein at least one of the first or second antimicrobial peptide comprises SEQ ID NO: 1 or SEQ ID NO: 7 or wherein the first polynucleotide encodes a sequence having at least 70%, 80%, 85%, 90%, 92%, 95%, 97%, 98%, 99%, or 100% sequence identity across the entire length of SEQ ID NO: 31 or SEQ ID NO: 32 or a variant thereof wherein one or more of the hydrophobic, basic, and/or acidic amino acid residues are substituted with hydrophobic, basic, and/or acidic amino acid residues, respectively.

37. The edited polynucleotide or genome of any one of embodiments 34 to 36, wherein the second antimicrobial peptide has an amino acid sequence that is not identical to the first antimicrobial peptide.

38. The edited polynucleotide or genome of any one of embodiments 34 to 36, wherein the second antimicrobial peptide has an amino acid sequence that is identical to the first antimicrobial peptide.

39. The edited polynucleotide or genome of embodiment 38, wherein the first and second antimicrobial peptide both comprise SEQ ID NO: 7; optionally wherein the polynucleotide encodes SEQ ID NO: 31 or SEQ ID NO: 32.

40. The edited polynucleotide or genome of any one of embodiments 29 to 39, wherein the first or second antimicrobial peptide contains at least thirteen, twelve, eleven, ten, nine, eight, seven, or six of the basic amino acid residues set forth in SEQ ID NO: 1 or a basic amino substitution thereof; optionally wherein the first or second antimicrobial peptide contains at least thirteen, twelve, eleven, ten, nine, eight, seven, or six of the basic amino acid residues set forth in SEQ ID NO: 1.

41. The edited polynucleotide or genome of any one of embodiments 29 to 40, wherein the first or second antimicrobial peptide contains at least ten, nine, eight, seven, or six of the hydrophobic amino acid residues set forth in SEQ ID NO: 1 or a hydrophobic amino acid substitution thereof; optionally wherein the first or second antimicrobial peptide contains at least ten, nine, eight, seven, or six of the hydrophobic amino acid residues set forth in SEQ ID NO: 1.

42. The edited polynucleotide or genome of any one of embodiments 29 to 41, further comprising a polynucleotide encoding (i) a transit peptide, a vacuolar targeting peptide, and/or an endoplasmic reticulum targeting peptide; (ii) a plastid targeting peptide; and/or (iii) a polyadenylation or transcriptional termination signal, wherein the polynucleotides of (i), (ii), and/or (iii) are operably linked to the polynucleotide encoding the first or first and second antimicrobial peptide(s).

43. The edited polynucleotide or genome of any one of embodiments 29 to 42, wherein the polynucleotide comprising the promoter contains at least one nucleotide insertion, deletion, and/or substitution in comparison to the corresponding wild type polynucleotide sequence.

44. The edited polynucleotide or genome of any one of embodiments 29 to 43, wherein the polynucleotide encoding the first or first and second antimicrobial peptide(s) is integrated into the nuclear or plastid genome of a cell.

45. The edited polynucleotide or genome of any one of embodiments 29 to 44, wherein the nuclear or plastid genome is a monocot crop plant or a dicot crop plant nuclear or plastid genome.

46. The edited polynucleotide or genome of embodiment 45, wherein said dicot crop plant nuclear genome is not a chickpea plant nuclear genome.

47. The edited polynucleotide or genome of embodiment 45, wherein the monocot crop plant nuclear or plastid genome is selected from the group consisting of a corn, barley, oat, pearl millet, rice, sorghum, sugarcane, turf grass, and wheat plant nuclear or plastid genome.

48. The edited polynucleotide or genome of embodiment 45, wherein the dicot crop plant nuclear or plastid genome is selected from the group consisting of alfalfa, a *Brassica* sp., cotton, potato, sugar beet, and soybean nuclear or plastid genome.

49. The edited polynucleotide or genome of embodiment 45, wherein the dicot crop plant nuclear or plastid genome is selected from the group consisting of an apple, cucurbit, strawberry, and tomato nuclear or plastid genome.

50. The edited polynucleotide or genome of any one of embodiments 33 to 49, wherein the polynucleotides encoding the first and second antimicrobial peptide are operably linked by a polynucleotide encoding a spacer peptide.

51. The edited polynucleotide or genome of embodiment 50, wherein the spacer peptide comprises the amino acid sequence of SEQ ID NO: 9 or 18-28, or a variant of any one of the amino acids sequences of SEQ ID NO: 9 or 18-28, having 1, 2, or 3 conservative amino acid substitutions; optionally wherein the spacer peptide comprises or consists of APKKVEP (SEQ ID NO: 9) or GGKAGKKAPK (SEQ ID NO: 21).

52. A cell comprising the recombinant polynucleotide of any one of embodiments 1 to 28 or the edited polynucleotide or genome of any one of embodiments 29 to 51.

53. The cell of embodiment 52, wherein the cell is a plant, yeast, mammalian, or bacterial cell.

54. The cell of embodiment 53, wherein the cell is a plant cell that is non-regenerable.

55. A plant comprising the recombinant polynucleotide of any one of embodiments 1 to 28 or the edited polynucleotide or genome of any one of embodiments 29 to 51.

56. The plant of embodiment 55, wherein said plant or any part thereof contains a plant pathogenic microbe inhibitory concentration of the antimicrobial protein.

57. The plant of embodiment 55 or 56, wherein the plant pathogenic microbe inhibitory concentration of the antimicrobial protein is at least 0.005, 0.05, 0.5, or 1 (parts per million) PPM in a tissue or part of the plant.

58. The plant of any one of embodiments 55 to 57, wherein the recombinant nucleic acid molecule, edited polynucleotide, or genome confers to the plant resistance to infection by a plant pathogenic microbe in comparison to a control plant that lacks the recombinant nucleic acid molecule edited polynucleotide, or genome.

59. The plant of embodiment 58, wherein the plant pathogenic microbe is a *Fusarium* sp., *Alternaria* sp., *Verticillium* sp., *Phytophthora* sp., *Colletotrichum* sp., *Botrytis* sp., *Cercospora* sp., *Phakopsora* sp. *Rhizoctonia* sp., *Sclerotinia* sp., *Pythium* sp., *Phoma* sp., *Gaeumannomces* sp. *Leptoshaeria* sp., or *Puccinia* sp.

60. The plant of any one of embodiments 55 to 59, wherein the plant is a monocot crop plant or a dicot crop plant.

61. The plant of embodiment 60, wherein said dicot crop plant is not a chickpea plant.

62. The plant of embodiment 60, wherein the monocot crop plant is selected from the group consisting of a corn, barley, oat, pearl millet, rice, sorghum, sugarcane, turf grass, and wheat plant.

63. The plant of embodiment 60, wherein the dicot crop plant is selected from the group consisting of alfalfa, a *Brassica* sp., cotton, cucurbit, potato, strawberry, sugar beet, soybean, and tomato.

64. A plant part of the plant of any one of embodiments 55 to 63, where the plant part comprises the recombinant polynucleotide, edited polynucleotide, or genome.

65. The plant part of embodiment 64, wherein the plant part is a seed, stem, leaf, root, tuber, flower, or fruit.

66. A processed plant product of the plant part of embodiment 64 or 65, wherein the processed plant product comprises the recombinant nucleic acid, the edited polynucleotide, or a fragment thereof.

67. The processed plant product of embodiment 66, wherein the product is non-regenerable.

68. The processed plant product of embodiments 66 or 67, wherein the product is a meal or flour.

69. The processed plant product of any one of embodiments 66 to 68, wherein the fragment comprises a recombinant polynucleotide encoding a junction of the polynucleotide encoding the first antimicrobial peptide with the polynucleotide comprising the promoter which is heterologous to the polynucleotide encoding the first antimicrobial peptide.

70. The processed plant product of any one of embodiments 66 to 69, wherein the fragment comprises an edited polynucleotide which is heterologous to the genome of the plant from which the product was obtained.

71. The processed plant product of any one of embodiments 66 to 70, wherein the processed plant product is characterized by having reduced levels of microbial toxins in comparison to processed plant products obtained from corresponding control plant crops.

72. A method for obtaining a plant comprising the recombinant polynucleotide of any one of embodiments 1 to 28 or plant nuclear or plastid genome of any one of embodiments 29 to 51 that is resistant to infection by a plant pathogenic microbe comprising the steps of: (i) introducing the recombinant polynucleotide, the polynucleotide encoding the antimicrobial peptide, the polynucleotide comprising the promoter, a fragment of said polynucleotides, or a combination of said polynucleotides into a plant cell, tissue, plant part, or whole plant; (ii) obtaining a plant cell, tissue, part, or whole plant wherein the recombinant polynucleotide, the polynucleotide encoding the antimicrobial peptide, the polynucleotide comprising the promoter, a fragment of said polynucleotides, or a combination of said polynucleotides has integrated into the plant nuclear or plastid genome; and (iii) selecting a plant obtained from the plant cell, tissue, part or whole plant of step (ii) for expression of a plant pathogenic microbe inhibitory amount of the first antimicrobial peptide, thereby obtaining a plant that is resistant to infection by a plant pathogenic microbe.

73. The method of embodiment 72, wherein the recombinant polynucleotide is introduced into the plant cell, tissue, part, or whole plant by *Agrobacterium*-, electroporation-, transfection-, or particle-mediated transformation.

74. The method of embodiment 73 or 74, wherein the recombinant polynucleotide, the polynucleotide encoding the antimicrobial peptide, the polynucleotide comprising the promoter, a fragment of said polynucleotides, or a combination of said polynucleotides is introduced in step (i) with: (a) a clustered regularly interspaced short palindromic repeats (CRISPR)-associated (Cas)-guide RNA or source thereof and a Cas endonuclease or source thereof, wherein the guide RNA and Cas endonuclease can form a complex that can introduce a double strand break at a target site in a nuclear genome of the plant cell, tissue, part, or whole plant; and (b) a template polynucleotide comprising the recombinant polynucleotide, the polynucleotide encoding the antimicrobial peptide, the polynucleotide comprising the promoter, a fragment of said polynucleotides, or a combination of said polynucleotides.

75. The method of any one of embodiments 73 to 75, wherein said template comprises sequences at its 5' and 3' terminus with sequence identity to sequences on both sides of the double strand break that permit integration of the template by homologous recombination.

76. The method of any one of embodiments 73 to 76, wherein the recombinant nucleic acid molecule is introduced in step (i) with: (a) an endonuclease or an endonuclease and a guide RNA, wherein the endonuclease or the endonuclease and guide RNA can form a complex that can introduce a double strand break at a target site in a nuclear genome of the plant cell, tissue, part, or whole plant; and (b) a template polynucleotide comprising the recombinant polynucleotide, the polynucleotide encoding the antimicrobial peptide, the polynucleotide comprising the promoter, a fragment of said polynucleotides, or a combination of said polynucleotides.

77. A method for obtaining a plant comprising the edited polynucleotide or genome of any one of embodiments 29 to 51 that is resistant to infection by a plant pathogenic microbe comprising the steps of: (i) providing: (a) a template polynucleotide comprising the polynucleotide encoding the antimicrobial peptide or a fragment thereof; and (b) an endonuclease or an endonuclease and a guide RNA to a plant cell, tissue, part, or whole plant, wherein the endonuclease or guide RNA and endonuclease can form a complex that can introduce a double strand break at a target site in a nuclear or plastid genome of the plant cell, tissue, part, or whole plant; (ii) obtaining a plant cell, tissue, part, or whole plant wherein at least one nucleotide insertion, deletion, and/or substitution has been introduced into the corresponding wild type polynucleotide sequence; and (iii) selecting a plant obtained from the plant cell, tissue, part or whole plant of step (ii) comprising the edited polynucleotide for expression of a plant pathogenic microbe inhibitory amount of the first antimicrobial peptide, thereby obtaining a plant that is resistant to infection by a plant pathogenic microbe.

78. The method of embodiment 77, further comprising the step of introducing at least one nucleotide insertion, deletion, and/or substitution in the promoter that is operably linked to variant polynucleotide encoding the first antimicrobial peptide.

79. The method of embodiments 77 or 78, wherein the endonuclease is a Cas endonuclease and the guide RNA is a clustered regularly interspaced short palindromic repeats (CRISPR)-associated (Cas)-guide RNA.

80. The method of any one of embodiments 77 to 79, wherein the Cas endonuclease is a Cas9 or Cpf1 endonuclease.

81. A method for producing plant seed that provide plants resistant to infection by a plant pathogenic microbe that comprises the steps of: (i) selfing or crossing the plant of any one of embodiments 55 to 63; and (ii) harvesting seed that comprises the recombinant polynucleotide of the plant from the self or cross, thereby producing plant seed that provide plants resistant to infection by a plant pathogenic microbe.

82. The method of embodiment 81, wherein the plant is used as a pollen donor in the cross and the seed are harvested from a pollen recipient.

83. A method for preventing or reducing crop damage by a plant pathogenic microbe comprising the steps of: (i) placing seeds or cuttings of the plants of any one of embodiments 55 to 63 in a field where control plants are susceptible to infection by at least one plant pathogenic microbe; and (ii) cultivating a crop of plants from the seeds or cuttings, thereby reducing crop damage by the plant pathogenic microbe.

84. The method of embodiment 83, wherein the method further comprises the step of harvesting seed, fruit, leaves, tubers, stems, roots, or any combination thereof from the crop.

85. The method of embodiments 83 or 84, wherein said seed, fruit, leaves, tubers, stems, roots, or any combination thereof have reduced levels of microbial toxins in comparison to seed, fruit, leaves, tubers, stems, roots, or any combination thereof obtained from corresponding control plant crops.

86. A composition comprising a first antimicrobial peptide comprising:

(i) the amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively, and wherein the amino acid sequence does not comprise SEQ ID NO: 7; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, or 40, wherein the amino acid sequence does not comprise SEQ ID NO: 7;

and an agriculturally, pharmaceutically, or veterinarily acceptable carrier, diluent, or excipient; optionally wherein the first antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or optionally wherein the first antimicrobial peptide comprises a C-terminal amino acid sequence of SEQ ID NO: 8 or SEQ ID NO: 39.

87. The composition of embodiment 86, wherein the first antimicrobial peptide comprises the amino acid sequence of SEQ ID NO: 1.

88. The composition of embodiment 1, wherein the first antimicrobial peptide comprises an amino acid sequence selected from the group consisting of SEQ ID NO: 2, SEQ ID NO: 3, SEQ ID NO: 4, SEQ ID NO: 5, and SEQ ID NO: 6.

89. The composition of any one of embodiments 86 to 88, wherein the polynucleotide encoding the first antimicrobial peptide further encodes a second antimicrobial peptide, wherein the second antimicrobial peptide is optionally a defensin or an NCR peptide; optionally wherein the defensin comprises an antimicrobial peptide having at least 85%, 90%, 92%, 95%, 97%, 98%, 99%, or 100% sequence identity across the entire length of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 47; and/or optionally wherein the polynucleotides encoding the first and second antimicrobial peptide are operably linked by a polynucleotide encoding a spacer peptide.

90. The composition of any one of embodiments 86 to 89, wherein the first antimicrobial peptide comprises:

(i) an amino acid sequence having at least 85%, 90%, 92%, 95%, 97%, 98%, or 99% sequence identity to SEQ ID NO: 1, 2, 3, 4, 5, or 6, wherein one or more of the hydrophobic, basic, and/or acidic amino acid residues of SEQ ID NO: 1, 2, 3, 4, 5, or 6 are substituted with hydrophobic, basic, and/or acidic amino acid residues, respectively, and wherein the amino acid sequence does not comprise SEQ ID NO: 7; or (ii) a chemically modified peptide comprising an amino acid sequence of SEQ ID NO: 1, 2, 3, 4, 5, 6, 40, or a variant thereof wherein one or more of the hydrophobic, basic, and/or acidic amino acid residues are substituted with hydrophobic, basic, and/or acidic amino acid residues, respectively; or an amino acid sequence having at least 60%, 70%, 80%, 85%, 90%, 92%, 95%, 97%, 98%, 99%, or 100% sequence identity to SEQ ID NO: 1, 2, 3, 4, 5, or 6, wherein said chemically modified peptide comprises at least one non-naturally occurring amino acid residue.

91. A composition comprising a first antimicrobial peptide linked by a spacer peptide to a second antimicrobial peptide, wherein the first and second antimicrobial peptides each comprise one of:

(i) the amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or (ii) an amino acid sequence having at least 60%, 70%, 80%, 85%, 90%, 92%, 95%, 97%, 98%, 99%, or 100% sequence identity across the entire length of SEQ ID NO: 1, 2, 3, 4, 5, 6, 7, or 40;

and an agriculturally, pharmaceutically, or veterinarily acceptable carrier, diluent, or excipient; optionally wherein the first or second antimicrobial peptide comprises the amino acid sequence of HKFKGP (SEQ ID NO: 34), ISDKE (SEQ ID NO: 35), KRRRD (SEQ ID NO: 36), or KSRKH (SEQ ID NO: 37) at a position corresponding to between the first and second cysteine residues of SEQ ID NO: 1; and/or optionally wherein the first or second antimicrobial peptide comprises a C-terminal amino acid sequence of SEQ ID NO: 8 or SEQ ID NO: 39.

92. The composition of embodiment 91, wherein at least one of the first or second antimicrobial peptide comprises SEQ ID NO: 1 or SEQ ID NO: 7 or wherein the first polynucleotide encodes a sequence having at least 70%, 80%, 85%, 90%, 92%, 95%, 97%, 98%, 99%, or 100% sequence identity across the entire length of SEQ ID NO: 31 or SEQ ID NO: 32 or a variant thereof wherein one or more of the hydrophobic, basic, and/or acidic amino acid residues are substituted with hydrophobic, basic, and/or acidic amino acid residues, respectively.

93. The composition of embodiment 91 or 92, wherein the second antimicrobial peptide has an amino acid sequence that is not identical to the first antimicrobial peptide.

94. The composition of embodiment 91 or 92, wherein the second antimicrobial peptide has an amino acid sequence that is identical to the first antimicrobial peptide.

95. The composition of embodiment 94, wherein the first and second antimicrobial peptide both comprise SEQ ID NO: 7.

96. The composition of embodiment 95, wherein the polynucleotide encodes SEQ ID NO: 31 or SEQ ID NO: 32.

97. The composition of any one of embodiments 91 to 96, wherein the first or second antimicrobial peptide comprises:

(i) an amino acid sequence having at least 85%, 90%, 92%, 95%, 97%, 98%, or 99% sequence identity to SEQ ID NO: 1, 2, 3, 4, 5, 6, 7, or 40 wherein one or more of the hydrophobic, basic, and/or acidic amino acid residues of SEQ ID NO: 1, 2, 3, 4, 5, 6, 7, or 40 are substituted with hydrophobic, basic, and/or acidic amino acid residues, respectively; or (ii) a chemically modified peptide comprising an amino acid sequence of SEQ ID NO: 1, 2, 3, 4, 5, 6, 7, 40, or a variant thereof wherein one or more of the hydrophobic, basic, and/or acidic amino acid residues are substituted with hydrophobic, basic, and/or acidic amino acid residues, respectively; or an amino acid sequence having at least 60%, 70%, 80%, 85%, 90%, 92%, 95%, 97%, 98%, 99%, or 100% sequence identity to SEQ ID NO: 1, 2, 3, 4, 5, 6, 7, or 40 wherein said chemically modified peptide comprises at least one non-naturally occurring amino acid residue.

98. The composition of any one of embodiments 86 to 97, wherein the first or second antimicrobial peptide contains at least thirteen, twelve, eleven, ten, nine, eight, seven, or six of the basic amino acid residues set forth in SEQ ID NO: 1 or a basic amino acid substitution thereof;

optionally wherein the first or second antimicrobial peptide contains at least thirteen, twelve, eleven, ten, nine, eight, seven, or six of the basic amino acid residues set forth in SEQ ID NO: 1.

99. The composition of any one of embodiments 86 to 98, wherein the first or second antimicrobial peptide contains at least ten, nine, eight, seven, or six of the hydrophobic amino acid residues set forth in SEQ ID NO: 1 or a hydrophobic amino acid substitution thereof;

optionally wherein the first or second antimicrobial peptide contains at least ten, nine, eight, seven, or six of the hydrophobic amino acid residues set forth in SEQ ID NO: 1.

100. The composition of any one of embodiments 86 to 99, wherein:

the first or second antimicrobial peptide has a net positive charge of at least about +9; or the first or second antimicrobial peptide has a net positive charge of at least about +9 to about +13.

101. The composition of any one of embodiments 86 to 100, wherein:

the amino acid sequence of the first or second antimicrobial polypeptide comprises at least 30% or at least 35% of hydrophobic amino acids;

or the amino acid sequence of the first or second antimicrobial polypeptide comprises between 30% and 40% or between 35% and 40% of hydrophobic amino acids.

102. The composition of any one of embodiments 86 to 101, wherein first or second antimicrobial polypeptide comprises a C-terminus cysteine residue that forms a disulfide bond with another cysteine residue of the polypeptide.

103. The composition of any one of embodiments 86 to 102, wherein:

the first or second antimicrobial polypeptide comprises a defensin gamma core consensus sequence (SEQ ID NO: 8);

the first or second antimicrobial polypeptide comprises the amino acid sequence of SEQ ID NO: 33; or the first or second antimicrobial polypeptide comprises the amino acid sequence of SEQ ID NO: 39.

104. The composition of any one of embodiments 89 to 103, wherein the spacer peptide comprises the amino acid sequence of SEQ ID NO: 9 or 18-28, or a variant of any one of the amino acids sequences of SEQ ID NO: 9 or 18-28, having 1, 2, or 3 conservative amino acid substitutions;

optionally wherein the spacer peptide comprises or consists of APKKVEP (SEQ ID NO: 9) or GGKAGK-KAPK (SEQ ID NO: 21).

105. The composition of any one of embodiments 86 to 104, further comprising a non-peptidic antimicrobial agent.

106. The composition of any one of embodiments 86 to 105, wherein the first and/or the second antimicrobial peptide are provided at a concentration of about 0.1, 0.5, 1.0, or 5 μg/ml to about 1, 5, 20, 50, or 100 mg/ml for a liquid composition or at a concentration of about 0.1, 0.5, 1.0, or 5 μg/gram to about 1, 5, 20, 50, or 100 mg/gram for a powder or solid composition.

107. A method for preventing or reducing crop damage by a plant pathogenic microbe comprising the step of contacting a plant, a plant seed, or other part of said plant with an effective amount of the composition of any one of embodiments 86 to 106.

108. The method of embodiment 107, wherein the plant pathogenic microbe is a *Fusarium* sp., *Alternaria* sp., *Verticillium* sp., *Phytophthora* sp., *Colletotrichum* sp., *Botrytis* sp., *Cercospora* sp., *Phakopsora* sp. *Rhizoctonia* sp., *Sclerotinia* sp., *Pythium* sp., *Phoma* sp., *Gaeumannomces* sp. *Leptoshaeria* sp., or *Puccinia* sp.

109. A medical device comprising the device and the composition of any one of embodiments 86 to 106, wherein the device comprises at least one surface that is topically coated and/or impregnated with the composition.

110. The medical device of embodiment 109, wherein said device is a stent, a catheter, a contact lens, a condom, a patch, or a diaphragm.

111. A method for treating, preventing, or inhibiting a microbial or yeast infection in a subject in need thereof comprising administering to said subject an effective amount of the composition of any one of embodiments 86 to 106 or deploying the medical device of embodiment 109 or 110.

112. The method of embodiment 111, wherein said administration comprises topical, parenteral, and/or intravenous introduction of the composition.

113. The method of embodiment 111 or 112, wherein the subject is a human, livestock, poultry, fish, or a companion animal.

114. The method of any one of embodiments 111 to 113, wherein the microbial or yeast infection is of a mucosal membrane, eye, skin, or a nail and the composition is applied to the mucosal membrane, eye, skin, or nail.

115. The method of any one of embodiments 111 to 114, wherein the microbial infection is by a dermatophyte.

116. The method of any one of embodiments 111 to 115, wherein the dermatophyte is selected from the group consisting of *Trichophyton rubrum, Trichophyton interdigitale, Trichophyton violaceum, Trichophyton tonsurans, Trichophyton soudanense, Trichophyton mentagrophytes, Microsporum flavum, Epidermophyton floccosum,* and *Microsporum gypseum.*

117. The method of any one of embodiments 111 to 116, wherein the microbial infection is by an *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis,* or *Blastomyces* species.

118. The method of any one of embodiments 111 to 117, wherein the yeast infection is a *Candida* species.

119. The method of embodiment 118, wherein the *Candida* species is *Candida albicans, C. glabrata, C. parasilosis, C. tropicalis,* or *C. krusei.*

120. The composition of any one of embodiments 86 to 106 for use in a method of treating, preventing, or inhibiting microbial or yeast infection in a subject in need thereof.

121. The composition of embodiment 120, wherein the subject is a human, livestock, poultry, fish, or a companion animal.

122. The composition of embodiment 120 or 121, wherein the microbial or yeast infection is of a mucosal membrane, eye, skin, or a nail and the composition is applied to the mucosal membrane, eye, skin, or nail.

123. The composition of any one of embodiments 120 to 122, wherein the microbial infection is by a dermatophyte.

124. The composition of embodiment 123, wherein the dermatophyte is selected from the group consisting of *Trichophyton rubrum, Trichophyton interdigitale, Trichophyton violaceum, Trichophyton tonsurans, Trichophyton soudanense, Trichophyton mentagrophytes, Microsporum flavum, Epidermophyton floccosum,* and *Microsporum gypseum.*

125. The composition of embodiment 120 to 122, wherein the microbial infection is by an *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis,* or *Blastomyces* species.

126. The composition of any one of embodiments 120 to 122, wherein the yeast infection is a *Candida* species.

127. The composition of embodiment 126, wherein the *Candida* species is *Candida albicans, C. glabrata, C. parasilosis, C. tropicalis,* or *C. krusei.*

65

66

PUBLICATIONS CITED

Argos, (1990) J Mol Biol. February 20; 211(4): 943-58.

Baron, O. L. and Pauron, D. (2014). Bio-protocol 4(18): e1237.

Bent A F, et al., (1994) Science 265(5180): 1856-60.

Broekaert, W. F., et al., (1990). FEMS Microbiology Letters 69, 55-60.

Broekaert, W. F., et al., (1995). Plant Physiol 108, 1353-1358.

Broekaert, W. F., et al., (1997). Critical Reviews in Plant Sciences 16, 297-323.

Broothaerts W, et al., (2005) Nature. 433(7026):629-33.

Bustin, S. A. (2002) Journal of Molecular Endocrinology 29, 23-39.

Callis, J, Fromm, M, Walbot, V. (1987) Genes Dev. 1987 December; 1(10): 1 183-200.

Cappelini, R. A., and Peterson, J. L. (1965) Mycologia 57, 962-966.

Carrie and Small (2013) Biochimica et Biophysica Acta (BBA) Molecular Cell Research, 1833, (2), 253-259.

Cazzonnelli, C. I. and J. Velten. (2003) Plant Molecular Biology Reporter 21: 271-280.

Collier, R., et al., (2005) Plant J 43: 449-457.

Chen et al., (2013) Adv Drug Deliv Rev.; 65(10): 1357-1369.

Correll, J. C., et al., (1987). Phytopathology 77, 1640-1646.

da Silva Conceicao, A., and Broekaert, W. F. (1999). Plant Defensins. In Pathogenesis-related proteins in plants, S. Muthukrishnan, ed (New York: CRC Press), pp. 247-260.

Davidson et al., (2006) Lipid Research, 47, 440-449.

Dowler et al.; Sci STKE. 2002 Apr. 23; 2002(129):16.

Doyle J J, et al., (1986). J Biol Chem. 261(20):9228-38.

François et al., *Plant Physiology* (2002) 128: 1346-1358.

Frame, B. R., et al., (2002) Plant Physiol. 129(1): 13-22.

Gao, A., et al., (2000). Nature Biotechnology 18, 1307-1310.

George R A, and Heringa (2002) J Protein Eng. 15(11):871-879.

Grant M R, et al., (1995) Science. 269(5225):843-6.

Hammond-Kosack, K. E., Urban, M., Baldwin, T., Daudi, A., Rudd, J. J., Keon, J., Lucas, J. A., Maguire, K., Kornyukhin, D., Jing, H.-C, Bass, C, and Antoniw, J. (2004). 4th International Crop Science Congress. In New directions for a diverse planet, T. Fischer, Turner, N., Angus, J., McIntyre, L., Robertson, M., Borrell, A., Lloyd, D., ed (Brisbane, Australia: The Regional Institute, Ltd, Gosford, Australia).

Hanks, J. N., et al., (2005). Plant Mol Biol 58, 385-399.

Horsch, R. B., et al., (1985) Science. 227: 1229-1231.

Huang et al., (2009) Plant Physiology, 150(3): 1272-1285.

Islam K T, Velivelli SLS, Berg R H, Oakley B, Shah D M. Sci Rep. 2017 Nov. 23; 7(1):16157. doi:10.1038/s41598-017-16508-w.

Kingsman S M, et al., (1985) Biotechnol Genet Eng Rev. 3:377-416.

Koehler S M, and Ho, T H. (1990) Plant Cell. (8):769-83.

Kumar, V. and Jain, M. (2015) J Exp Bot 66: 47-57.

Lam E, and Chua N H. (1991). J Biol Chem. 1991 Sep. 15; 266(26): 17131-5.

Lacerda et al., Frontiers in Microbio. (2014) 5(116):1-10.

Lay, F. T., and Anderson, M. A. (2005) Curr Protein Pept Sci 6, 85-101.

Lee et al., (2015) Plant Physiol. 169(1):471-84.

Li and Teng (2013) Trends Plant Sci 18: 360-366.

Liang, J., Shah, D. M., Wu, Y., Rosenberger, C. A., and Hakimi, S. M. U.S. Pat. No. 6,916,970; issued Jul. 12, 2005.

Mankin, S. L, G. C. Allen, and W. F. Thompson. 1997. Plant Mol Biol Rep 15(2): 186-196.

McElroy, D, et al., (1990) The Plant Cell, Vol. 2, 163-171.

Miller and Cistola (1993) Molecular and Cellular Biochemistry, 123(1): 29-37.

Montiel et al. 2016 Molec. Plant Microb. Inter. 29: 210-219.

Mottram et al., FEBS Lett. (1989) 258(2):211-215.

Murovec et al., Plant Biotechnol J. 2017 August; 15(8): 917-926.

Ramamoorthy V, et al. Cellular Microbiology 2007 June; 9(6):1491-506.

Reiser J, et al., (1990) Adv Biochem Eng Biotechnol.; 43:75-102.

Sagaram U S, Pandurangi R, Kaur J, Smith T J, Shah D M (2011) PLoS One. doi: 10.1371/journal.pone.0018550.

Sagaram U S, El-Mounadi K, Buchko G W, Berg H R, Kaur J, Pandurangi R S, Smith T J, Shah D M. (2013). PLoS One. 2013 Dec. 4; 8 (12): e82485. doi: 10.1371/journal-.pone.0082485 Sambrook, J., and Russell, D. W. (2001). Molecular Cloning: A Laboratory Manual. (Cold Spring Harbor Laboratory Press, Cold Spring Harbor, New York).

Seong, K., et al., (2005) Phytopathology 95, 744-750.

Sjoling and Glaser; Trend Plant Sci., 1998, 3 (4) 136-140.

Sidorov, V, et al., (2006). Plant Cell Rep. 2006 April; 25(4):320-8. (Epub 2005 October 27).

Svitashev et al., (2015) Plant Physiology, 169 (2): 931-945.

Spelbrink, R. G., et al., (2004). Plant Physiol 135, 2055-2067.

Terras, F. R., et al., (1992). J Biol Chem 267, 15301-15309.

Thevissen, K., et al., (2005). Curr Drug Targets 6, 923-928.

Thevissen, K., et al., (1996). J Biol Chem 271, 15018-15025.

Thevissen, K., et al., (2000). Proc Natl Acad Sci USA 97, 9531-9536.

Thevissen, K., et al., (2004). J Biol Chem 279, 3900-3905.

Thomma, B. P., et al., (2003). Curr Drug Targets Infect Disord 3, 1-8.

Thomma, B. P. H. J., Camrnue, B. P. A., and Thevissen, K. (2002). Planta 216, 193-202.

Turner et al., 1993) Protein Eng. 6(1):101-108.

Voytas, D. Annual Review of Plant Biology, Vol. 64: 327-350, 2013.

Tsiatsiani et al., (2012) Physiologia Plantarum 145: 28-40.

Using Antibodies: A Laboratory Manual. (1999). Ed. Harlow and Lane. Cold Spring Harbor Laboratory Press.

Vasil V, et al., (1989) Plant Physiol. 1989 December; 91(4): 1575-1579.

Vasivarama and Kirti (2013a) Plant Cell Tiss Organ Cult, 115:309-319.

Vasivarama and Kirti (2013b) Funct Integr Genomics 13:435-443.

Vriens, K., et al. *Molecules* 2014, 19, 12280-12303; doi: 10.3390/molecules190812280.

Wesley S V, (2001). Plant J. 27(6): 581-590.

Islam K T, Velivelli SLS, Berg R H, Oakley B, Shah D M (2017) A novel bi-domain plant defensin MtDef5 with potent broad-spectrum antifungal activity binds to multiple phospholipids and forms oligomers. Scientific Reports 7 (1): 16157.

Sagaram U S, El-Mounadi K, Buchko G W, Berg H R, Kaur J, Pandurangi R S, Smith T J, Shah D M (2013) Structural and Functional Studies of a Phosphatidic Acid-Binding Antifungal Plant Defensin MtDef4: Identification of an RGFRRR Motif Governing Fungal Cell Entry. PLOS ONE 8 (12): e82485.

Sagaram U S, Pandurangi R, Kaur J, Smith T J, Shah D M (2011) Structure-Activity Determinants in Antifungal Plant Defensins MsDef1 and MtDef4 with Different Modes of Action against *Fusarium graminearum*. PLOS ONE 6 (4): e18550.

Spelbrink R G, Dilmac N, Allen A, Smith T J, Shah D M, Hockerman G H (2004) Differential antifungal and calcium channel-blocking activity among structurally related plant defensins. Plant physiology 135 (4):2055-2067.

Velivelli SLS, Islam K T, Hobson E, Shah D M (2018) Modes of Action of a Bi-domain Plant Defensin MtDef5 Against a Bacterial Pathogen *Xanthomonas campestris*. Frontiers in microbiology 9:934-934.

Wang M, Weiberg A, Lin F-M, Thomma BPHJ, Huang H-D, Jin H (2016) Bidirectional cross-kingdom RNAi and fungal uptake of external RNAs confer plant protection. Nature Plants 2: 16151.

---

What is claimed is:

1. A composition comprising an antimicrobial peptide comprising the amino acid sequence of SEQ ID NO: 1 or the amino acid sequence of SEQ ID NO: 1 and a C-terminal cysteine residue and an agriculturally, pharmaceutically, or veterinarily acceptable carrier, diluent, or excipient.

2. The composition of claim 1, wherein the antimicrobial peptide further comprises an operably linked second antimicrobial peptide and wherein the second antimicrobial peptide is a defensin or nodule specific cysteine rich (NCR) peptide.

3. The composition of claim 1, wherein the antimicrobial peptide and the second antimicrobial peptide are operably linked by a spacer peptide.

4. A medical device comprising the device and the composition of claim 1, wherein the device comprises at least one surface that is topically coated and/or impregnated with the composition.

5. The medical device of claim 4, wherein said device is a stent, a catheter, a contact lens, a condom, a patch, or a diaphragm.

6. The composition of claim 2, wherein the second antimicrobial peptide is a defensin and wherein the defensin comprises an antimicrobial peptide having at least 99% or 100% sequence identity across the entire length of SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17.

7. The composition of claim 1, wherein the antimicrobial peptide comprises the amino acid sequence of SEQ ID NO: 1 and a C-terminal cysteine residue.

8. The composition of claim 1, wherein the antimicrobial peptide comprises SEQ ID NO: 1 and does not have a C-terminal cysteine residue.

* * * * *

SEQUENCE LISTING

```
<160> NUMBER OF SEQ ID NOS: 53

<210> SEQ ID NO 1
<211> LENGTH: 37
<212> TYPE: PRT
<213> ORGANISM: Artificial Sequence
<220> FEATURE:
<223> OTHER INFORMATION: synthetic

<400> SEQUENCE: 1

Ala Phe Ile Gln Leu Ser Lys Pro Cys His Lys Phe Lys Gly Pro Cys
1               5                   10                  15

Ser Ile Val Lys Asn Tyr Arg Ala Arg Cys Arg Lys Gly Tyr Cys Val
            20                  25                  30

Arg Arg Arg Ile Arg
        35

<210> SEQ ID NO 2
<211> LENGTH: 38
<212> TYPE: PRT
<213> ORGANISM: Artificial Sequence
<220> FEATURE:
<223> OTHER INFORMATION: synthetic

<400> SEQUENCE: 2

Ala Phe Cys Ile Gln Leu Ser Lys Pro Cys Ile Ser Asp Lys Glu Cys
1               5                   10                  15

Ser Ile Val Lys Asn Tyr Arg Ala Arg Cys Arg Lys Gly Tyr Cys Val
            20                  25                  30

Arg Arg Arg Ile Arg Cys
        35

<210> SEQ ID NO 3
<211> LENGTH: 36
<212> TYPE: PRT
<213> ORGANISM: Artificial Sequence
<220> FEATURE:
<223> OTHER INFORMATION: synthetic

<400> SEQUENCE: 3

Ala Phe Ile Gln Leu Ser Lys Pro Cys Lys Arg Arg Arg Asp Cys Ser
1               5                   10                  15

Ile Val Lys Asn Tyr Arg Ala Arg Cys Arg Lys Gly Tyr Cys Val Arg
            20                  25                  30

Arg Arg Ile Arg
        35

<210> SEQ ID NO 4
<211> LENGTH: 38
<212> TYPE: PRT
<213> ORGANISM: Artificial Sequence
<220> FEATURE:
<223> OTHER INFORMATION: synthetic
```

-continued

```
<400> SEQUENCE: 4

Ala Phe Cys Ile Gln Leu Ser Lys Pro Cys Lys Arg Arg Arg Asp Cys
1               5                   10                  15

Ser Ile Val Lys Asn Tyr Arg Ala Arg Cys Arg Lys Gly Tyr Cys Val
                20                  25                  30

Arg Arg Arg Ile Arg Cys
        35

<210> SEQ ID NO 5
<211> LENGTH: 36
<212> TYPE: PRT
<213> ORGANISM: Artificial Sequence
<220> FEATURE:
<223> OTHER INFORMATION: synthetic

<400> SEQUENCE: 5

Ala Phe Ile Gln Leu Ser Lys Pro Cys Lys Ser Arg Lys His Cys Ser
1               5                   10                  15

Ile Val Lys Asn Tyr Arg Ala Arg Cys Arg Lys Gly Tyr Cys Val Arg
                20                  25                  30

Arg Arg Ile Arg
        35

<210> SEQ ID NO 6
<211> LENGTH: 38
<212> TYPE: PRT
<213> ORGANISM: Artificial Sequence
<220> FEATURE:
<223> OTHER INFORMATION: synthetic

<400> SEQUENCE: 6

Ala Phe Cys Ile Gln Leu Ser Lys Pro Cys Lys Ser Arg Lys His Cys
1               5                   10                  15

Ser Ile Val Lys Asn Tyr Arg Ala Arg Cys Arg Lys Gly Tyr Cys Val
                20                  25                  30

Arg Arg Arg Ile Arg Cys
        35

<210> SEQ ID NO 7
<211> LENGTH: 36
<212> TYPE: PRT
<213> ORGANISM: Cicer arietinum

<400> SEQUENCE: 7

Ala Phe Ile Gln Leu Ser Lys Pro Cys Ile Ser Asp Lys Glu Cys Ser
1               5                   10                  15

Ile Val Lys Asn Tyr Arg Ala Arg Cys Arg Lys Gly Tyr Cys Val Arg
                20                  25                  30

Arg Arg Ile Arg
        35

<210> SEQ ID NO 8
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
```

```
<222> LOCATION: (4)..(12)
<223> OTHER INFORMATION: Xaa can be any naturally occurring amino acid

<400> SEQUENCE: 8

Gly Xaa Cys Xaa Xaa Xaa Xaa Xaa Xaa Xaa Xaa Xaa Cys
1               5                   10

<210> SEQ ID NO 9
<211> LENGTH: 7
<212> TYPE: PRT
<213> ORGANISM: Artificial Sequence
<220> FEATURE:
<223> OTHER INFORMATION: synthetic

<400> SEQUENCE: 9

Ala Pro Lys Lys Val Glu Pro
1               5

<210> SEQ ID NO 10
<211> LENGTH: 47
<212> TYPE: PRT
<213> ORGANISM: Medicago truncatula

<400> SEQUENCE: 10

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

His Cys Arg Gly Phe Arg Arg Arg Cys Phe Cys Thr Thr His Cys
        35                  40                  45

<210> SEQ ID NO 11
<211> LENGTH: 50
<212> TYPE: PRT
<213> ORGANISM: Medicago truncatula

<400> SEQUENCE: 11

Lys Leu Cys Gln Lys Arg Ser Thr Thr Trp Ser Gly Pro Cys Leu Asn
1               5                   10                  15

Thr Gly Asn Cys Lys Arg Gln Cys Ile Asn Val Glu His Ala Thr Phe
            20                  25                  30

Gly Ala Cys His Arg Gln Gly Phe Gly Phe Ala Cys Phe Cys Tyr Lys
        35                  40                  45

Lys Cys
    50

<210> SEQ ID NO 12
<211> LENGTH: 50
<212> TYPE: PRT
<213> ORGANISM: Medicago truncatula

<400> SEQUENCE: 12

Lys Leu Cys Glu Arg Arg Ser Lys Thr Trp Ser Gly Pro Cys Leu Ile
1               5                   10                  15

Ser Gly Asn Cys Lys Arg Gln Cys Ile Asn Val Glu His Ala Thr Ser
            20                  25                  30

Gly Ala Cys His Arg Gln Gly Ile Gly Phe Ala Cys Phe Cys Lys Lys
        35                  40                  45

Lys Cys
    50
```

-continued

```
<210> SEQ ID NO 13
<211> LENGTH: 107
<212> TYPE: PRT
<213> ORGANISM: Medicago truncatula

<400> SEQUENCE: 13

Lys Leu Cys Gln Lys Arg Ser Thr Thr Trp Ser Gly Pro Cys Leu Asn
1               5                   10                  15

Thr Gly Asn Cys Lys Arg Gln Cys Ile Asn Val Glu His Ala Thr Phe
                20                  25                  30

Gly Ala Cys His Arg Gln Gly Phe Gly Phe Ala Cys Phe Cys Tyr Lys
            35                  40                  45

Lys Cys Ala Pro Lys Lys Val Glu Pro Lys Leu Cys Glu Arg Arg Ser
    50                  55                  60

Lys Thr Trp Ser Gly Pro Cys Leu Ile Ser Gly Asn Cys Lys Arg Gln
65                  70                  75                  80

Cys Ile Asn Val Glu His Ala Thr Ser Gly Ala Cys His Arg Gln Gly
                85                  90                  95

Ile Gly Phe Ala Cys Phe Cys Lys Lys Lys Cys
            100                 105

<210> SEQ ID NO 14
<211> LENGTH: 45
<212> TYPE: PRT
<213> ORGANISM: Taraxacum

<400> SEQUENCE: 14

Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
                20                  25                  30

Asp Gly Val Arg Arg Arg Cys Thr Cys Tyr Lys Lys Cys
            35                  40                  45

<210> SEQ ID NO 15
<211> LENGTH: 50
<212> TYPE: PRT
<213> ORGANISM: Picramnia pentandra

<400> SEQUENCE: 15

Lys Val Cys Thr Lys Pro Ser Lys Phe Phe Lys Gly Leu Cys Gly Thr
1               5                   10                  15

Asp Gly Ala Cys Thr Thr Ala Cys Arg Lys Glu Gly Leu His Ser Gly
                20                  25                  30

Tyr Cys Gln Leu Lys Gly Phe Leu Asn Ser Val Cys Val Cys Arg Lys
        35                  40                  45

His Cys
    50

<210> SEQ ID NO 16
<211> LENGTH: 50
<212> TYPE: PRT
<213> ORGANISM: Picramnia pentandra

<400> SEQUENCE: 16

Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
                20                  25                  30
```

```
Phe Cys Gln Asn Lys Gly Phe Phe Asn Val Val Cys Val Cys Arg Lys
        35                  40                  45

Pro Cys
    50

<210> SEQ ID NO 17
<211> LENGTH: 50
<212> TYPE: PRT
<213> ORGANISM: Picramnia pentandra

<400> SEQUENCE: 17

Lys Val Cys Thr Lys Pro Ser Lys Phe Phe Lys Gly Leu Cys Gly Ala
1               5                   10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Arg Lys
        35                  40                  45

Pro Cys
    50

<210> SEQ ID NO 18
<211> LENGTH: 5
<212> TYPE: PRT
<213> ORGANISM: Artificial Sequence
<220> FEATURE:
<223> OTHER INFORMATION: synthetic

<400> SEQUENCE: 18

Gly Gly Gly Gly Ser
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic

<400> SEQUENCE: 19

Ser Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: synthetic

<400> SEQUENCE: 20

Asn Asn Glu Ser Ala Ser Pro Ala Ser Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic

<400> SEQUENCE: 21

Gly Gly Lys Ala Gly Lys Lys Ala Pro Lys
1               5                   10
```

```
<210> SEQ ID NO 22
<211> LENGTH: 10
<212> TYPE: PRT
<213> ORGANISM: Artificial Sequence
<220> FEATURE:
<223> OTHER INFORMATION: synthetic

<400> SEQUENCE: 22

Ala Thr Pro Pro Thr Pro Thr Pro Pro Lys
1               5               10

<210> SEQ ID NO 23
<211> LENGTH: 11
<212> TYPE: PRT
<213> ORGANISM: Artificial Sequence
<220> FEATURE:
<223> OTHER INFORMATION: synthetic

<400> SEQUENCE: 23

Glu Pro Pro Ser Leu Thr Ser Thr Pro Leu Asn
1               5               10

<210> SEQ ID NO 24
<211> LENGTH: 9
<212> TYPE: PRT
<213> ORGANISM: Artificial Sequence
<220> FEATURE:
<223> OTHER INFORMATION: synthetic

<400> SEQUENCE: 24

Gly Gly Lys Pro Gly Lys Lys Ala Pro
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic

<400> SEQUENCE: 25

Ala Gly Arg Gly Asp Lys Lys
1               5

<210> SEQ ID NO 26
<211> LENGTH: 11
<212> TYPE: PRT
<213> ORGANISM: Artificial Sequence
<220> FEATURE:
<223> OTHER INFORMATION: synthetic

<400> SEQUENCE: 26

Pro Pro Thr Pro Pro Ser Pro Pro Thr Arg Pro
1               5               10

<210> SEQ ID NO 27
<211> LENGTH: 5
<212> TYPE: PRT
<213> ORGANISM: Artificial Sequence
<220> FEATURE:
<223> OTHER INFORMATION: synthetic

<400> SEQUENCE: 27

Glu Glu Lys Lys Asn
1               5

<210> SEQ ID NO 28
```

```
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is glutamate or aspartate
<220> FEATURE:
<221> NAME/KEY: VARIANT
<222> LOCATION: (2)..(2)
<223> OTHER INFORMATION: Xaa is glutamate or aspartate
<220> FEATURE:
<221> NAME/KEY: VARIANT
<222> LOCATION: (3)..(3)
<223> OTHER INFORMATION: Xaa is lysine or arginine
<220> FEATURE:
<221> NAME/KEY: VARIANT
<222> LOCATION: (4)..(4)
<223> OTHER INFORMATION: Xaa is lysine or arginine
<220> FEATURE:
<221> NAME/KEY: VARIANT
<222> LOCATION: (5)..(5)
<223> OTHER INFORMATION: Xaa is asparagine or glutamine

<400> SEQUENCE: 28

Xaa Xaa Xaa Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic

<400> SEQUENCE: 29

Arg Gly Phe Arg Arg Arg
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic

<400> SEQUENCE: 30

Lys Arg Glu Ala Glu Ala
1               5

<210> SEQ ID NO 31
<211> LENGTH: 79
<212> TYPE: PRT
<213> ORGANISM: Artificial Sequence
<220> FEATURE:
<223> OTHER INFORMATION: synthetic

<400> SEQUENCE: 31

Ala Phe Ile Gln Leu Ser Lys Pro Cys Ile Ser Asp Lys Glu Cys Ser
1               5                   10                  15

Ile Val Lys Asn Tyr Arg Ala Arg Cys Arg Lys Gly Tyr Cys Val Arg
            20                  25                  30

Arg Arg Ile Arg Ala Pro Lys Lys Val Glu Pro Ala Phe Ile Gln Leu
        35                  40                  45

Ser Lys Pro Cys Ile Ser Asp Lys Glu Cys Ser Ile Val Lys Asn Tyr
    50                  55                  60
```

```
Arg Ala Arg Cys Arg Lys Gly Tyr Cys Val Arg Arg Arg Ile Arg
65                  70                  75

<210> SEQ ID NO 32
<211> LENGTH: 82
<212> TYPE: PRT
<213> ORGANISM: Artificial Sequence
<220> FEATURE:
<223> OTHER INFORMATION: synthetic

<400> SEQUENCE: 32

Ala Phe Ile Gln Leu Ser Lys Pro Cys Ile Ser Asp Lys Glu Cys Ser
1               5                   10                  15

Ile Val Lys Asn Tyr Arg Ala Arg Cys Arg Lys Gly Tyr Cys Val Arg
            20                  25                  30

Arg Arg Ile Arg Gly Gly Lys Ala Gly Lys Lys Ala Pro Lys Ala Phe
        35                  40                  45

Ile Gln Leu Ser Lys Pro Cys Ile Ser Asp Lys Glu Cys Ser Ile Val
    50                  55                  60

Lys Asn Tyr Arg Ala Arg Cys Arg Lys Gly Tyr Cys Val Arg Arg Arg
65                  70                  75                  80

Ile Arg

<210> SEQ ID NO 33
<211> LENGTH: 10
<212> TYPE: PRT
<213> ORGANISM: Artificial Sequence
<220> FEATURE:
<223> OTHER INFORMATION: synthetic

<400> SEQUENCE: 33

Gly Tyr Cys Val Arg Arg Arg Ile Arg Cys
1               5                   10

<210> SEQ ID NO 34
<211> LENGTH: 6
<212> TYPE: PRT
<213> ORGANISM: Artificial Sequence
<220> FEATURE:
<223> OTHER INFORMATION: synthetic

<400> SEQUENCE: 34

His Lys Phe Lys Gly Pro
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic

<400> SEQUENCE: 35

Ile Ser Asp Lys Glu
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic

<400> SEQUENCE: 36
```

```
Lys Arg Arg Arg Asp
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic

<400> SEQUENCE: 37

Lys Ser Arg Lys His
1               5

<210> SEQ ID NO 38
<211> LENGTH: 10
<212> TYPE: PRT
<213> ORGANISM: Artificial Sequence
<220> FEATURE:
<223> OTHER INFORMATION: synthetic

<400> SEQUENCE: 38

Gly His Cys Arg Gly Phe Arg Arg Arg Cys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: (4)..(4)
<223> OTHER INFORMATION: Xaa is phenylalanine, tryptophan, isoleucine,
      leucine, methionine, or alanine
<220> FEATURE:
<221> NAME/KEY: VARIANT
<222> LOCATION: (5)..(5)
<223> OTHER INFORMATION: Xaa is arginine, lysine, or histidine
<220> FEATURE:
<221> NAME/KEY: VARIANT
<222> LOCATION: (6)..(6)
<223> OTHER INFORMATION: Xaa is arginine, lysine, or histidine
<220> FEATURE:
<221> NAME/KEY: VARIANT
<222> LOCATION: (7)..(7)
<223> OTHER INFORMATION: Xaa is arginine, lysine, or histidine
<220> FEATURE:
<221> NAME/KEY: VARIANT
<222> LOCATION: (8)..(8)
<223> OTHER INFORMATION: Xaa is phenylalanine, tryptophan, isoleucine,
      leucine, methionine, or alanine
<220> FEATURE:
<221> NAME/KEY: VARIANT
<222> LOCATION: (9)..(9)
<223> OTHER INFORMATION: Xaa is arginine, lysine, or histidine
<220> FEATURE:
<221> NAME/KEY: VARIANT
<222> LOCATION: (10)..(10)
<223> OTHER INFORMATION: Xaa is cysteine or is absent

<400> SEQUENCE: 39

Gly Tyr Cys Xaa Xaa Xaa Xaa Xaa Xaa Xaa
1               5                   10

<210> SEQ ID NO 40
<211> LENGTH: 38
<212> TYPE: PRT
<213> ORGANISM: Artificial Sequence
<220> FEATURE:
<223> OTHER INFORMATION: synthetic
```

```
<400> SEQUENCE: 40

Ala Phe Cys Gln Leu Ser Lys Pro Cys His Lys Phe Lys Gly Pro Cys
1               5                   10                  15

Ser Ile Val Lys Asn Tyr Arg Ala Arg Cys Arg Lys Gly Tyr Cys Val
            20                  25                  30

Arg Arg Arg Ile Arg Cys
        35

<210> SEQ ID NO 41
<211> LENGTH: 4
<212> TYPE: PRT
<213> ORGANISM: Artificial Sequence
<220> FEATURE:
<223> OTHER INFORMATION: synthetic

<400> SEQUENCE: 41

Lys Asp Glu Leu
1

<210> SEQ ID NO 42
<211> LENGTH: 5
<212> TYPE: PRT
<213> ORGANISM: Artificial Sequence
<220> FEATURE:
<223> OTHER INFORMATION: synthetic

<400> SEQUENCE: 42

Gln Ser Asp Lys Asp
1               5

<210> SEQ ID NO 43
<211> LENGTH: 12
<212> TYPE: DNA
<213> ORGANISM: Artificial Sequence
<220> FEATURE:
<223> OTHER INFORMATION: synthetic

<400> SEQUENCE: 43
ctcgagaaaa ga                                                                12

<210> SEQ ID NO 44
<211> LENGTH: 12
<212> TYPE: DNA
<213> ORGANISM: Artificial Sequence
<220> FEATURE:
<223> OTHER INFORMATION: synthetic

<400> SEQUENCE: 44
tagtaatcta ga                                                                12

<210> SEQ ID NO 45
<211> LENGTH: 9
<212> TYPE: PRT
<213> ORGANISM: Cicer arietinum

<400> SEQUENCE: 45

Gly Tyr Cys Val Arg Arg Arg Ile Arg
1               5

<210> SEQ ID NO 46
<211> LENGTH: 4
<212> TYPE: PRT
<213> ORGANISM: Artificial Sequence
<220> FEATURE:
```

<223> OTHER INFORMATION: synthetic

<400> SEQUENCE: 46

Gly Gly Gly Gly
1

<210> SEQ ID NO 47
<211> LENGTH: 47
<212> TYPE: PRT
<213> ORGANISM: Artificial Sequence
<220> FEATURE:
<223> OTHER INFORMATION: synthetic

<400> SEQUENCE: 47

Arg Thr Cys Glu Ser Gln Ser His Lys Phe Lys Gly Pro Cys Ala Ser
1               5                   10                  15

Asp His Asn Cys Ala Ser Val Cys Gln Thr Glu Arg Phe Ser Gly Gly
            20                  25                  30

Arg Cys Arg Gly Phe Arg Arg Arg Cys Phe Cys Thr Thr His Cys
        35                  40                  45

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Gly Arg Cys Arg Gly Phe Arg Arg Arg Cys
1               5                   10

<210> SEQ ID NO 49
<211> LENGTH: 108
<212> TYPE: DNA
<213> ORGANISM: Artificial Sequence
<220> FEATURE:
<223> OTHER INFORMATION: synthetic

<400> SEQUENCE: 49
gcttttattc aattgtctaa gccatgtatc tctgataagg aatgttctat cgttaagaac      60
tacagagcta gatgtagaaa aggttattgt gttagaagaa gaattaga                  108

<210> SEQ ID NO 50
<211> LENGTH: 237
<212> TYPE: DNA
<213> ORGANISM: Artificial Sequence
<220> FEATURE:
<223> OTHER INFORMATION: synthetic

<400> SEQUENCE: 50
gccttcattc agttgtccaa gccatgtatt agtgataaag agtgttcaat cgtcaagaat      60
tacagagcca gatgcagaaa aggttactgt gttagaagaa gaattagagc tccaaagaaa     120
gttgaacctg ctttttattca attgtctaag ccatgtatct ctgataaaga gtgttctatc    180
gtcaagaact acagagcaag atgcagaaaa ggttattgtg tcagaagaag aatcaga        237

<210> SEQ ID NO 51
<211> LENGTH: 246
<212> TYPE: DNA
<213> ORGANISM: Artificial Sequence
<220> FEATURE:
<223> OTHER INFORMATION: synthetic -continued

```
<400> SEQUENCE: 51
gcttttattc aattgtctaa gccatgtatc tctgataagg aatgttctat cgttaagaac      60
tacagagcta gatgtagaaa gggttattgt gttagaagaa gaattagagg tggtaaagct     120
ggtaaaaagg ctccaaaagc tttcattcaa ttgtctaagc cttgtatctc tgataaggag     180
tgttctatcg ttaaaaatta tagagctaga tgcagaaaag gatactgcgt cagaagaaga     240
attaga                                                                246

<210> SEQ ID NO 52
<211> LENGTH: 111
<212> TYPE: DNA
<213> ORGANISM: Artificial Sequence
<220> FEATURE:
<223> OTHER INFORMATION: synthetic

<400> SEQUENCE: 52
gcttttattc aattgtctaa gccatgtcat aagttcaaag gtccttgttc tattgttaag      60
aactacagag ctagatgtag aaaaggttat tgtgttagaa gaagaattag a              111

<210> SEQ ID NO 53
<211> LENGTH: 114
<212> TYPE: DNA
<213> ORGANISM: Artificial Sequence
<220> FEATURE:
<223> OTHER INFORMATION: synthetic

<400> SEQUENCE: 53
gctttctgta tccaattgtc taagccatgt atctctgata aggaatgttc tatcgttaag      60
aactacagag ctagatgtag aaagggttac tgtgttagaa gaagaattag atgt           114
```